US012692251B2

(12) United States Patent
Waetzig et al.

(10) Patent No.: US 12,692,251 B2
(45) Date of Patent: Jul. 28, 2026

(54) PRALSETINIB PHARMACEUTICAL COMPOSITIONS

(71) Applicant: Rigel Pharmaceuticals, Inc., South San Francisco, CA (US)

(72) Inventors: Joshua Waetzig, Cambridge, MA (US); Gordon D. Wilkie, Cambridge, MA (US); Debra L. Mazaik, Cambridge, MA (US); Csanad M. Varga, Cambridge, MA (US); Lia Rogal, Cambridge, MA (US); Lauren MacEachern, Halifax (CA); Kimberly Jean Miller, Halifax (CA); Shellie Rigby-Singleton, Nottingham (GB); Ian A. Barker, Nottingham (GB); Robert J. Harris, Nottingham (GB); Aimee J. Spenceley, Nottingham (GB); Dipak Gordhan, Nottingham (GB)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 691 days.

(21) Appl. No.: 18/000,166

(22) PCT Filed: May 28, 2021

(86) PCT No.: PCT/US2021/034811

§ 371 (c)(1),
(2) Date: Nov. 29, 2022

(87) PCT Pub. No.: WO2021/243186

PCT Pub. Date: Dec. 2, 2021

(65) Prior Publication Data

US 2023/0203009 A1 Jun. 29, 2023

Related U.S. Application Data

(60) Provisional application No. 63/032,030, filed on May 29, 2020.

(51) Int. Cl.
*A61K 9/20* (2006.01)
*A61K 9/46* (2006.01)
*A61K 9/48* (2006.01)
*A61K 31/506* (2006.01)
*C07D 401/14* (2006.01)

(52) U.S. Cl.
CPC .......... *C07D 401/14* (2013.01); *A61K 9/0007* (2013.01); *A61K 9/2009* (2013.01); *A61K 9/2013* (2013.01); *A61K 9/2027* (2013.01); *A61K 9/2054* (2013.01); *A61K 9/4825* (2013.01); *A61K 9/485* (2013.01); *A61K 9/4858* (2013.01); *A61K 9/4866* (2013.01); *A61K 31/506* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,088,806 | B2 | 1/2012 | Zhang et al. |
| 8,802,697 | B2 | 8/2014 | Bifulco, Jr. |
| 9,126,951 | B2 | 9/2015 | Bifulco, Jr. |
| 9,187,475 | B2 | 11/2015 | Kawamura et al. |
| 9,200,002 | B2 | 12/2015 | Hodous et al. |
| 9,216,172 | B2 | 12/2015 | Kohno et al. |
| 9,297,011 | B2 | 3/2016 | Downing et al. |
| 9,334,263 | B2 | 5/2016 | Hodous et al. |
| 9,340,514 | B2 | 5/2016 | Bifulco, Jr. |
| 9,434,700 | B2 | 9/2016 | Bifulco, Jr. |
| 9,499,522 | B2 | 11/2016 | DiPietro et al. |
| 9,688,680 | B2 | 6/2017 | Hodous |
| 9,695,165 | B2 | 7/2017 | Bifulco, Jr. |
| 9,884,861 | B2 | 2/2018 | Hodous et al. |
| 9,944,651 | B2 | 4/2018 | Hodous et al. |
| 9,994,552 | B2 | 6/2018 | DiPietro et al. |
| 9,994,575 | B2 | 6/2018 | Hodous et al. |
| 10,000,490 | B2 | 6/2018 | Bifulco, Jr. |
| 10,000,496 | B2 | 6/2018 | Hodous et al. |
| 10,017,512 | B2 | 7/2018 | Wenglowsky et al. |
| 10,030,005 | B2 | 7/2018 | Brubaker et al. |
| 10,035,789 | B2 | 7/2018 | Brubaker et al. |

(Continued)

FOREIGN PATENT DOCUMENTS

| | | | |
|---|---|---|---|
| CN | 104844567 | A | 8/2015 |
| CN | 105255927 | A | 1/2016 |

(Continued)

OTHER PUBLICATIONS

U.S. Appl. No. 18/606,346, RET Inhibitor for Use in Treating Cancer Having a RET Alteration, filed Mar. 15, 2024, Pending.
U.S. Appl. No. 18/422,258, Inhibitors of RET, filed Jan. 25, 2024, Pending.
U.S. Appl. No. 15/340,428, U.S. Pat. No. 10,030,005, Inhibitors of RET, filed Nov. 1, 2016.
U.S. Appl. No. 16/041,719, U.S. Pat. No. 10,584,114, Inhibitors of RET, filed Jul. 20, 2018.
U.S. Appl. No. 16/775,646, U.S. Pat. No. 11,279,688, Inhibitors of RET, filed Jan. 29, 2020.

(Continued)

*Primary Examiner* — Susan T Tran
(74) *Attorney, Agent, or Firm* — Jones Day

(57) ABSTRACT

The present disclosure relates to pharmaceutical composition comprising 1) an amorphous solid dispersion comprising pralsetinib, or a pharmaceutically acceptable salt thereof; and a pharmaceutically acceptable hydrophilic polymer; and 2) an effervescent couple; and crystalline forms of pralsetinib and pralsetinib hydrochloride salt, which are useful as a RET selective inhibitors. The present disclosure also provides pharmaceutically acceptable compositions comprising the crystalline forms and methods of using said compositions in the treatment of various disorders.

5 Claims, 17 Drawing Sheets

(56) References Cited

U.S. PATENT DOCUMENTS

| | | | |
|---|---|---|---|
| 10,183,928 | B2 | 1/2019 | Kim et al. |
| 10,196,436 | B2 | 2/2019 | Miduturu |
| 10,202,365 | B2 | 2/2019 | Brooijmans et al. |
| 10,221,154 | B2 | 3/2019 | Bifulco, Jr. et al. |
| 10,227,329 | B2 | 3/2019 | Brubaker et al. |
| 10,584,114 | B2 | 3/2020 | Brubaker et al. |
| 10,774,070 | B2 | 9/2020 | Brooijmans et al. |
| 11,273,160 | B2 | 3/2022 | Evans Raab et al. |
| 11,279,688 | B2 | 3/2022 | Brubaker et al. |
| 11,872,192 | B2 | 1/2024 | Evans Raab et al. |
| 11,963,958 | B2 | 4/2024 | Evans Raab et al. |
| 2012/0316137 | A1 | 12/2012 | Huang et al. |
| 2013/0096136 | A1 | 4/2013 | Hata et al. |
| 2013/0115313 | A1 | 5/2013 | Charrier et al. |
| 2013/0116280 | A1 | 5/2013 | Ju et al. |
| 2014/0187559 | A1 | 7/2014 | Miduturu |
| 2014/0221404 | A1 | 8/2014 | Kohno et al. |
| 2014/0243357 | A1 | 8/2014 | Dar et al. |
| 2014/0272951 | A1 | 9/2014 | Chakravarti et al. |
| 2015/0057335 | A1 | 2/2015 | Kohno et al. |
| 2015/0177246 | A1 | 6/2015 | Shibata et al. |
| 2016/0102097 | A1 | 4/2016 | Hodous et al. |
| 2017/0014413 | A1 | 1/2017 | Downing et al. |
| 2017/0022206 | A1 | 1/2017 | Hodous et al. |
| 2017/0029409 | A1 | 2/2017 | DiPietro et al. |
| 2017/0057953 | A1 | 3/2017 | Hodous et al. |
| 2017/0066773 | A1 | 3/2017 | Wenglowsky et al. |
| 2017/0066812 | A1 | 3/2017 | Bifulco, Jr. |
| 2017/0121312 | A1 | 5/2017 | Brubaker et al. |
| 2017/0145018 | A1 | 5/2017 | Wenglowsky et al. |
| 2017/0174652 | A1 | 6/2017 | Bifulco, Jr. |
| 2017/0204104 | A1 | 7/2017 | Hodous et al. |
| 2017/0253593 | A1 | 9/2017 | Bifulco, Jr. et al. |
| 2017/0267661 | A1 | 9/2017 | Kim et al. |
| 2017/0281633 | A1 | 10/2017 | Boylan et al. |
| 2017/0298069 | A1 | 10/2017 | Brooijmans et al. |
| 2018/0022731 | A1 | 1/2018 | Brooijmans et al. |
| 2018/0022732 | A1 | 1/2018 | Brubaker et al. |
| 2018/0030032 | A1 | 2/2018 | Brubaker et al. |
| 2019/0185454 | A1 | 6/2019 | Brubaker et al. |
| 2019/0192522 | A1 | 6/2019 | Hagel et al. |
| 2020/0407341 | A1 | 12/2020 | Brubaker et al. |
| 2021/0030758 | A1* | 2/2021 | Strum .................. A61K 31/506 |
| 2021/0085680 | A1 | 3/2021 | Evans Raab et al. |
| 2021/0100795 | A1 | 4/2021 | Evans Raab et al. |
| 2021/0100799 | A1 | 4/2021 | Evans Raab et al. |
| 2021/0236489 | A1* | 8/2021 | Wertz ..................... A61K 47/14 |
| 2021/0308134 | A1 | 10/2021 | Hata et al. |
| 2022/0175773 | A1 | 6/2022 | Evans Raab et al. |
| 2022/0265623 | A1* | 8/2022 | Kaufman ............. A61K 9/2018 |
| 2022/0315560 | A1 | 10/2022 | Brubaker et al. |
| 2023/0295121 | A1 | 9/2023 | Waetzig et al. |
| 2024/0059672 | A1 | 2/2024 | Waetzig et al. |

FOREIGN PATENT DOCUMENTS

| | | | |
|---|---|---|---|
| CN | 107980784 | A | 5/2018 |
| CN | 108341782 | A | 7/2018 |
| CN | 111362923 | A | 7/2020 |
| CN | 111440151 | A | 7/2020 |
| EP | 3037547 | A1 | 6/2016 |
| JP | 2015109806 | A | 6/2015 |
| WO | WO-2001/060816 | A1 | 8/2001 |
| WO | WO-2004/009087 | A1 | 1/2004 |
| WO | WO-2005/062795 | A2 | 7/2005 |
| WO | WO-2007/023382 | A2 | 3/2007 |
| WO | WO-2007/087245 | A2 | 8/2007 |
| WO | WO-2007/124221 | A1 | 11/2007 |
| WO | WO-2007/136103 | A1 | 11/2007 |
| WO | WO-2008/061201 | A1 | 5/2008 |
| WO | WO-2009/003136 | A1 | 12/2008 |
| WO | WO-2009/007748 | A2 | 1/2009 |
| WO | WO-2009/014637 | A2 | 1/2009 |
| WO | 2009018415 | A1 | 2/2009 |
| WO | WO-2009/100536 | A1 | 8/2009 |
| WO | WO-2010/006432 | A1 | 1/2010 |
| WO | WO-2010/111056 | A1 | 9/2010 |
| WO | WO-2010/144359 | A1 | 12/2010 |
| WO | WO-2010/144394 | A1 | 12/2010 |
| WO | WO-2011/060295 | A1 | 5/2011 |
| WO | WO-2013/077921 | A2 | 5/2013 |
| WO | WO-2013/133367 | A1 | 9/2013 |
| WO | WO-2013/170159 | A1 | 11/2013 |
| WO | WO-2014/039971 | A1 | 3/2014 |
| WO | WO-2014/050781 | A1 | 4/2014 |
| WO | WO-2014/072220 | A1 | 5/2014 |
| WO | WO-2014/130810 | A1 | 8/2014 |
| WO | WO-2014/141187 | A1 | 9/2014 |
| WO | WO-2014/147640 | A2 | 9/2014 |
| WO | WO-2015/006875 | A1 | 1/2015 |
| WO | WO-2015/079251 | A1 | 6/2015 |
| WO | WO-2016/037578 | A1 | 3/2016 |
| WO | WO-2016/038552 | A1 | 3/2016 |
| WO | WO-2016/075224 | A1 | 5/2016 |
| WO | WO-2016/127074 | A1 | 8/2016 |
| WO | WO-2017/011776 | A1 | 1/2017 |
| WO | WO-2017/079117 | A1 | 5/2017 |
| WO | WO-2017/079121 | A2 | 5/2017 |
| WO | WO-2017/079140 | A1 | 5/2017 |
| WO | WO-2017/100642 | A1 | 6/2017 |
| WO | WO-2017/145050 | A1 | 8/2017 |
| WO | WO-2017/161269 | A1 | 9/2017 |
| WO | WO-2017/178844 | A1 | 10/2017 |
| WO | WO-2017/178845 | A1 | 10/2017 |
| WO | WO-2018/017983 | A1 | 1/2018 |
| WO | WO-2018/022761 | A1 | 2/2018 |
| WO | WO-2018/049233 | A1 | 3/2018 |
| WO | WO-2018/060714 | A1 | 4/2018 |
| WO | WO-2018/064852 | A1 | 4/2018 |
| WO | WO-2018/071447 | A1 | 4/2018 |
| WO | WO-2018/071454 | A1 | 4/2018 |
| WO | WO-2018/102455 | A1 | 6/2018 |
| WO | WO-2018/136661 | A1 | 7/2018 |
| WO | WO-2018/136663 | A1 | 7/2018 |
| WO | WO-2018/183712 | A1 | 10/2018 |
| WO | WO-2018/189553 | A1 | 10/2018 |
| WO | WO-2018/213329 | A1 | 11/2018 |
| WO | WO-2018/237134 | A1 | 12/2018 |
| WO | WO-2019/001556 | A1 | 1/2019 |
| WO | WO-2019/008172 | A1 | 1/2019 |
| WO | WO-2019/126121 | A1 | 6/2019 |
| WO | WO-2019/143977 | A1 | 7/2019 |
| WO | WO-2019/143991 | A1 | 7/2019 |
| WO | WO-2019/143994 | A1 | 7/2019 |
| WO | WO-2019/195471 | A1 | 10/2019 |
| WO | WO-2020033838 | A2 * | 2/2020 ............. A61K 31/47 |
| WO | WO-2021/243186 | A1 | 12/2021 |
| WO | WO-2021/243192 | A1 | 12/2021 |
| WO | WO-2022/120136 | A1 | 6/2022 |

OTHER PUBLICATIONS

U.S. Appl. No. 17/669,785, US 2022-0315560. Inhibitors of RET, filed Feb. 11, 2022.

U.S. Appl. No. 15/548,925, U.S. Pat No. 10,02,365, 2-(Pyridin-3-yl)-pyrimidine Derivatives as RET Inhibitors, filed Aug. 4, 2017.

U.S. Appl. No. 16/228,381, U.S. Pat. No. 10,774,070, 2-(Pyridin-3-yl)-pyrimidine Derivatives as RET Inhibitors, filed Dec. 20, 2018.

U.S. Appl. No. 15/462,255, U.S. Pat. No. 10,183,928, Inhibitors of RET, filed Mar. 17, 2017.

U.S. Appl. No. 15/657,057, U.S. Pat. No. 10,227,329, Compounds Useful for Treating Disorders Related to RET, filed Jul. 21, 2017.

U.S. Appl. No. 15/660,840, U.S. Pat. No. 10,035,789, Compounds Useful for Treating Disorders Related to RET, filed Jul. 26, 2017.

U.S. Appl. No. 17/061,743, US 2021-0085680, RET Inhibitor for Use in Treating Cancer Having a RET Alteration, filed Oct. 2, 2020.

U.S. Appl. No. 17/127,041, U.S. Pat. No. 11,273,160, RET Inhibitor for Use in Treating Cancer Having a RET Alteration, filed Dec. 18, 2020.

U.S. Appl. No. 17/377,885, US2022-0175773, RET Inhibitor for Use in Treating Cancer Having a RET Alteration. filed Jul. 16, 2021.

U.S. Appl. No. 17/267,149, US 2021-0308134, Treatment of EGFR-Mutant Cancer, filed Feb. 9, 2021.

(56) References Cited

OTHER PUBLICATIONS

U.S. Appl. No. 18/255,402, Method of Preparing Pralsetinib, filed Jun. 1, 2023.
U.S. Appl. No. 18/000,168, Solid Forms of Pralsetinib, filed Nov. 29, 2022.
Kang et al., "Osimertinib and Cabozantinib Combinatorial Therapy in an EGFR-Mutant Lung Adenocarcinoma Patient with Multiple MET Secondary-Site Mutations after Resistance to Crizotinib," Journal of Thoracic Oncology, Apr. 2018, vol. 13, No. 4, pp. e49-e53.
Zhang et al., "Activation of the AXL kinases causes resistance to EGFR-targeted therapy in lung cancer," Nature Genetics, 2012, vol. 44, No. 8, pp. 852-860.
Smith et al., "Role of ERBB signaling in RET-rearranged lung cancer and contribution of EGFR amplification to cabozantinib resistance," Journal of Clinical Oncology, 2017, vol. 35, No.15_suppl, Abstract No. 11583.
Neal et la., "Erlotinib, cabozantinib, or erlotinib plus cabozantinib as second-line or third-line treatment of patients with EGFR wild-type advanced non-small-cell lung cancer (ECOG-ACRIN 1512): a randomised, controlled, open-label multicentre, phase 2 trial," Lancet Oncol, 2016, vol. 17, pp. 1661-1671.
Wang et al., "Abstract 4110: Combinatory approaches targeting EGFR, HER2 and c-MET in recurrent SCCHN," Cancer Res, 2017, vol. 77, No. 13_Supplement, Abstract No. 4110.
Gainor et al., "Pralsetinib for RET fusion-positive non-small-cell lung cancer (ARROW): a multi-cohort, open-label, phase ½study," Lancet Oncology, 2021, 22(7), 959-969 (supplementary appendix) (218 pages).
Gainor et al., "Pralsetinib for RET fusion-positive non-small-cell lung cancer (ARROW): a multi-cohort, open-label, phase ½study," Lancet Oncology, 2021, 22(7), 959-969.
Konno, "Effect of polymers on stabilization of drugs in solid dispersions," Pharmaceutics, 2011, 71(2), pp. 109-113.
Phase 1 Cancer Clinical Trials: a Practical Guide, Second Edition, Eds. E.A. Eisenhauer et al., Chapter 4, Basics of Phase I Design: First-in-Human Studies, Oxford University Press, 2015 (37 pages).
Tanno et al., "Evaluation of Hypromellose Acetate Succinate (HPMCAS) as a Carrier in Solid Dispersions," Drug Dev. Ind. Pharm., 2004, vol. 30, No. 1, pp. 9-17 (10 pages).
Abdel-Rahman, O. and M. Fouad (2014) "Risk of cardiovascular toxicities in patients with solid tumors treated with sunitinib, axitinib, cediranib or regorafenib: an updated systematic review and comparative meta-analysis" Crit Rev Oncol Hematol, 92:194-207.
Ahn M. et al. "OA 09.03 TATTON Ph Ib Expansion Cohort: Osimertinib plus Savolitinib for Pts with EGFR-Mutant MET-Amplified NSCLC after Progression on Prior EGFR-TKI." J Thorac Oncol. 12(11) S1768, 2017.
Anonymous "BLU-667 Targets RET-Altered Cancers" Cancer Discovery, vol. 8, No. 6, OF8, Jun. 2018 (Jun. 2018), p. 5pp, XP002792436, Retrieved from the Internet: URL:http://cancerdiscovery.aacrjournals.org/content/8/6/OF8.long [retrieved on Jun. 25, 2019].
Anonymous "Estimating the Maximum Safe Starting Dose in Initial Clinical Trials for Therapeutics in Adult Healthy Volunteers", Guidance for Industry, Jul. 1, 2005 (Jul. 1, 2005), pp. 1-30, XP093000005, Retrieved from the Internet: URL:https://www.fda.gov/media/ 72309/download [retrieved on Nov. 21, 2022].
Anonymous, "Phase 1 Study of the Highly-selective RET Inhibitor BLU-667 in Patients With Thyroid Cancer, Non-Small Cell Lung Cancer, and Other Advanced Solid Tumors," ClinicalTrials.org Internet Citation, Feb. 7, 2020, p. 12pp, XP002783685.
Anonymous: "Phase 1 Study of the Highly-selective RET Inhibitor BLU-667 in Patients With Thyroid Cancer, Non-Small Cell Lung Cancer, and Other Advanced Solid Tumors," Internet Citation, Apr. 21, 2017, Retrieved from the Internet: URL:https://www.clinicaltrials.gov/ct2/history/NCT03037385?V_3=View#StudyPageTop.
Antonescu, C.R. et al. (Jul. 2015) "Molecular Characterization of Inflammatory Myofibroblastic Tumors with Frequent ALK and ROS1 Fusions and Rare Novel RET Gene Rearrangement" Am J Surg Pathol, 39(7):957-967. HHS Public Access Author Manuscript;available in PMC Jul. 1, 2015 (19 pages).
Arighi, E. et al. (2005) "RET tyrosine kinase signaling in development and cancer" Cytokine & Growth Factor Reviews, 16:441-467.
Baselga, J. et al. (2005) "Phase II and Tumor Pharmacodynamic Study of Gefitinib in Patients with Advanced Breast Cancer" J Clin Oncol, 23(23):5323-5333.
Bentzien, F. et al. (2013) "In Vitro and in Vivo Activity of Cabozantinib (XL184), an Inhibitor of RET, MET, and VEGFR2, in a Model of Medullary Thyroid Cancer" Thyroid, 23(12):1569-1577.
Brandt, W. et al. (2010) "Inhibitors of the RET tyrosine kinase based on a 2-(alkylsulfanyl)-4-(3-thienyl) nicotinonitrile scaffold" Eur J Med Chem, 45:2919-2927.
Brown et al. (1984) "Heterocyclic Amplifiers of Phleomycin. IV Pyrimidinylpurines, Phenylpyrimidines and Related Systems with Basic Side Chains," Aust. J. Chem., 37:2093-101.
Caira (1998) "Crystalline Polymorphism of Organic Compounds," Topics in Current Chemistry 198:163-208.
Caprelsa (vandetanib) "Full Prescribing Information" Reference ID: 3964956, Cambridge, MA: Sanofi Genzyme; 2016.
Carlomagno, F et al. (Feb. 1995) "Point Mutation of the Ret Proto-oncogene in the TT Human Medullary Thyroid Carcinoma Cell Line" Biochem Biophys Res Common, 207(3):1022-1028.
Cascone, T. et al., "Significant Systemic and CNS Activity of RET Inhibitor Vandetanib Combined with mTOR Inhibitor Everolimus in Patients with Advanced NSCLC with RET Fusion", J. of Clinical Oncology 34, No. 15, 2 pages.
Ceccherini, I. et al. (1997) "Somatic in frame deletions not involving juxtamembranous cysteine residues strongly activate the RET proto-oncogene" Oncogene, 14:2609-2612.
Chalice Software Technical Guide, Horizon CombinatoRx Inc., Cambridge, MA, USA (downloaded Jul. 2018).
Chen, M-H et al. (2014) "Antitumor activity of the combination of a HSP90 inhibitor and a PI3K/mTOR dual inhibitor against cholangiocarcinoma," Oncotarget, 5(8):2372-2389.
Cometriq (cabozantinib)"Full Prescribing Information" Reference ID: 3964956, South San Francisco, CA: Exelixix, Inc.; 2018.
Drilon et al. (2018) "Targeting RET-driven cancers: lessons from evolving preclinical and clinical landscapes," *Nature Reviews Clinical Oncology* 15:151-167.
Druker, B.J. et al. (2001) "Efficacy and Safety of a Specific Inhibitor of the BCR-ABL Tyrosine Kinase in Chronic Myeloid Leukemia" New Engl J Med, 344(14):1031-1037.
Eisenhauer, E.A. et al. (2009) "New response evaluation criteria in solid tumours: Revised RECIST guideline (version 1.1)" Eur J Cancer, 45:228-247.
Elisei, R. et al. (2008) "Prognostic Significance of Somatic RET Oncogene Mutations in Sporadic Medullary Thyroid Cancer: A 10-Year Follow-Up Study" J Clin Endocrinol Metab, 93(3):682-687.
Engelman J.A. et al. "MET Amplification Leads to Gefitinib Resistance in Lung Cancer by Activating ERBB3 Signaling." Science, 2007, 316 (5827), pp. 1039-1043.
Evans, E. (May 1, 2016) "The Development of Potent and Selective RET Inhibitors" Slides presented at the 2016 Annual Meeting of the International Thyroid Oncology Group at the University of Colorado (19 pages).
Fagin, J.A. et al. "Biologic and Clinical Perspectives on Thyroid Cancer." N Engl J Med. 2016, 375 (11) pp. 1054-1067.
Fang, P. et al. (Feb. 2016) "Detection of a novel RET gene fusion in a non-small cell lung cancer patient using AMP chemistry" J Thorac Oncol, 11.2:S21-S22.
Ferrara et al. "Clinical and Translational Implications of RET Rearrangements in Non-Small Cell Lung Cancer," Journal of Thoracic Oncology, 2018, 13, pp. 27-45.
Gainor J.F. et al. "Dramatic Response to Combination Erlotinib and Crizotinib in a Patient with Advanced, EGFR-Mutant Lung Cancer Harboring De Novo MET Amplification." J Thorac Oncol. 11(7) 2016, pp. e83-e85.
Gautschi, O. et al. (2016) "Targeting RET in patients with RET-rearranged lung cancers: Results from a global registry" J Clin Oncol, 34(15S) (suppl; abstr 9014).

(56) References Cited

OTHER PUBLICATIONS

Gild, M.L. et al. (Oct. 2013) "Targeting mTOR in RET mutant medullary and differentiated thyroid cancer cells" Endocr Re/at Cancer, 20(5):659-667. HHS Public Access Author Manuscript; available in PMC Mar. 27, 2015 (16 pages).
Graham et al., 17 Bioorganic & Medicinal Chemistry, 5886-5893 (2007).
Grubbs, E.G. et al. (Mar. 2015) "RET Fusion as a Novel Driver of Medullary Thyroid Carcinoma" J Clin Endocrinol Metab, 100:788-793.
Halkova, T. et al. (2015) "A novel RET/PTC variant detected in a pediatric patient with papillary thyroid cancer without ionization history" Hum Pathol, 46:1962-1969.
Hayashi, H. et al. (2000) "Characterization of intracellular signals via tyrosine 1062 in RET activated by glial cell line-derived neurotrophic factor" Oncogene, 19:4469-4475.
Hilfiker et al. (2006) "Relevance of Solid-state Properties for Pharmaceutical Products," Polymorphism in the Pharmaceutical Industry, XP002528052, 19 pages.
Horiike, A. et al. (2016) "Sorafenib treatment for patients with RET fusion-positive non-small cell lung cancer" Lung Cancer, 93:43-46.
Hughes (2021) "Review of Synthetic Routes and Crystalline Forms of the Oncology Drugs Capmatinib, Selpercatinib, and Pralsetinib," Org. Process Res. Dev. 25:2192-2204.
International Search Report and Written Opinion dated Apr. 29, 2016, in International Patent Application No. PCT/US2016/016808, filed Feb. 5, 2016, by Blueprint Medicines Corp. (8 pages).
International Search Report and Written Opinion dated Aug. 16, 2021, in International Patent Application No. PCT/US2021/034823, filed May 28, 2021, by Blueprint Medicines Corp. (14 pages).
International Search Report and Written Opinion dated Feb. 24, 2022, in International Patent Application No. PCT/US2021/061754, filed Dec. 3, 2021, by Blueprint Medicines Corp. (16 pages).
International Search Report and Written Opinion dated Jan. 18, 2017, in International Patent Application No. PCT/US2016/059879, filed Nov. 1, 2016, by Blueprint Medicines Corp. (12 pages).
International Search Report and Written Opinion dated Jun. 12, 2017, in International Patent Application No. PCT/US2017/022969, filed Mar. 17, 2017, by Blueprint Medicines Corp. (12 pages).
International Search Report and Written Opinion dated May 11, 2021, in International Patent Application No. PCT/US2021/034811, filed May 28, 2021, by Blueprint Medicines Corp. (16 pages).
International Search Report and Written Opinion dated Oct. 12, 2017, in International Patent Application No. PCT/US2017/043964, filed Jul. 26, 2017, by Blueprint Medicines Corp. (13 pages).
International Search Report and Written Opinion dated Oct. 25, 2017, in International Patent Application No. PCT/US2017/043340, filed Jul. 21, 2017, by Blueprint Medicines Corp. (14 pages).
International Search Report and Written Opinion mailed Aug. 21, 2018, in International Patent Application No. PCT/US2018/032794, filed May 15, 2018, by Blueprint Medicines Corp. (18 pages).
International Search Report and Written Opinion of the International Searching Authority for Intenational Application No. PCT/US2019/025655 mailed Jul. 23, 2019 (16 pages).
International Search Report and Written Opinion of the International Searching Authority for International Application No. PCT/US2019/045919 mailed Jan. 22, 2020 (11 pages).
Jin, N. et al. (Oct. 1, 20115), "Synergistic Action of a RAF Inhibitor and a Dual PI3K/mTOR Inhibitor in Thyroid Cancer," Clin Cancer Res, 17(20):6482-6489.
Joung, J.Y. et al. (2016) "Diffuse sclerosing variant of papillary thyroid carcinoma: major genetic alterations and prognostic implications" Histopathology, 69:45-53.
Jovanovic, R. et al. (2015) "Novel RET Mutations in Macedonian Patients with Medullary Thyroid Carcinoma: Genotype-Phenotype Correlations" Prilozi, 36(1):93-107.
Kamil et al. "Dose estimation, conversion and translation from animal to human and human to animal for clinical and animal studies", Int. J. Biol. Biotech., Jul. 1, 2017 (Jul. 1, 2017), pp. 311-317, XP093000013, Retrieved from the Internet: URL:https://www.researchgate.net/publication/322329638_Dose_estimation_conversion_and_translation_from_animal_to_human_and_human_to_animal for clinical_and_animal studies [retrieved on Nov. 21, 2022].
Karrasch, T. et al. (2016) "How to Assess the Clinical Relevance of Novel RET Missense Variants in the Absence of Functional Studies?" Eur Thyroid J, 5:73-77.
Kato, S. et al. (Apr. 15, 2017) "RET Aberrations in Diverse Cancers: Next-Generation Sequencing of 4,871 Patients" Clin Cancer Res, 23(8):1988-1997.
Kim, S.H. et al. (2015) "A New Germline ALA641THR Variant in the Transmembrane Domain of the RET Gene Associated with Medullary Thyroid Cancer" Acta Endocrinologica (Buc), 11.2:189-194.
Klempner et al. "Emergence of RET rearrangement co-existing with activated EGFR mutation in EGFR-mutated NSCLC patients who had progressed on first- or second-generation EGFR TKI" Lung Cancer, Sep. 2015, vol. 89, No. 3, pp. 357-359; abstract, p. 358, col. 1, para 2, p. 359, col. 1, para 2.
Kohno et al. (2023) "RET fusion gene: Translation to personalized lung cancer therapy," Cancer Sci 104(11):1396-1400.
Krampitz, G.W. and J.A. Norton (2014) "RET Gene Mutations (Genotype and Phenotype) of Multiple Endocrine Neoplasia Type 2 and Familial Medullary Thyroid Carcinoma" Cancer, 120:1920-1931.
Kuster, B. (Ed.) (2012) Kinase Inhibitors. Methods and Protocols. Humana Press; Chapters 1 and 2, pp. 1-44.
Latteyer, S. et al. (Mar. 2016) "A 6-Base Pair in Frame Germline Deletion in Exon 7 of RET Leads to Increased RET Phosphorylation, ERK Activation, and MEN2A" J Clin Endocrinol Metab, 101(3):1016-1022.
Le Rolle, A. et al. (2015) "Identification and characterization of RET fusions in advanced colorectal cancer" Oncotarget, 6(30):28929-28937.
Lee, M.S. et al. (2016) "Efficacy of the combination of MEK and CDK4/6 inhibitors in vitro and in vivo in KRAS mutant colorectal cancer models" Oncotarget, 7(26):39595-39608.
Lehar, J. et al. (2009) "Synergistic drug combinations improve therapeutic selectivity" Nat Biotechnol, 27(7):659-666. HHS Public Access Author Manuscript; available in PMC Jan. 1, 2010 (23 pages).
Lin, J.J. et al. (2016) "Clinical Activity of Alectinib in Advanced RET-Rearranged Non-Small Cell Lung Cancer" J Thorac Oncol, 11(11):2027-2032.
Lipson, D. et al. (2012) "Identification of new ALK and RET gene fusions from colorectal and lung cancer biopsies" Nat Med, 18(3):382-384. HHS Public Access Author Manuscript; available in PMC Feb. 6, 2014 (7 pages).
Machens, A et al. (2003) "Early Malignant Progression of Hereditary Medullary Thyroid Cancer" New Engl J Med, 349:1517-1525.
McMahon (2000) "VEGF Receptor Signaling in Tumor Angiogenesis," The Oncologist 5(suppl 1):3-10.
Mologni, L. et al. (2010) "Synthesis, structure-activity relationship and crystallographic studies of 3-substituted indolin-2-one RET inhibitors" Bioorg Med Chem, 18:1482-1496.
Mologni, L. et al. (2013) "Ponatinib is a potent inhibitor of wild-type and drug-resistant gatekeeper mutant RET kinase" Mol Cell Endocrinol, 377:1-6.
Mologni, L. et al. (2017) "RET kinase inhibitors: a review of recent patents (2012-2015)" Exp Opin Ther Patents, 27(1):91-99.
Moura, M.M. et al. (2009) "Correlation of RET somatic mutations with clinicopathological features in sporadic medullary thyroid carcinomas" Br J Cancer, 100:1777-1783.
Mulligan, L.M. (Mar. 2014) "RET revisited: expanding the oncogenic portfolio" Nat Rev Cancer, 14:173-186.
Mulligan, L.M. et al. (1995) "Genotype-phenotype correlation in multiple endocrine neoplasia type 2: report of the International RET Mutation Consortium" J Int Med, 238:343-346.
Mulligan, L.M. et al. (Jun. 3, 1993) "Germ-line mutations of the RET proto-oncogene in multiple endocrine neoplasia type 2A" Nature, 363:458-460.

(56) References Cited

OTHER PUBLICATIONS

NCT03037385, entitled "Phase 1 Study of BLU-667 in Patients With Thyroid Cancer, Non-Small Cell Lung Cancer, and OtherAdvanced Solid Tumors," ClinicalTrials.gov, Jan. 17, 2018 (8 pages).
NCT03037385, entitled "Phase 1 Study of BLU-667 in Patients With Thyroid Cancer, Non-Small Cell Lung Cancer, and OtherAdvanced Solid Tumors," ClinicalTrials.gov, Jan. 27, 2017 (7 pages).
NCT03037385, entitled Phase ½Study of the Highly-selective RET Inhibitor, Pralsetinib (BLU- 667), in Patients With Thyroid Cancer, Non-Small Cell Lung Cancer, and Other Advanced Solid Tumors (ARROW) (13 pages).
NCT04222972, entitled AcceleRET Lung Study of Pralsetinib for 1L RET Fusion-positive, Metastatic NSCLC (11 pages).
Oxnard, G.R. et al. "Assessment of Resistance Mechanisms and Clinical Implications in Patients With EGFR T790M-Positive Lung Cancer and Acquired Resistance to Osimertinib." JAMA Oncol. 2018, 4(11), pp. 1527-1534.
Pharmaceutical Dosage Forms: Tablets.—3rd ed., vol. 2 /edited by Larry L. Augsburger, Stephen W. Hoag, 2008, Chapter 6 (38 pages).
Pinedo (2000) Translational Research: The Role of VEGF in Tumor Angiogenesis, The Oncologist 5(suppl 1):1-2.
Piotrowska et al (2018) "MA26.03 Activity of Osimertinib and the Selective RET Inhibitor BLU-667 in an EGFR-Mutant Patient with Acquired RET Rearrangement," Journal of Thoracic Oncology—IASLC 19th World Conference on Lung Cancer, Sep. 23, 2018, pages S451-S451.
Piotrowska et al. (2018) "Landscape of Acquired Resistance to Osimertinib in EGFR-Mutant NSCLC and Clinical Validation of Combined EGFR and RET Inhibition with Osimertinib and BLU-677 for Acquired RET Fusion," Cancer Discovery 8(12):1529-1539.
Pirker, R. and M. Filipits (2015) "Alectinib in RET-rearranged non-small cell lung cancer—Another progress in precision medicine?" Transl Lung Cancer Res, 4(6):797-800.
Plaza-Menacho, I. et al. (2014) "Mechanisms of RET signaling in cancer: Current and future implications for targeted therapy" Cellular Signalling, 26:1743-1752.
Pound et al. "Is it possible to overcome issues of external validity in preclinical animal research? Why most animal models are bound to fail", J. Transl Med, Jan. 1, 2018 (Jan. 1, 2018), pp. 1-8, XP093000231, DOI: 10.1186/s12967-018-1678-1 Retrieved from the Internet: URL:https://www.researchgate.net/publication/328793141_1s_it_possible_to_overcome_issues_of_external_validity_in_preclinical_animal_research_Why_most_animal_models_are_bound_to_fail [retrieved on Nov. 21, 2022].
Qi, X. et al. (2015) "RET mutation p.S891A in a Chinese family with familial medullary thyroid carcinoma and associated cutaneous amyloidosis binding OSMR variant p.G513D" Oncotarget, 6(32):33993-34003.
Rahal, R. (Apr. 18, 2016) "The development of potent, selective RET inhibitors" Slides of a Presentation at the American Association for Cancer Research (AACR) Annual Meeting, Apr. 16-20, 2016, New Orleans (15 pages).
Rahal, R. et al. "BLU-667 is a Potent and Highly Selective RET Inhibitor Being Developed for RET—Driven Cancers," Poster B151, Blueprint Medicines Corporation (1 page).
Rahal, R. et al. (2016) "The development of potent, selective RET inhibitors that target both wild-type RET and prospectively identified resistance mutations to multi-kinase inhibitors" Abstract submitted to the American Association for CancerResearch (AACR) Annual Meeting, Apr. 16-20, 2016, New Orleans; submission date Dec. 1, 2015 (2 pages).
Ramalingam et al. "Osimertinib As First-Line Treatment of EGFR Mutation-Positive Advanced Non-Small-Cell Lung Cancer" Journal of Clinical Oncology, Mar. 20, 2018, vol. 36, No. 9, p. 841-849; abstract.
Reagan-Shaw et al. (2007) "Dose translation from animal to human studies revisited" The FASEB Journal, 22:659-661.
Reckamp et al. (2014) "Phase II trial of XL184 (cabozantinib) plus erlotinib in patients (pts) with advanced EGFR-mutant non-small cell lung cancer (NSCLC) with progressive disease (PD) on epidermal growth factor receptor (EGFR) tyrosine kinase inhibitor (TKI) therapy: A California Cancer Consortium phase II trial (NCI 9303)," *Journal of Clinical Oncology* 32(15)8014 4 pages.
Reckamp, K. L. et al. "Abstract 936: Analysis of cell-free DNA from 32,991 advanced cancers reveals novel co-occurring activating RET alterations and oncogenic signaling pathway aberrations." Cancer Research. Pubished Jul. 2018. Proceedings: AACR Annual Meeting 2018; Apr. 14-18, 2018; Chicago, IL. Retrieved from the internet URL: "<https://cancerres.aacrjournals.org/content/78/13 Supplement/936>" (3 pages).
Robinett, R.G. et al. (2007) "The discovery of substituted 4-(3-hyroxyanilino)-quinolines as potent RET kinase inhibitors" Bioorg Med Chem Lett, 17:5886-5893.
Robinson B. G. et al. "Vandetanib (100 mg) in Patients with Locally Advanced or Metastatic Hereditary Medullary Thyroid Cancer," Journal of Clinical En Doc Ri No Logy and Metabolism, vol. 95, No. 6, Jun. 1, 2010 (Jun. 1, 2010), pp. 2664-2671, XP055599340.
Romei, C. et al. (Apr. 2016) "A comprehensive overview of the role of the RET proto-oncogene in thyroid carcinoma" Nat Rev Endocrinol, 12:192-202.
Saito, M. et al. (Jun. 2016) "Gene aberrations for precision medicine against lung adenocarcinoma" Cancer Sci, 107(6):713-720.
Sarker, D. and P. Workman (2007) "Pharmacodynamic Biomarkers for Molecular Cancer Therapeutics" Adv Cancer Res, 96:213-268.
Schrock, A.B. et al. "Receptor Tyrosine Kinase Fusions and BRAF Kinase Fusions are Rare but Actionable Resistance Mechanisms to EGFR Tyrosine Kinase Inhibitors." Translational Oncology, 2018, 13 (9) pp. 1312-1323.
Scollo, C. et al. (2016) "A novel RET gene mutation in a patient with apparently sporadic pheochromocytoma" Endocr J, 63(1):87-91.
Sentürk et al. (2020) "Quantitative bioanalytical assay for the selective RET inhibitors selpercatinib and pralsetinib in mouse plasma and tissue homogenates using liquid chromatography-tandem mass spectrometry." Journal of Chromatography B 1147:122131 8 pages.
Silva, A.L. et al. (2015) "Identification and characterization of two novel germline RET variants associated with medullary thyroid carcinoma" Endocrine, 49:366-372.
Stransky, N. et al. (2014) "The landscape of kinase fusions in cancer" Nat Commun, 5:4846 (10 pages).
Subbiah et al. "Clinical activity and safety of the RET inhibitor pralsetinib in patients with RET fusion-positive solid tumours: update from the ARROW trial", ASCO, Jun. 4, 2021 (Jun. 4, 2021), pp. 1-1, XP093000210, Retrieved from the Internet: URL:https://ascopubs.org/doi/abs/10.1200/JCO.2021 .39.15_suppl.3079 [retrieved on Nov. 21, 2022].
Subbiah et al. Abstract CT043 "Highly potent and selective RET inhibitor, BLU-667, achieves proof of concept in a phase I study of advanced, RET-altered solid tumors," Cancer Research vol. 78, No. 13, Supplement Jul. 1, 2018 (Jul. 2018), XP002792435, Proceedings: AACR Annual Meeting 2018; Apr. 14-18, 2018; Chicago, IL. Retrieved from the Internet: URL:http://cancerres.aacrjournals.org/content/78/13Supplement/CT043 [retrieved on Jun. 26, 2019].
Subbiah V. et al. "Precision Targeted Therapy with BLU-667 for RET-Driven Cancers," Cancer Discovery, vol. 8, No. 7, Apr. 15, 2018 (pp. 836-849).
Subbiah, V. et al. (Jul. 2015) "Systemic and CNS activity of the RET inhibitor vandetanib combined with the mTOR inhibitor everolimus in KIF5B-RET re-arranged Non-Small Cell Lung Cancer with brain metastases" Lung Cancer, 89(1):76-79. HHS Public Access Author Manuscript; available in PMC Aug. 25, 2016 (10 pages).
Suehara, Y. et al. (Dec. 15, 2012) "Identification of KIF5B-RET and GOPC-ROS1 fusions in lung adenocarcinomas through a comprehensive mRNA-based screen for tyrosine kinase fusions" Clin Cancer Res, 18(24):6599-6608. HHS Public Access AuthorManuscript; available in PMC Nov. 17, 2014 (18 pages).
Suzuki, M. et al. (Jul. 2013) "Identification of a lung adenocarcinoma cell line with CCDC6-RET fusion gene and the effect of RET inhibitors in vitro and in vivo" Cancer Sci, 104(7):896-903.
Takeuchi, K. et al. (Mar. 2012) "RET, ROS1 and ALK fusions in lung cancer" Nat Med, 18(3):378-381.

(56) References Cited

OTHER PUBLICATIONS

Tan, D.S. et al. (2009) "Biomarker-Driven Early Clinical Trials in Oncology" Cancer J, 15(5):406-420.
Thackaberry et al. (2012) "Non-clinical toxicological considerations for pharmaceutical salt selection," Expert Opin. Drug Metab. Toxicol. 8(11):1419-1433.
Touat, M. et al. (2015) "Targeting FGFR Signaling in Cancer" Clin Cancer Res, 21(12):2684-2694.
U.S. Nat'l Library of Med., A Phase 1 Trial of Vandetanib (a Multi-kinase Inhibitor of EGFR, VEGFR and RET Inhibitor) in Combination With Everolimus (an mTOR Inhibitor) in Advanced Cancer, ClinicalTrials.gov,https://clinicaltrials.gov/ct2/show/NCT01582191 (last updated Jul. 3, 2018) (7 pages).
U.S. Nat'l Library of Med., Phase 1 Study of the Highly-selective RET Inhibitor BLU-667 in Patients With Thyroid Cancer, Non-Small Cell Lung Cancer, and Other Advanced Solid Tumors, ClinicalTrials.gov, https://clinicaltrials.gov/ct2/show/NCT03037385(last updated Jun. 27, 2018) (8 pages).
Wakelee et al. (2017) "A phase Ib/II study of cabozantinib (XL184) with or without erlotinib in patients with non-small cell lung cancer," Cancer Chemother Pharmacol 79:923-932.
Wang, L. et al. (2012) "Identification of a Novel, Recurrent HEY1-NCOA2 Fusion in Mesenchymal Chondrosarcoma based on a Genome-wide Screen of Exon-level Expression Data" Genes Chromosomes Cancer, 51(2):127-139. HHS Public Access Author Manuscript; available in PMC Feb. 1, 2013 (24 pages).
Wang, R. et al. (Dec. 10, 2012) "RET Fusions Define a Unique Molecular and Clinicopathologic Subtype of Non-Small-Cell Lung Cancer" J Clin Oncol, 30(35):4352-4359.
Wells, S.A. et al. (2015) "Revised American Thyroid Association Guidelines for the Management of Medullary Thyroid Carcinoma" Thyroid, 25(6):567-610.

* cited by examiner

Solid State Pharma Inc.: SSPI STAR° SV 16.00

PRALSETINIB PHARMACEUTICAL COMPOSITIONS

CROSS-REFERENCE TO RELATED APPLICATIONS

This application is a U.S. National Stage Application of International Patent Application No. PCT/US2021/034811, filed on May 28, 2021, which claims the benefit of and priority to U.S. Provisional Patent Application No. 63/032,030, filed on May 29, 2020, the disclosure of each of which is hereby incorporated by reference in its entirety for all purposes.

BACKGROUND

Pralsetinib is disclosed as one of many RET inhibitor compounds in patent publication WO2017/079140. A clinical trial (NCT03037385), entitled "Phase 1/2 Study of the Highly-selective RET Inhibitor, Pralsetinib (BLU-667), in Patients with Thyroid Cancer, Non-Small Cell Lung Cancer, and Other Advanced Solid Tumors (ARROW)" in underway. Pralsetinib is a potent and selective RET inhibitor provided in an oral dosage form to selectively target oncogenic RET alterations in certain cancer patients, including patients having a cancer harboring the most prevalent RET fusions and certain RET activating mutations. Pralsetinib can also be referred to as: (cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide, and has the following chemical structure:

(I)

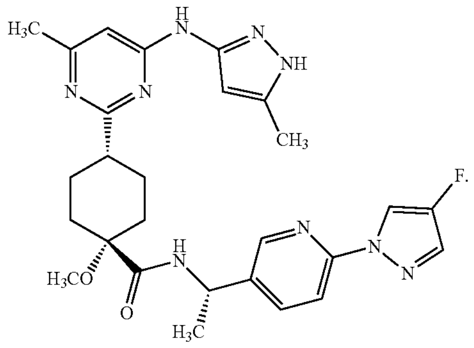

However, pralsetinib has a low aqueous solubility and as such, there remains a need for pharmaceutical compositions of pralsetinib that not only enhance its aqueous solubility but also to provide immediate release upon administration.

SUMMARY

The present invention features pharmaceutical compositions comprising 1) an amorphous solid dispersion comprising pralsetinib, or a pharmaceutically acceptable salt thereof, and a pharmaceutically acceptable hydrophilic polymer; and 2) an effervescent couple.

In one aspect, provided herein is a pharmaceutical composition comprising 1) an amorphous solid dispersion comprising pralsetinib, or a pharmaceutically acceptable salt thereof, and a pharmaceutically acceptable amphiphilic polymer; and 2) an effervescent couple.

In one aspect, provided herein is a pharmaceutical composition comprising 1) an amorphous solid dispersion comprising pralsetinib, or a pharmaceutically acceptable salt thereof, and a pharmaceutically acceptable hydrophilic and amphiphilic polymer; and 2) an effervescent couple.

In one embodiment, the invention features an oral dosage form comprising (a) an amorphous solid dispersion of pralsetinib, or a pharmaceutically acceptable salt thereof; and hydroxypropyl methylcellulose (HPMC); (b) a diluent; (c) sodium bicarbonate; (d) citric acid; (e) a moisture scavenger; and (f) a lubricant.

In one embodiment, the invention features an oral dosage form comprising (a) an amorphous solid dispersion of pralsetinib, or a pharmaceutically acceptable salt thereof; and hydroxypropyl methylcellulose (HPMC); (b) a diluent; (c) sodium bicarbonate; (d) citric acid; and (e) a lubricant.

In one embodiment, the invention features an oral dosage form comprising (a) an amorphous solid dispersion of pralsetinib, or a pharmaceutically acceptable salt thereof; and hydroxypropyl methylcellulose acetate succinate (HPMCAS); (b) a diluent; (c) sodium bicarbonate; (d) citric acid; (e) a moisture scavenger; and (f) a lubricant.

In one embodiment, the invention features an oral dosage form comprising (a) an amorphous solid dispersion of pralsetinib, or a pharmaceutically acceptable salt thereof; and hydroxypropyl methylcellulose (HPMC); (b) microcrystalline cellulose (MCC); (c) pregelatinized starch; (d) sodium bicarbonate; (e) citric acid; and (f) magnesium stearate.

In one embodiment, the invention features an oral dosage form comprising (a) an amorphous solid dispersion of pralsetinib, or a pharmaceutically acceptable salt thereof; and hydroxypropyl methylcellulose (HPMC); (b) microcrystalline cellulose (MCC); (c) sodium bicarbonate; (d) citric acid; and (e) magnesium stearate.

Another embodiment of the invention features a method for preparing the amorphous solid dispersion as described herein, comprising: dissolving the pralsetinib or the pharmaceutically acceptable salt thereof, with a hydrophilic polymer, e.g., in a 1:1 ratio, using a suitable manufacturing method so as to achieve an amorphous solid dispersion.

Also provided herein is a method for preparing the amorphous solid dispersion as described herein, comprising: dissolving the pralsetinib or the pharmaceutically acceptable salt thereof, with an amphiphilic polymer, e.g., in a 1:1 ratio, using a suitable manufacturing method so as to achieve an amorphous solid dispersion.

The amorphous solid dispersion can be prepared by hot melt extrusion, lyophilization, spray drying, solvent casting, or melt quenching. One embodiment of the invention uses a spray drying with a suitable solvent as a method of manufacture (e.g., adding a suitable solvent and removing the solvent by heating).

Another embodiment of the invention features a method of treating a RET-altered cancer comprising administering to a patient in need thereof a therapeutically effective amount of the compositions and oral dosage forms disclosed herein.

Another embodiment of the invention features a method of treating a patient with rearranged during transfection (RET)-positive locally advanced or metastatic non-small cell lung cancer (NSCLC) comprising administering to a patient in need thereof a therapeutically effective amount of the compositions and oral dosage forms disclosed herein. In a particular aspect, the (RET)-positive locally advanced or metastatic non-small cell lung cancer (NSCLC) is detected by an FDA approved test.

Another embodiment of the invention features a method of treating a patient with RET-mutation positive locally advanced or metastatic medullary thyroid cancer (MTC) comprising administering to the patient in need thereof a therapeutically effective amount of the compositions and oral dosage forms disclosed herein. In a particular aspect, the patients are 12 years of age and older.

Another embodiment of the invention features a method of treating a patient with RET-fusion positive locally advanced or metastatic thyroid cancer who require systemic therapy and have no satisfactory alternative treatment options comprising administering to the patient in need thereof a therapeutically effective amount of the compositions and oral dosage forms disclosed herein. In a particular aspect, the patients are 12 years of age and older.

DETAILED DESCRIPTION

Figure 1A:
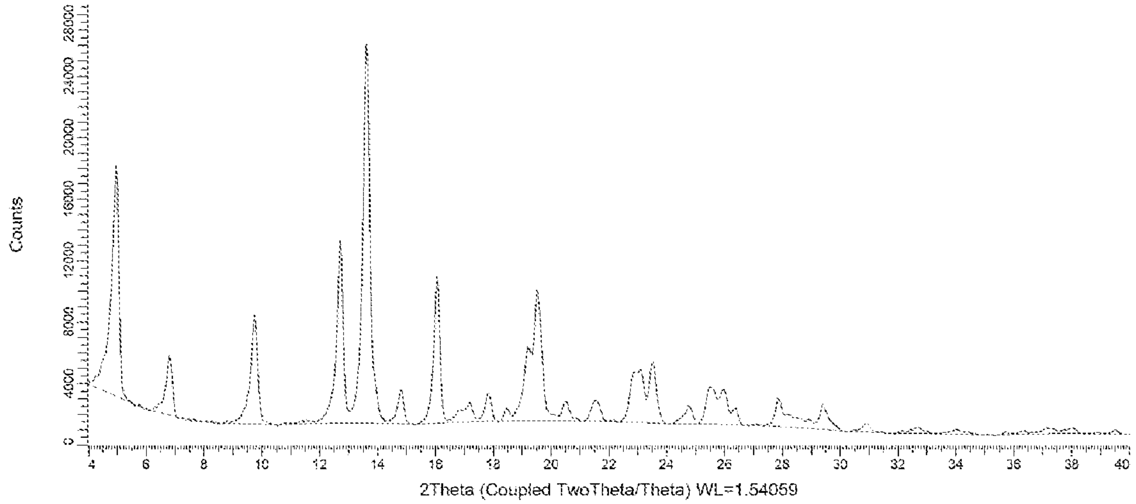
FIG. 1A is an X-ray powder diffraction pattern (XRPD) pattern of pralsetinib Form A.

Pralsetinib is a potent kinase inhibitor but has low aqueous solubility. To enhance the bioavailability of a poorly water soluble active pharmaceutical ingredient (API) such as pralsetinib, the API can be molecularly dispersed into a polymer matrix system, creating a solid dispersion. While dissolving the API in a polymer improves overall solubility, depending on the polymer matrix, it can delay the onset of API dissolution since the API needs to be released from the matrix. This delay causes formulation challenges if the composition is intended for immediate release. Disintegration agents, which promote disintegration through, for example, wicking, swelling and or strain recovery are commonly added to solid oral dosage forms to promote the break-up of the tablet, capsule, granule or powder matrix increasing the rate of release of the API. However, depending on the content of the matrix, not all types of disintegration agents will sufficiently break-up the matrix to support the immediate release of the API.

Pralsetinib is a potent kinase inhibitor but has low aqueous solubility. To enhance the solubility of pralsetinib, it was molecularly dispersed into a polymer matrix system. While embedding in the matrix system improved the solubility of pralsetinib, it also slowed its rate of release due to the hydration, swelling and or gelling of the polymer matrix, resulting in a diffusive release mechanism. The slowed release rate presented a challenge for formulating an immediate release dosage form. Conventional super disintegration agents (e.g, crospovidone, croscarmellose sodium, and sodium starch glycolate) that work to break up the matrix by swelling did not effectively break up the pralsetinib-polymer matrix. Surprisingly, the addition of an effervescent couple was able to effectively break-up the matrix, allowing for the release of pralsetinib at a rate suitable for an immediate release solid oral dosage form.

Pharmaceutical Compositions

The present invention features pharmaceutical compositions comprising 1) an amorphous solid dispersion comprising pralsetinib, or a pharmaceutically acceptable salt thereof, and a pharmaceutically acceptable hydrophilic polymer; and 2) an effervescent couple.

The present invention features pharmaceutical compositions comprising 1) an amorphous solid dispersion comprising pralsetinib, or a pharmaceutically acceptable salt thereof, and a pharmaceutically acceptable amphiphilic polymer; and 2) an effervescent couple.

The present invention features pharmaceutical compositions comprising 1) an amorphous solid dispersion comprising pralsetinib, or a pharmaceutically acceptable salt thereof, and a pharmaceutically acceptable hydrophilic and amphiphilic polymer; and 2) an effervescent couple.

Pralsetinib, or (cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide (or "Compound (I)") as shown below, can be prepared as a solid form of the free base or in a variety of salt forms:

(I)

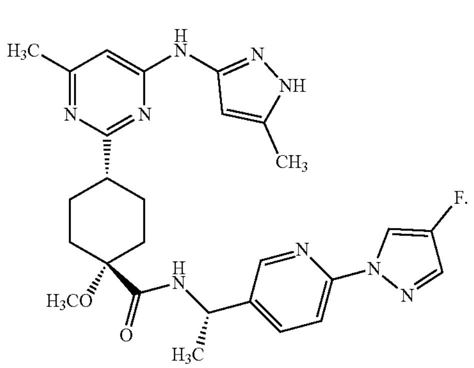

Pralsetinib can also be referred to as CAS No.: 2097132-94-8. Pralsetinib is a clinical-stage, highly potent and selective inhibitor of oncogenic RET fusion and activating mutation. In vivo, pralsetinib potently inhibits growth of NSCLC and thyroid cancer xenografts driven by various RET mutations and fusions without inhibiting VEGFR2.

A "hydrophilic polymer" is a polymer which dissolves in, or is swollen by, water. An "amphiphilic polymer" is a polymer containing both a hydrophobic and hydrophilic component. Hydrophilic polymers and/or amphiphilic polymers suitable for use in an amorphous solid dispersion of the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs), including polyvinyl graph coploymer; or any mixture thereof. In one aspect, the polymer is hydroxypropyl methylcellulose (or hypromellose), hydroxypropyl methylcellulose acetate succinate (HPMC-AS), hydroxypropylmethylcellulose E5 (HPMC-E5), hydroxypropylmethylcellulose E3 (HPMC-E3), vinylpyrrolidone-vinyl acetate copolymer (KOLLIDON VA64 or KOLLIDON K30), dimethylaminoethyl methacrylate-copolymer (EUDRAGIT EPO), poly(ethylene) oxide (POLYOX), or polyvinyl caprolactam-polyvinyl acetate-polyethylene glycol graft copolymer (SOLUPLUS). HPMC E3 refers to hydroxypropylmethylcellulose having a viscosity of about 2.4-3.6 mPa s, (2% in water)). HPMC E5 refers to hydroxypropylmethylcellulose having a viscosity of about 4 to 6 mPa s (2% in water). In a particular aspect, the hydrophilic polymer is hydroxypropyl methylcellulose. In a particular aspect, the hydrophilic polymer is hydroxypropyl methylcellulose E5 or hydroxypropyl methylcellulose E3.

Unless otherwise indicated, all numbers expressing quantities of ingredients, reaction conditions, data points (e.g., temperature, angles, etc.) and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

In one aspect, the pralsetinib, or an equivalent amount of a pharmaceutically acceptable salt thereof, and the hydrophilic polymer are in a weight percent ratio of about 1:1, for example, a disclosed composition may include about 100 mg pralsetinib and about 100 mg hydrophilic polymer such as disclosed herein. In another aspect, the pralsetinib, or an equivalent amount of a pharmaceutically acceptable salt thereof, and the amphiphilic polymer are in a weight percent ratio of about 1:1, for example, a disclosed composition may include about 100 mg pralsetinib and about 100 mg polymer such as disclosed herein. In another aspect, the pralsetinib, or an equivalent amount of a pharmaceutically acceptable salt thereof, and the hydrophilic polymer are in a weight percent ratio of from about 1:5 to about 5:1. In another aspect, the pralsetinib, or an equivalent amount of a pharmaceutically acceptable salt thereof, and the amphiphilic polymer are in a weight percent ratio of from about 1:5 to about 5:1.

In one aspect, a composition or an oral dosage form as described herein comprises the amorphous solid dispersion from about 25% to about 75% by weight of the composition or the oral dosage form, based on the total weight of the composition or the oral dosage form. In one aspect, a composition or an oral dosage form as described herein comprises the amorphous solid dispersion from about 25% to about 65% by weight of the composition or the oral dosage form, based on the total weight of the composition or the oral dosage form. In another aspect, a composition or an oral dosage form as described herein comprises the amorphous solid dispersion from about 25% to about 35% by weight of the composition or the oral dosage form, based on the total weight of the composition or the oral dosage form. In another aspect, a composition or an oral dosage form as described herein comprises the amorphous solid dispersion from about 35% to about 45% by weight of the composition or the oral dosage form, based on the total weight of the composition or the oral dosage form. In another aspect, a composition or an oral dosage form as described herein comprises the amorphous solid dispersion from about 45% to about 55% by weight of the composition or the oral dosage form, based on the total weight of the composition or the oral dosage form. In another aspect, a composition or an oral dosage form as described herein comprises the amorphous solid dispersion from about 55% to about 65% by weight of the composition or the oral dosage form, based on the total weight of the composition or the oral dosage form. In another aspect, a composition or an oral dosage form as described herein comprises the amorphous solid dispersion from about 65% to about 75% by weight of the composition or the oral dosage form, based on the total weight of the composition or the oral dosage form. In another aspect, a composition or an oral dosage form as described herein comprises the amorphous solid dispersion from about 20% to about 30% by weight of the composition or the oral dosage form, based on the total weight of the composition or the oral dosage form. In another aspect, a composition or an oral dosage form as described herein comprises the amorphous solid dispersion from about 30% to about 40% by weight of the composition or the oral dosage form, based on the total weight of the composition or the oral dosage form. In another aspect, a composition or an oral dosage form as described herein comprises the amorphous solid dispersion from about 40% to about 50% by weight of the composition or the oral dosage form, based on the total weight of the composition or the oral dosage form. In another aspect, a composition or an oral dosage form as described herein comprises the amorphous solid dispersion from about 50% to about 60% by weight of the composition or the oral dosage form, based on the total weight of the composition or the oral dosage form. In another aspect, a composition or an oral dosage form as described herein comprises the amorphous solid dispersion from about 60% to about 70% by weight of the composition or the oral dosage form, based on the total weight of the composition or the oral dosage form. In another aspect, a composition or an oral dosage form as described herein comprises the amorphous solid dispersion from about 70% to about 75% by weight of the composition or the oral dosage form, based on the total weight of the composition or the oral dosage form. In another aspect, a composition or an oral dosage form as described herein comprises the amorphous solid dispersion about 25%, about 35%, about 45%, about 50%, about 55%, about 60%, about 65%, about 70%, or about 75% by weight of the composition or the oral dosage form, based on the total weight of the composition or the oral dosage form.

In one aspect, the amorphous solid dispersion is prepared by hot melt extrusion, lyophilization, spray drying, solvent casting, or melt quenching.

In one aspect, the effervescent couple comprises a water-soluble acid and a water-soluble base. In another aspect, the effervescent couple comprises a water-soluble base. In one aspect, the water-soluble acid includes but is not limited to citric acid, tartaric acid, fumaric acid, adipic acid, succinic acid, malonic acid, benzoic acid, oxalic acid, malic acid, and glutaric acid. In one aspect, the water-soluble base includes but is not limited to sodium bicarbonate, sodium carbonate, potassium bicarbonate, potassium carbonate and magnesium carbonate. In a particular aspect, the water-soluble acid is citric acid and the water-soluble base is sodium bicarbonate. In a particular aspect, the water-soluble acid is anhydrous citric acid and the water-soluble base is sodium bicarbonate.

In one aspect, a composition or an oral dosage form as described herein comprises the water-soluble acid from 0% to about 20% by weight of the composition or the oral dosage form, based on the total weight of the composition or the oral dosage form. In one aspect, a composition or an oral dosage form as described herein comprises the water-soluble acid from about 1% to about 20% by weight of the composition or the oral dosage form, based on the total weight of the composition or the oral dosage form. In one aspect, a composition or an oral dosage form as described herein comprises the water-soluble acid from about 1% to about 5% by weight of the composition or the oral dosage form, based on the total weight of the composition or the oral dosage form. In one aspect, a composition or an oral dosage form as described herein comprises the water-soluble acid from about 5% to about 10% by weight of the composition or the oral dosage form, based on the total weight of the composition or the oral dosage form. In one aspect, a composition or an oral dosage form as described herein comprises the water-soluble acid from about 10% to about 15% by weight of the composition or the oral dosage form, based on the total weight of the composition or the oral dosage form. In one aspect, a composition or an oral dosage form as described herein comprises the water-soluble acid from about 15% to about 20% by weight of the composition or the oral dosage form, based on the total weight of the composition or the oral dosage form. In one aspect, a composition or an oral dosage form as described herein comprises the water-soluble acid from about 3% to about 10% by weight of the composition or the oral dosage form, based on the total weight of the composition or the oral dosage form. In one aspect, a composition or an oral dosage form as described herein comprises the water-soluble acid from about 10% to about 20% by weight of the composition or the oral dosage form, based on the total weight of the composition or the oral dosage form. In one aspect, a composition or an oral dosage form as described herein comprises the water-soluble acid from about 5% to about 15% by weight of the composition or the oral dosage form, based on the total weight of the composition or the oral dosage form. In one aspect, a composition or an oral dosage form as described herein comprises the water-soluble acid about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight of the composition or the oral dosage form, based on the total weight of the composition or the oral dosage form.

In one aspect, a composition or an oral dosage form as described herein comprises the water-soluble base from about 1% to about 35% by weight of the composition or the oral dosage form, based on the total weight of the composition or the oral dosage form. In one aspect, a composition or an oral dosage form as described herein comprises the water-soluble base from about 1% to about 10% by weight of the composition or the oral dosage form, based on the total weight of the composition or the oral dosage form. In one aspect, a composition or an oral dosage form as described herein comprises the water-soluble base from about 10% to about 20% by weight of the composition or the oral dosage form, based on the total weight of the composition or the oral dosage form. In one aspect, a composition or an oral dosage form as described herein comprises the water-soluble base from about 20% to about 30% by weight of the composition or the oral dosage form, based on the total weight of the composition or the oral dosage form. In one aspect, a composition or an oral dosage form as described herein comprises the water-soluble base from about 30% to about 35% by weight of the composition or the oral dosage form, based on the total weight of the composition or the oral dosage form. In one aspect, a composition or an oral dosage form as described herein comprises the water-soluble base from about 10% to about 25% by weight of the composition or the oral dosage form, based on the total weight of the composition or the oral dosage form. In one aspect, a composition or an oral dosage form as described herein comprises the water-soluble base from about 12% to about 35% by weight of the composition or the oral dosage form, based on the total weight of the composition or the oral dosage form. In one aspect, a composition or an oral dosage form as described herein comprises the water-soluble base from about 20% to about 35% by weight of the composition or the oral dosage form, based on the total weight of the composition or the oral dosage form. In one aspect, a composition or an oral dosage form as described herein comprises the water-soluble base about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight of the composition or the oral dosage form, based on the total weight of the composition or the oral dosage form.

In a particular aspect, a composition or an oral dosage form as described herein comprises the water-soluble acid from about 5% to about 15% by weight of the composition or the oral dosage form, based on the total weight of the composition or the oral dosage form, and the water-soluble base from about 12% to about 35% by weight of the composition or the oral dosage form, based on the total weight of the composition or the oral dosage form.

In one aspect, the composition further comprises a moisture scavenger. Non-limiting examples of suitable moisture include celluloses, celluloses derivatives, silica and silica derivatives. Specific examples are cellulose, microcrystalline cellulose, sodium carboxymethyl cellulose, hydroxypropyl cellulose, hydroxypropylmethyl cellulose, or a silica including a fumed silicon dioxide. Notably, the microcrystalline cellulose may be Avicel™ and/or the fumed silicon dioxide may be Cabosil™. In one aspect, the moisture scavenger is a starch. In a particular aspect, the starch is pregelatinized starch.

In one aspect, a composition or an oral dosage form as described herein comprises the moisture scavenger from 0% to about 30% by weight of the composition or the oral dosage form, based on the total weight of the composition or the oral dosage form. In another aspect, a composition or an oral dosage form as described herein comprises the moisture scavenger from about 0.5% to about 30% by weight of the composition or the oral dosage form, based on the total weight of the composition or the oral dosage form. In one aspect, a composition or an oral dosage form as described herein comprises the moisture scavenger from about 0.5% to about 5% by weight of the composition or the oral dosage form, based on the total weight of the composition or the oral dosage form. In one aspect, a composition or an oral dosage form as described herein comprises the moisture scavenger from about 5% to about 10% by weight of the composition or the oral dosage form, based on the total weight of the composition or the oral dosage form. In one aspect, a composition or an oral dosage form as described herein comprises the moisture scavenger from about 10% to about 15% by weight of the composition or the oral dosage form, based on the total weight of the composition or the oral dosage form. In one aspect, a composition or an oral dosage form as described herein comprises the moisture scavenger from about 15% to about 20% by weight of the composition or the oral dosage form, based on the total weight of the composition or the oral dosage form. In one aspect, a composition or an oral dosage form as described herein comprises the moisture scavenger from about 20% to about 25% by weight of the composition or the oral dosage form, based on the total weight of the composition or the oral dosage form. In one aspect, a composition or an oral dosage form as described herein comprises the moisture scavenger from about 25% to about 30% by weight of the composition or the oral dosage form, based on the total weight of the composition or the oral dosage form. In one aspect, a composition or an oral dosage form as described herein comprises the moisture scavenger from about 5% to about 15% by weight of the composition or the oral dosage form, based on the total weight of the composition or the oral dosage form. In one aspect, a composition or an oral dosage form as described herein comprises the moisture scavenger from about 2% to about 4% by weight of the composition or the oral dosage form, based on the total weight of the composition or the oral dosage form. In one aspect, a composition or an oral dosage form as described herein comprises the moisture scavenger about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight of the composition or the oral dosage form, based on the total weight of the composition or the oral dosage form. In an alternative aspect, the composition does not include a moisture scavenger.

In one aspect, the composition further comprises a diluent (also referred to as a filler). Non-limiting examples of suitable diluents are starch (e.g. cellulose, potato or corn starch), salts (e.g., calcium hydrogenphosphate, magnesium oxide), sugars like lactose (e.g, lactose monohydrate), silicates (e.g., silicium dioxide), talc, isomalt, or polyvinyl alcohol. In one aspect, the diluent is a cellulose. In a particular aspect, the diluent is microcrystalline cellulose (e.g., Avicel or specifically, Avicel PH-102).

In one aspect, a composition or an oral dosage form as described herein comprises the diluent from about 5% to about 70% by weight of the composition or the oral dosage form, based on the total weight of the composition or the oral dosage form. In another aspect, a composition or an oral dosage form as described herein comprises the diluent from about 5% to about 60% by weight of the composition or the oral dosage form, based on the total weight of the composition or the oral dosage form. In one aspect, a composition or an oral dosage form as described herein comprises the diluent from about 5% to about 10% by weight of the composition or the oral dosage form, based on the total weight of the composition or the oral dosage form. In one aspect, a composition or an oral dosage form as described herein comprises the diluent from about 10% to about 15% by weight of the composition or the oral dosage form, based on the total weight of the composition or the oral dosage form. In one aspect, a composition or an oral dosage form as described herein comprises the diluent from about 15% to about 20% by weight of the composition or the oral dosage form, based on the total weight of the composition or the oral dosage form. In one aspect, a composition or an oral dosage form as described herein comprises the diluent from about 20% to about 25% by weight of the composition or the oral dosage form, based on the total weight of the composition or the oral dosage form. In one aspect, a composition or an oral dosage form as described herein comprises the diluent from about 25% to about 30% by weight of the composition or the oral dosage form, based on the total weight of the composition or the oral dosage form. In one aspect, a composition or an oral dosage form as described herein comprises the diluent from about 30% to about 35% by weight of the composition or the oral dosage form, based on the total weight of the composition or the oral dosage form. In one aspect, a composition or an oral dosage form as described herein comprises the diluent from about 35% to about 40% by weight of the composition or the oral dosage form, based on the total weight of the composition or the oral dosage form. In one aspect, a composition or an oral dosage form as described herein comprises the diluent from about 40% to about 45% by weight of the composition or the oral dosage form, based on the total weight of the composition or the oral dosage form. In one aspect, a composition or an oral dosage form as described herein comprises the diluent from about 45% to about 50% by weight of the composition or the oral dosage form, based on the total weight of the composition or the oral dosage form. In one aspect, a composition or an oral dosage form as described herein comprises the diluent from about 50% to about 55% by weight of the composition or the oral dosage form, based on the total weight of the composition or the oral dosage form. In one aspect, a composition or an oral dosage form as described herein comprises the diluent from about 55% to about 60% by weight of the composition or the oral dosage form, based on the total weight of the composition or the oral dosage form. In one aspect, a composition or an oral dosage form as described herein comprises the diluent from about 60% to about 65% by weight of the composition or the oral dosage form, based on the total weight of the composition or the oral dosage form. In one aspect, a composition or an oral dosage form as described herein comprises the diluent from about 65% to about 70% by weight of the composition or the oral dosage form, based on the total weight of the composition or the oral dosage form. In one aspect, a composition or an oral dosage form as described herein comprises the diluent about 5%, about 10%, about 15%, about 20%, about 25%, about 30%, about 35%, about 40%, about 45%, about 50%, about 55%, about 60%, or about 65%, or about 70% by weight of the composition or the oral dosage form, based on the total weight of the composition or the oral dosage form.

In one aspect, the composition further comprises a lubricant. Non-limiting examples of suitable lubricants include talc, calcium stearate, magnesium stearate, solid polyethylene glycols, sodium lauryl sulfate, sodium stearyl fumerate, and mixtures thereof. In a particular aspect, the lubricant is magnesium stearate.

In one aspect, a composition or an oral dosage form as described herein comprises the lubricant from about 0.1% to about 5% by weight of the composition or the oral dosage form, based on the total weight of the composition or the oral dosage form. In one aspect, a composition or an oral dosage form as described herein comprises the lubricant from about 0.1% to about 1% by weight of the composition or the oral dosage form, based on the total weight of the composition or the oral dosage form. In one aspect, a composition or an oral dosage form as described herein comprises the lubricant from about 1% to about 2% by weight of the composition or the oral dosage form, based on the total weight of the composition or the oral dosage form. In one aspect, a composition or an oral dosage form as described herein comprises the lubricant from about 2% to about 3% by weight of the composition or the oral dosage form, based on the total weight of the composition or the oral dosage form. In one aspect, a composition or an oral dosage form as described herein comprises the lubricant from about 3% to about 4% by weight of the composition or the oral dosage form, based on the total weight of the composition or the oral dosage form. In one aspect, a composition or an oral dosage form as described herein comprises the lubricant from about 4% to about 5% by weight of the composition or the oral dosage form, based on the total weight of the composition or the oral dosage form. In one aspect, a composition or an oral dosage form as described herein comprises the lubricant about 0.1%, about 0.5%, about 1%, about 1.5%, about 2%, about 2.5%, about 3%, about 3.5%, about 4%, about 4.5%, or about 5% by weight of the composition or the oral dosage form, based on the total weight of the composition or the oral dosage form.

In one embodiment, the invention features an oral dosage form comprising (a) an amorphous solid dispersion of pralsetinib, or a pharmaceutically acceptable salt thereof; and hydroxypropyl methylcellulose (HPMC); (b) microcrystalline cellulose (MCC); (c) pregelatinized starch; (d) sodium bicarbonate; (e) citric acid; and (f) magnesium stearate. In one aspect, the amount of the amorphous solid dispersion is as described above. In one aspect, the amount of the microcrystalline cellulose (MCC) is as described above for the diluent. In one aspect, the amount of the pregelatinized starch is as described above for the moisture scavenger. In one aspect, the amount of the sodium bicarbonate is as described above for the water-soluble base. In one aspect, the amount of the citric acid is as described above for the water-soluble acid. In one aspect, the amount of the magnesium stearate is as described above as for the lubricant.

In one aspect, the composition is prepared in an oral dosage form. An oral dosage form can be prepared into any suitable dosage forms, such as capsule, dragee, granule, powder, or tablet. In a particular aspect, the oral dosage form is a capsule. In a particular aspect, the oral dosage form is a tablet. In a particular aspect, the oral dosage form is for immediate release. Whether a composition or oral dosage form is an immediate release formulation can be ascertained based on methods known to one of skill in the art, for example USP standards.

As used herein, "the total weight of the oral dosage form" means the material within the oral dosage form (e.g., within a capsule) or the oral dosage form without any coating (e.g., without the tablet coating).

An oral dosage form can be prepared into any suitable dosage forms, such as capsule, dragee, granule, powder, or tablet. In a particular aspect, the oral dosage form is a capsule. In one embodiment, the size of the capsule is from size 4 to size 00. In another embodiment, the size of the capsule is from size 4 to size 0. In certain embodiments, the size of the capsule is from size 3 to size 0. In some embodiments, the size of the capsule is 0. In other embodiments, the size of the capsule is 00. In certain embodiments, the size of the capsule is 1. In some embodiments, the size of the capsule is 2. In other embodiments, the size of the capsule is 3. In certain embodiments, the size of the capsule is 4.

In one aspect, the oral dosage form or the composition as described herein comprises about 10 mg, about 20 mg, about 30 mg, about 40 mg, about 50 mg, about 60 mg, about 70 mg, about 80 mg, about 90 mg, about 100 mg, or about 200 mg of pralsetinib, or an equivalent amount of a pharmaceutically acceptable salt thereof. In some embodiments, the oral dosage form (e.g., tablet) comprises about 50 mg of pralsetinib or an equivalent amount of a pharmaceutically acceptable salt thereof.

In one aspect, the oral dosage form or the composition as described herein comprises about 110 mg, 120 mg, 130 mg, 140 mg, 150 mg, 200 mg, 300 mg, or 400 mg of pralsetinib, or an equivalent amount of a pharmaceutically acceptable salt thereof. In certain embodiments, the oral dosage form (e.g., tablet) comprises about 200 mg of pralsetinib or an equivalent amount of a pharmaceutically acceptable salt thereof.

In one aspect, the present disclosure provides an immediate release oral dosage form comprising:

a) an amorphous solid dispersion comprising: pralsetinib, or a pharmaceutically acceptable salt thereof, and hydroxypropyl methylcellulose E3, wherein the pralsetinib or an equivalent amount of a pharmaceutically acceptable salt thereof and the hydroxypropyl methyl cellulose E3 are in about a 1:1 weight ratio;
b) an effervescent couple comprising about 3 to about 13 w/w % citric acid and about 7 to about 30 w/w % sodium bicarbonate; wherein w/w % is based on the total weight of the oral dosage form;
c) a diluent; and optionally
d) moisture scavenger and/or a lubricant.

In some embodiments, the amorphous solid dispersion comprises about 30 mg, about 50 mg, about 60 mg, about 100 mg of pralsetinib or an equivalent amount of a pharmaceutically acceptable salt thereof.

In some embodiments, at least 50%, at least 60%, at least 70%, at least 75%, at least 80%, at least 85%, at least 90%, or at least 95%, of the pralsetinib is released in 45 minutes using USP) <711> with a Type 2 Apparatus, media containing 900 mL 0.1 M HCl, and a paddle speed of 100 rpm. In certain embodiments, at least 80% of the pralsetinib is released in 45 minutes using USP) <711> with a Type 2 Apparatus, media containing 900 mL 0.1 M HCl, and a paddle speed of 100 rpm. In certain embodiments, at least 85% of the pralsetinib is released in 45 minutes using USP) <711> with a Type 2 Apparatus, media containing 900 mL 0.1 M HCl, and a paddle speed of 100 rpm. In certain embodiments, at least 90% of the pralsetinib is released in 45 minutes using USP) <711> with a Type 2 Apparatus, media containing 900 mL 0.1 M HCl, and a paddle speed of 100 rpm. In certain embodiments, at least 95% of the pralsetinib is released in 45 minutes using USP) <711> with a Type 2 Apparatus, media containing 900 mL 0.1 M HCl, and a paddle speed of 100 rpm.

In certain embodiments, the dosage form is a capsule, wherein the capsule disintegrates in about 5 to 15 minutes (e.g., about 7 to 15 minutes, about 6 minutes, about 7 minutes, about 10 minutes, about 15 minutes) using USP <701>, with Basket Type A and a disk with a maintained temperature at 37° C.±2° C. In other embodiments, the dosage form is a capsule, wherein the capsule disintegrates in less than 15 minutes (e.g., less than 10 minutes, less than 5 minutes) using USP <701>, with Basket Type A and a disk with a maintained temperature at 37° C.±2° C.

In some embodiments, the dosage form is a capsule, wherein the capsule disintegrates in about 5 to about 15 minutes (e.g., about 7 to 15 minutes, e.g., about 6 minutes, about 7 minutes, about 10 minutes, about 15 minutes) using USP <701>, wherein the capsule is placed in each of the 6 tubes of the basket (Basket type A) along with the disc and analytical grade water is added, and the temperature is maintained at 37° C.±2° C.

In some embodiments, the dosage form is a capsule, wherein at least 50%, at least 60%, at least 70%, at least 75%, at least 80%, at least 85%, at least 90%, or at least 95%, of the pralsetinib is released in about 120 minutes or alternatively, 45 minutes, using USP II apparatus with a media containing 900 mL pH 6.8 sodium phosphate buffer with 0.5% CTAB and a paddle speed of 75 rpm±2 rpm.

In some embodiments, the dosage form is a capsule, wherein at least 80% of the pralsetinib is released in about 45 minutes using USP II apparatus with a media containing 900 mL pH 6.8 sodium phosphate buffer with 0.5% CTAB and a paddle speed of 75 rpm±2 rpm. In some embodiments, the dosage form is a capsule, wherein at least 85% of the pralsetinib is released in about 45 minutes using USP II apparatus with a media containing 900 mL pH 6.8 sodium phosphate buffer with 0.5% CTAB and a paddle speed of 75 rpm±2 rpm. In some embodiments, the dosage form is a capsule, wherein at least 90% of the pralsetinib is released in about 45 minutes using USP II apparatus with a media containing 900 mL pH 6.8 sodium phosphate buffer with 0.5% CTAB and a paddle speed of 75 rpm±2 rpm. In some embodiments, the dosage form is a capsule, wherein at least 95% of the pralsetinib is released in about 45 minutes using USP II apparatus with a media containing 900 mL pH 6.8 sodium phosphate buffer with 0.5% CTAB and a paddle speed of 75 rpm±2 rpm.

Another embodiment of the invention features a method for preparing the amorphous solid dispersion described herein, comprising: mixing the pralsetinib or the pharmaceutically acceptable salt thereof, with the hydrophilic polymer in about a 1:1 ratio; adding a solvent, and removing the solvent by heating.

Another embodiment of the invention features a method for preparing the amorphous solid dispersion described herein, comprising: mixing the pralsetinib or the pharmaceutically acceptable salt thereof, with the amphiphilic polymer in about a 1:1 ratio; adding a solvent, and removing the solvent by heating.

Solid Forms

Compound (I) can exist in an amorphous solid form or in different solid forms, or mixtures of solid forms, which can additionally include one or more equivalents of water (e.g., anhydrous or hydrate forms). As provided herein, pralsetinib is in an amorphous solid form. As provided herein, crystalline solid form(s) of Compound (I) can be identified by distinct XRPD peaks that are not characterized in previous disclosures of Compound (I). There are provided herein certain crystalline forms of Compound (I) and related methods for preparing and using these solid form materials. As provided herein, these crystalline forms of Compound (I) can be used to the prepare an amorphous solid dispersion containing pralsetinib and a hydrophilic polymer. As provided herein, these crystalline forms of Compound (I) can be used to the prepare an amorphous solid dispersion containing pralsetinib and an amphiphilic polymer.

When used alone, the term "Form A" refers to the crystalline polymorph Form A of pralsetinib. The terms "Form A", "Form A of pralsetinib", "Form A of ((cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide", or "Form A of Compound (I)" are used interchangeably. Form A can be characterized by, for example, XRPD alone or XRPD in combination with any one or more of DSC, DVS, and TGA. Form A is anhydrous.

When used alone, the term "Form B" refers to the crystalline polymorph Form B of pralsetinib. The terms "Form B", "Form B of pralsetinib", "Form B of ((cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide", or "Form B of Compound (I)" are used interchangeably. Form B can be characterized by, for example, XRPD alone or XRPD in combination with any one or more of DSC, DVS, and TGA. Form B is a dehydrate.

When used alone, the term "Form C" refers to the crystalline polymorph Form C of pralsetinib. The terms "Form C", "Form C of pralsetinib", "Form C of ((cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide", or "Form C of Compound (I)" are used interchangeably. Form C can be characterized by, for example, XRPD alone or XRPD in combination with any one or more of DSC, DVS, and TGA. Form C is a hydrate.

When used alone, the term "Form I" or "pralsetinib HCl salt Form I" refers to the crystalline polymorph Form I of the hydrochloride salt of pralsetinib. The terms "Form I", "Form I of the hydrochloride salt of pralsetinib", "Form I of the hydrochloride salt of ((cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide", or "Form I of the hydrochloride salt of Compound (I)" are used interchangeably. Form I can be characterized by, for example, XRPD alone or XRPD in combination with any one or more of DSC, DVS, and TGA.

When used alone, the term "Form II" or "pralsetinib HCl salt Form II" refers to the crystalline polymorph Form I of the hydrochloride salt of pralsetinib. The terms "Form II", "Form II of the hydrochloride salt of pralsetinib", "Form II of the hydrochloride salt of ((cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl) cyclohexanecarboxamide", or "Form II of the hydrochloride salt of Compound (I)" are used interchangeably. Form II can be characterized by, for example, XRPD alone or XRPD in combination with any one or more of DSC, DVS, and TGA.

When used alone, the term "Form III" or "pralsetinib HCl salt Form IIII" refers to the crystalline polymorph Form III of the hydrochloride salt of pralsetinib. The terms "Form III", "Form III of the hydrochloride salt of pralsetinib", "Form III of the hydrochloride salt of ((cis)-N—((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide", or "Form III of the hydrochloride salt of Compound (I)" are used interchangeably. Form III can be characterized by, for example, XRPD alone or XRPD in combination with any one or more of DSC, DVS, and TGA.

As used herein, "crystalline" refers to a solid having a crystal structure wherein the individual molecules have a highly homogeneous regular locked-in chemical configuration.

"Anhydrous" as used herein, means that the crystalline form comprises substantially no water in the crystal lattice e.g., less than 1% by weight as determined by Karl Fisher (KF), or less than 1% by weight as determined by another quantitative analysis.

As used herein, the term "hydrate" refers to a crystalline solid form containing Compound (I) and either stoichiometric or nonstoichiometric amounts of a water incorporated within the crystal structure. A "dehydrate" refers to a crystalline solid form containing Compound (I) in which the stoichiometric or nonstoichiometric amounts of a water incorporated within the crystal structure has been removed. Techniques known to one of skill in the art to determine the to determine the amount of water present include, for example, TGA and KF.

Solid state ordering of solids may be determined by standard techniques known in the art, e.g., by X-ray powder diffraction (XRPD), differential scanning calorimetry (DSC), thermal gravimetric analysis (TGA), dynamic vapor sorption (DVS), or vibrational spectroscopy. Amorphous solids can also be differentiated from crystalline solids e.g., by birefringence using polarized light microscopy. Amorphous solids consist of disordered arrangements of molecules and do not possess a distinguishable crystal lattice.

Relative intensity is calculated as a ratio of the peak intensity of the peak of interest versus the peak intensity of the largest peak. In certain embodiments, the relative intensity of the peaks may vary due to the preferred orientation of the sample. Preferred orientation in the specimen influences the intensities of various reflections so that some are more intense and others less intense, compared to what would be expected from a completely random specimen. In general, the morphology of many crystalline particles tends to give a specimen that exhibits some degree of preferred orientation in the specimen holder. This is particularly evident for needlelike or plate-like crystals when size reduction yields finer needles or platelets.

In some embodiments, Form A is at least 70%, 80%, 90%, 95%, 98%, 99%, 99.5%, or 99.9% pure. The purity of Form A is determined by dividing the weight of Form A of the Compound (I) in a composition comprising Compound (I) over the total weight of Compound (I) in the composition.

In some embodiments, Form B is at least 70%, 80%, 90%, 95%, 98%, 99%, 99.5%, or 99.9% pure. The purity of Form B is determined by dividing the weight of Form B of the Compound (I) in a composition comprising Compound (I) over the total weight of Compound (I) in the composition.

In some embodiments, Form C is at least 70%, 80%, 90%, 95%, 98%, 99%, 99.5%, or 99.9% pure. The purity of Form C is determined by dividing the weight of Form C of the Compound (I) in a composition comprising Compound (I) over the total weight of Compound (I) in the composition.

In some embodiments, Form I is at least 70%, 80%, 90%, 95%, 98%, 99%, 99.5%, or 99.9% pure. The purity of Form I is determined by dividing the weight of Form I of the Compound (I) in a composition comprising Compound (I) over the total weight of Compound (I) in the composition.

In some embodiments, Form II is at least 70%, 80%, 90%, 95%, 98%, 99%, 99.5%, or 99.9% pure. The purity of Form II is determined by dividing the weight of Form II of the Compound (I) in a composition comprising Compound (I) over the total weight of Compound (I) in the composition.

In some embodiments, Form III is at least 70%, 80%, 90%, 95%, 98%, 99%, 99.5%, or 99.9% pure. The purity of Form III is determined by dividing the weight of Form III of the Compound (I) in a composition comprising Compound (I) over the total weight of Compound (I) in the composition.

The crystalline forms disclosed in the present application, for example, Form A, Form B, Form C, Form I, Form II, and Form III have numerous advantages. In particular, the advantages of Form A, Form B, Form C, Form I, Form II, and Form III include ease of isolation, process reproducibility, suitability for large scale manufacturing process, etc.

In one aspect, the present disclosure provides crystalline Form A of pralsetinib.

In one aspect, crystalline Form A of pralsetinib is characterized by x-ray powder diffraction pattern. The x-ray powder diffraction pattern can be acquired using a Bruker D8 Advance as described herein. In one embodiment, crystalline Form A is characterized by at least three, at least four, or at least five x-ray powder diffraction peaks at 2-theta angles selected from 5.0±0.2°, 9.7±0.2°, 12.7±0.2°, 13.6±0.2°, and 16.1±0.2°.

Alternatively, crystalline Form A is characterized by at least three, at least four, at least five, at least six, at least seven, at least eight, or at least nine x-ray powder diffraction peaks at 2-theta angles selected from 5.0±0.2°, 6.8±0.2°, 9.7±0.2°, 12.7±0.2°, 13.6±0.2°, 16.1±0.2°, 19.2±0.2°, 19.5±0.2°, and 23.5±0.2°. Alternatively, crystalline Form A is characterized by x-ray powder diffraction peaks at 2-theta angles 5.0±0.2°, 6.8±0.2°, 9.7±0.2°, 12.7±0.2°, 13.6±0.2°, 16.1±0.2°, 19.2±0.2°, 19.5±0.2°, and 23.5±0.2°.

Alternatively, crystalline Form A is characterized by at least three, at least four, at least five, at least six, at least seven, at least eight, at least nine, or at least ten x-ray powder diffraction peaks at 2-theta angles selected from 5.0±0.2°, 6.8±0.2°, 9.7±0.2°, 12.7±0.2°, 13.6±0.2°, 14.8±0.2°, 16.1±0.2°, 17.2±0.2°, 17.8±0.2°, 19.2±0.2°, 19.5±0.2°, 20.5±0.2°, 21.6±0.2°, 23.1±0.2°, 23.5±0.2°, 24.8±0.2°, 25.6±0.2°, 26.0±0.2°, 27.9±0.2°, and 29.4±0.2°. In another alternative crystalline Form A is characterized by x-ray powder diffraction peaks at 2-theta angle 5.0±0.2°, 6.8±0.2°, 9.7±0.2°, 12.7±0.2°, 13.6±0.2°, 14.8±0.2°, 16.1±0.2°, 17.2±0.2°, 17.8±0.2°, 19.2±0.2°, 19.5±0.2°, 20.5±0.2°, 21.6±0.2°, 23.1±0.2°, 23.5±0.2°, 24.8±0.2°, 25.6±0.2°, 26.0±0.2°, 27.9±0.2°, and 29.4±0.2°. In some embodiments, the peaks described above for crystalline Form A have a relative intensity of at least 10%, of at least 15%, of at least 20%, or of at least 25%.

In another aspect, crystalline Form A of pralsetinib has an XRPD pattern that is substantially the same XRPD pattern shown in FIG. 1A.

In another aspect, crystalline Form A of pralsetinib has an XRPD pattern that substantially includes the peaks in Table 1A.

Figure 1B:
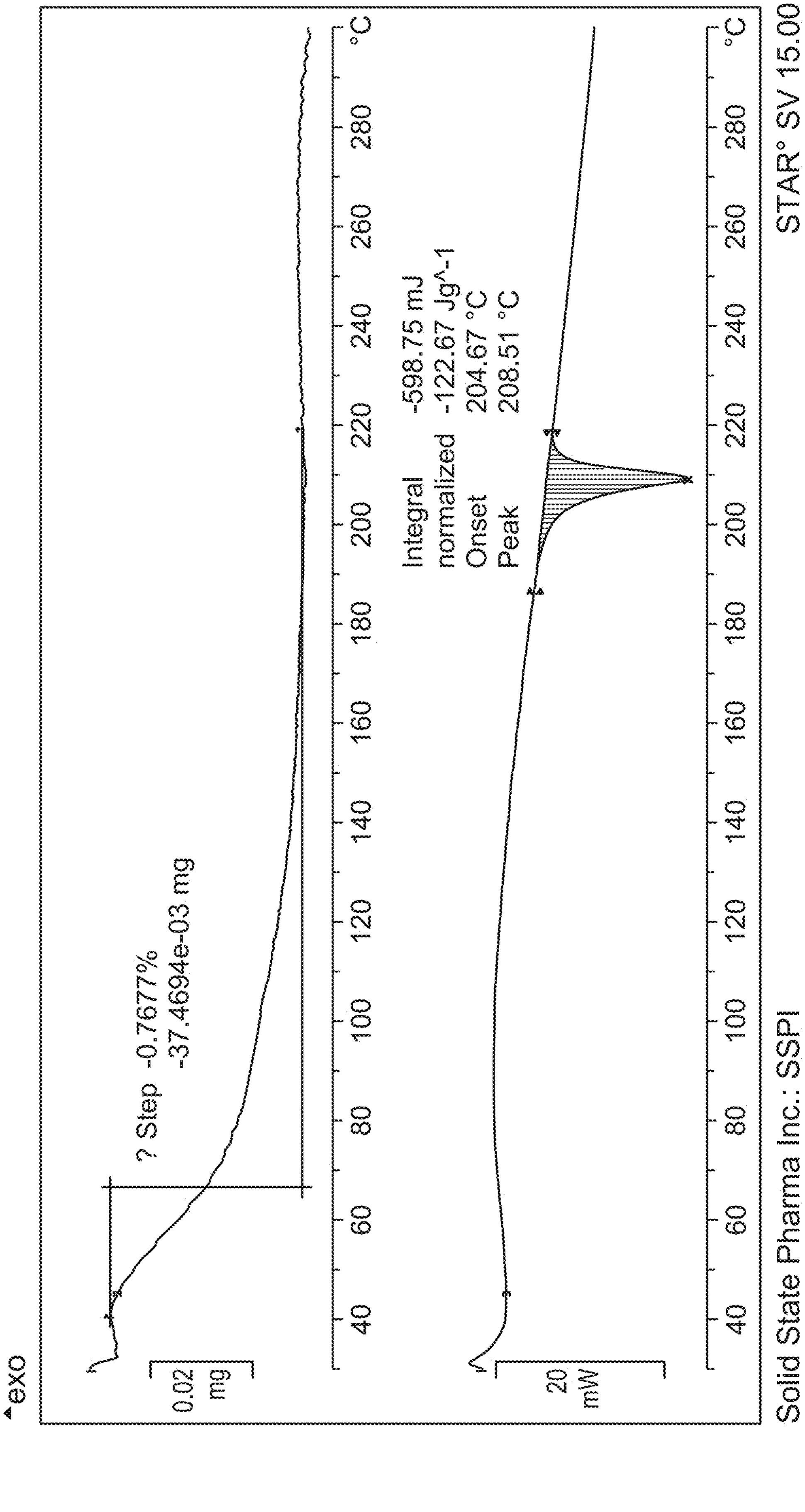
FIG. 1B shows DSC and TGA thermograms of pralsetinib Form A.

In one aspect, crystalline Form A of pralsetinib has a DSC pattern that is substantially the same DSC pattern shown in FIG. 1B. In particular, crystalline Form A (DSC) thermogram with an endothermic event observed at about 205° C.±2° C.

In one aspect, crystalline Form A of pralsetinib has a TGA pattern that is substantially the same TGA pattern shown in FIG. 1B.

Figure 1C:
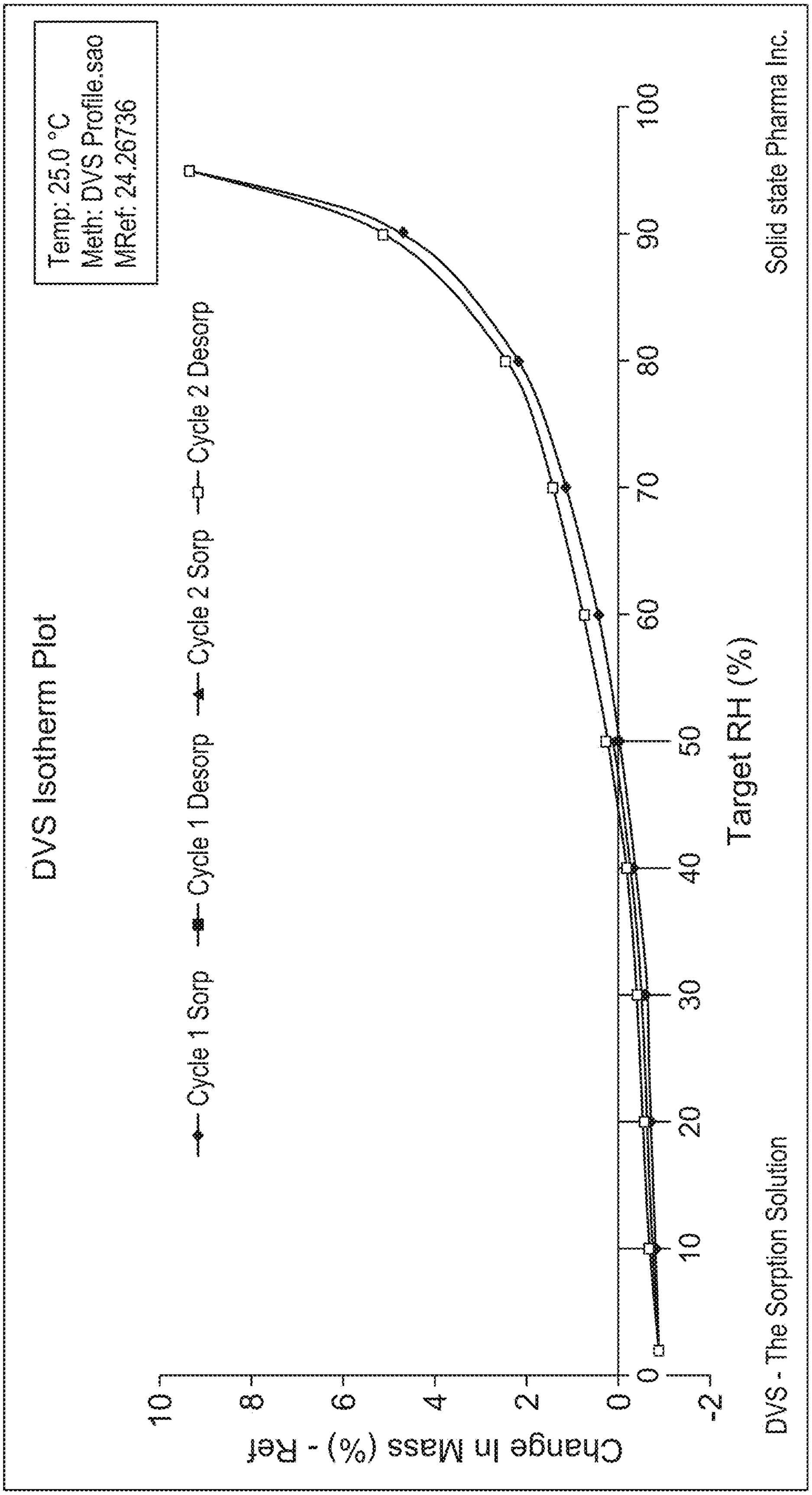
FIG. 1C shows the DVS thermogram of pralsetinib Form A.

In one aspect, crystalline Form A of pralsetinib has a DVS pattern that is substantially the same DVS pattern shown in FIG. 1C. In particular, Form A of pralsetinib is characterized by a reversible mass change of about 10% by DVS between 2-95% relative humidity.

In one aspect, the crystalline Form A of pralsetinib is characterized by at least three, at least four, or by at least five, x-ray powder diffraction peaks at 2-theta angles selected from 5.0±0.2°, 9.7±0.2°, 12.7±0.2°, 13.6±0.2°, and 16.1±0.2°; optionally together with one, two, or three of the TGA, DSC, DVS parameters recited above for Form A. Alternatively, crystalline Form A is characterized by at least three, at least four, at least five, at least six, at least seven, at least eight, or at least nine x-ray powder diffraction peaks at 2-theta angles selected from 5.0±0.2°, 6.8±0.2°, 9.7±0.2°, 12.7±0.2°, 13.6±0.2°, 16.1±0.2°, 19.2±0.2°, 19.5±0.2°, and 23.5±0.2° optionally together with one, two, or three of the TGA, DSC, DVS parameters recited above for Form A. Alternatively, crystalline Form A is characterized by at least three, at least four, at least five, at least six, at least seven, at least eight, at least nine, or at least ten x-ray powder diffraction peaks at 2-theta angles selected from 5.0±0.2°, 6.8±0.2°, 9.7±0.2°, 12.7±0.2°, 13.6±0.2°, 14.8±0.2°, 16.1±0.2°, 17.2±0.2°, 17.8±0.2°, 19.2±0.2°, 19.5±0.2°, 20.5±0.2°, 21.6±0.2°, 23.1±0.2°, 23.5±0.2°, 24.8±0.2°, 25.6±0.2°, 26.0±0.2°, 27.9±0.2°, and 29.4±0.2° optionally together with one, two, or three of the TGA, DSC, DVS parameters recited above for Form A.

In one aspect, the crystalline Form A of pralsetinib is characterized by one or more of the following characteristics: (a) a X-ray powder diffraction (XRPD) pattern comprising characteristic diffraction peaks at 2-theta angles at approximately (±0.2 degrees) 5.0±0.2°, 9.7±0.2°, 12.7±0.2°, 13.6±0.2°, and 16.1±0.2°; (b) a differential scanning calorimetry (DSC) thermogram with an endothermic event observed at about 205° C.±2° C.; and/or (c) a reversible mass change of about 10% by dynamic vapor sorption (DVS) between 2-95% relative humidity.

Form A can be a solid form obtained by a process comprising a step selected from the group consisting of: (a) slurrying in alcohols, acetone, or ACN; (b) evaporative crystallization and cooling crystallization in IPA and 1-propanol; and (c) recrystallization in acetone:water. Form A can also be obtained by heating a sample of Form B to at least about 190° C. under suitable conditions to yield Form A (e.g., a slurry in an alcohol such as IPA); or by heating a sample of pralsetinib Form C to at least about 190° C. under suitable conditions to yield Form A (e.g., a slurry in an alcohol, acetone or ACN).

In one aspect, the present disclosure provides crystalline Form B of pralsetinib.

In one aspect, crystalline Form B of pralsetinib is characterized by x-ray powder diffraction pattern. The x-ray powder diffraction pattern can be acquired using a Bruker D8 Advance as described herein. In one embodiment, crystalline Form B is characterized by at least three, at least four, or at least five x-ray powder diffraction peaks at 2-theta angles selected from 5.9±0.2°, 8.8±0.2°, 11.6±0.2°, 14.7±0.2°, and 19.5±0.2°.

Alternatively, crystalline Form B is characterized by at least three, at least four, at least five, at least six, at least seven, or at least eight x-ray powder diffraction peaks at 2-theta angles selected from 5.9±0.2°, 8.8±0.2°, 11.6±0.2°, 14.7±0.2°, 17.0±0.2°, 17.6±0.2°, 19.5±0.2°, and 22.2±0.2°. Alternatively, crystalline Form B is characterized by x-ray powder diffraction peaks at 2-theta angles 5.9±0.2°, 8.8±0.2°, 11.6±0.2°, 14.7±0.2°, 17.0±0.2°, 17.6±0.2°, 19.5±0.2°, and 22.2±0.2°. In some embodiments, the peaks described above for crystalline Form B have a relative intensity of at least 10%, of at least 15%, of at least 20%, or of at least 25%.

Figure 2A:
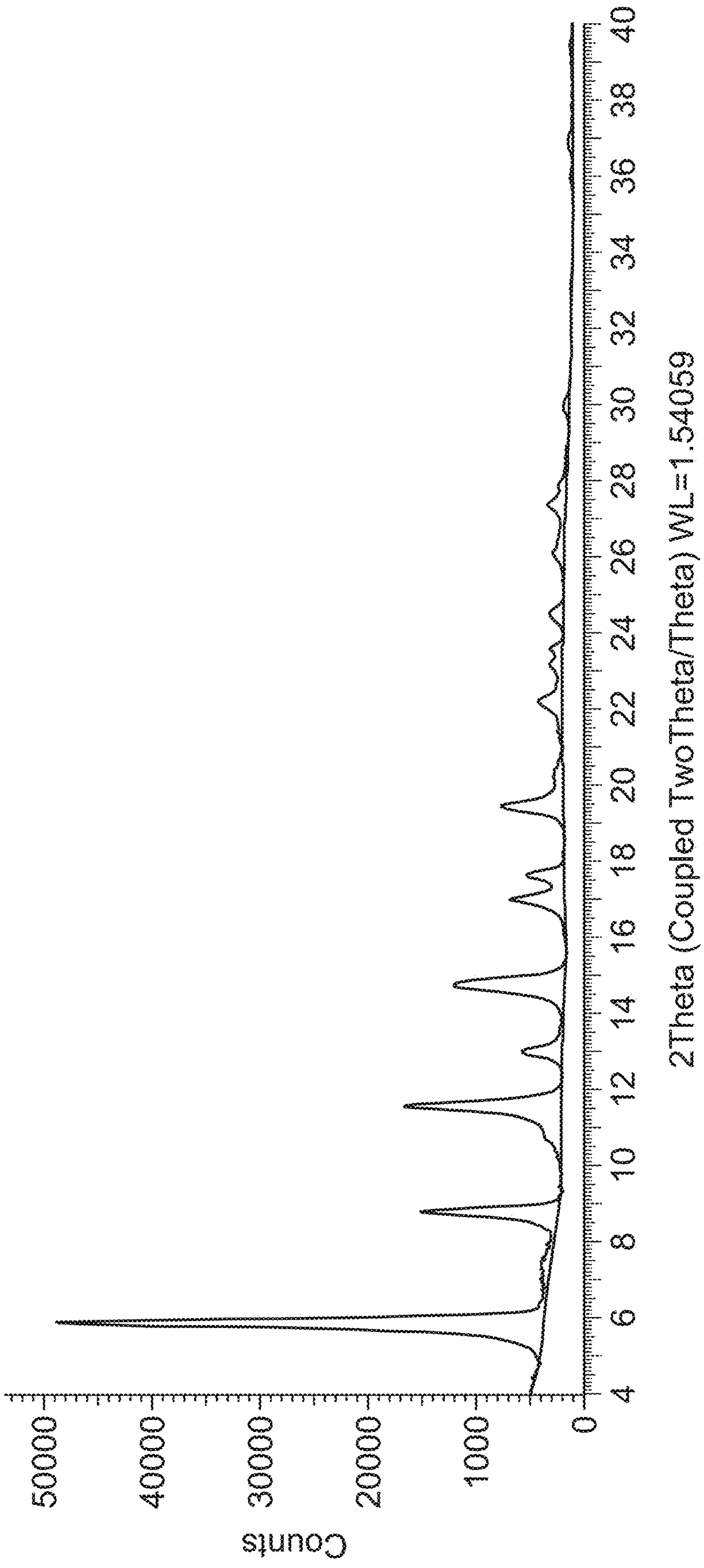
FIG. 2A is an X-ray powder diffraction pattern (XRPD) pattern of pralsetinib Form B.

In another aspect, crystalline Form B of pralsetinib has an XRPD pattern that is substantially the same XRPD pattern shown in FIG. 2A.

In another aspect, crystalline Form B of pralsetinib has an XRPD pattern that substantially includes the peaks in Table 2A.

Figure 2B:
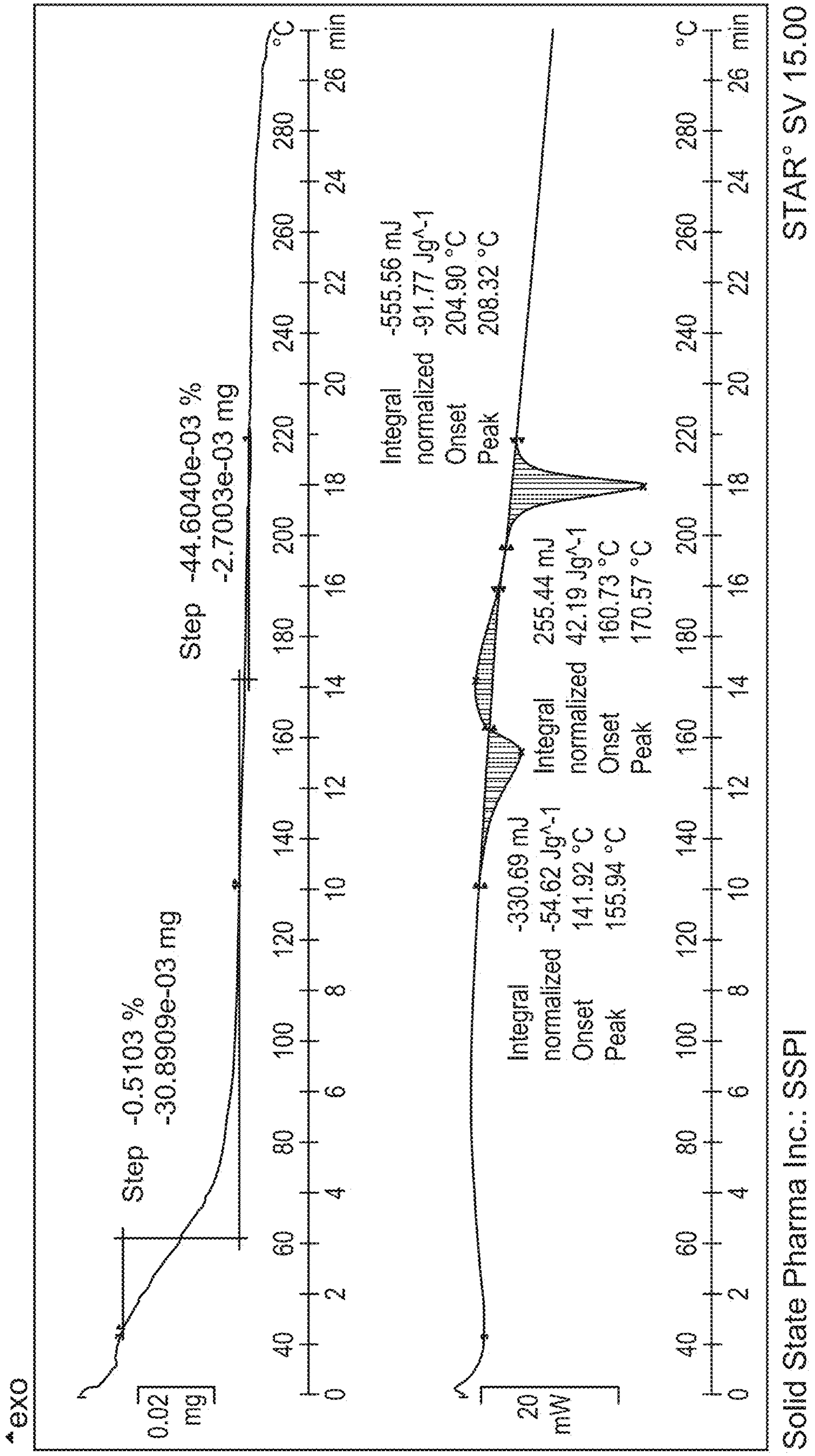
FIG. 2B shows DSC and TGA thermograms of pralsetinib Form B.

In one aspect, crystalline Form B of pralsetinib has a DSC pattern that is substantially the same DSC pattern shown in FIG. 2B. In particular, three features are observed when crystalline Form B is characterized by DSC: an endotherm with onset at 149° C.±2° C., an exotherm with onset at 162° C.±2° C., and melting with onset 205° C.±2° C.

In one aspect, crystalline Form B of pralsetinib has a TGA pattern that is substantially the same TGA pattern shown in FIG. 2B. In particular, the mass loss was 0.5% as characterized by TGA.

Figure 2C:
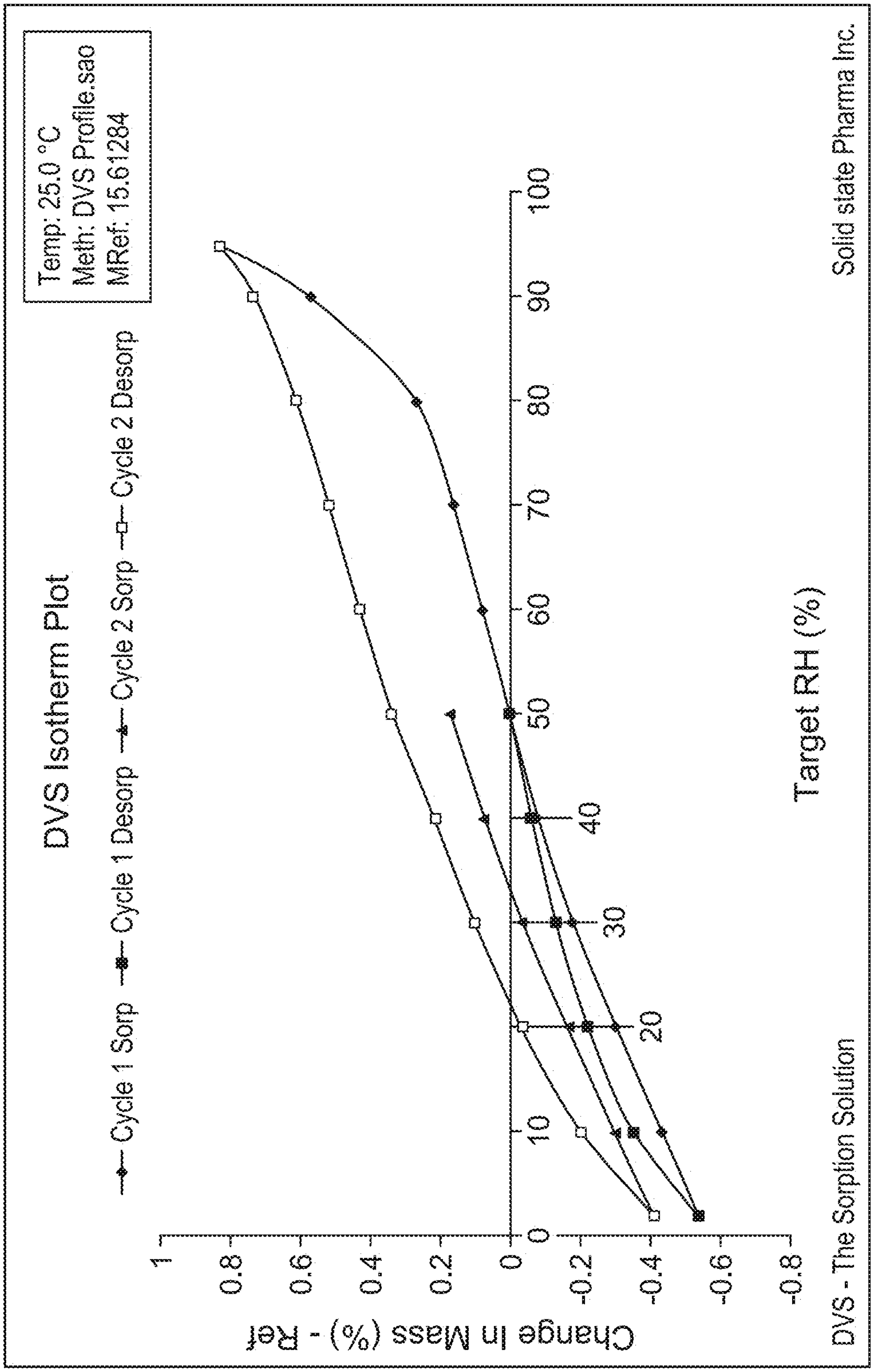
FIG. 2C shows the DVS thermogram of pralsetinib Form B.

In one aspect, crystalline Form B of pralsetinib has a DVS pattern that is substantially the same DVS pattern shown in FIG. 2C. In particular, crystalline Form B showed a total mass change of 1.4 wt. % between 2% and 95% relative humidity.

In one aspect, the crystalline Form B of pralsetinib is characterized by at least three, at least four, or by at least five, x-ray powder diffraction peaks at 2-theta angles selected from 5.9±0.2°, 8.8±0.2°, 11.6±0.2°, 14.7±0.2°, and 19.5±0.2°; optionally together with one, two, or three of the TGA, DSC, DVS parameters recited above for Form B. Alternatively, crystalline Form B is characterized by at least three, at least four, at least five, at least six, at least seven, or at least eight x-ray powder diffraction peaks at 2-theta angles selected from 5.9±0.2°, 8.8±0.2°, 11.6±0.2°, 14.7±0.2°, 17.0±0.2°, 17.6±0.2°, 19.5±0.2°, and 22.2±0.2° optionally together with one, two, or three of the TGA, DSC, DVS parameters recited above for Form B.

In one aspect, the crystalline Form B of pralsetinib is characterized by one or more of the following characteristics: (a) a X-ray powder diffraction (XRPD) pattern comprising characteristic diffraction peaks at 2-theta angles at approximately (±0.2 degrees) 5.9±0.2°, 8.8±0.2°, 11.6±0.2°, 14.7±0.2°, and 19.5±0.2°; (b) three features are observed when crystalline Form B is characterized by DSC: an endotherm with onset at 149° C.±2° C., an exotherm with onset at 162° C.±2° C., and melting with onset 205° C.±2° C.; (c) a mass loss was 0.5% as characterized by TGA; and/or (c) a total mass change of 1.4 wt. % between 2% and 95% relative humidity by DVS.

Form B can be obtained by a process comprising a step of heating a sample of Form C to about 150° C.

In one aspect, the present disclosure provides crystalline Form C of pralsetinib.

In one aspect, crystalline Form C of pralsetinib is characterized by x-ray powder diffraction pattern. The x-ray powder diffraction pattern can be acquired using a Bruker D8 Advance as described herein. In one embodiment, crystalline Form C is characterized by at least three, at least four, or at least five x-ray powder diffraction peaks at 2-theta angles selected from 5.8±0.2°, 8.7±0.2°, 11.0±0.2°, 13.6±0.2°, and 20.2±0.2°.

Alternatively, crystalline Form C is characterized by at least three, at least four, at least five, at least six, at least seven, at least eight, or at least nine x-ray powder diffraction peaks at 2-theta angles selected from 5.8±0.2°, 8.7±0.2°, 11.0±0.2°, 11.6±0.2°, 13.6±0.2°, 14.5±0.2°, 20.2±0.2°, 22.2±0.2°, and 23.2±0.2°. Alternatively, crystalline Form C is characterized by x-ray powder diffraction peaks at 2-theta angles 5.8±0.2°, 8.7±0.2°, 11.0±0.2°, 11.6±0.2°, 13.6±0.2°, 14.5±0.2°, 20.2±0.2°, 22.2±0.2°, and 23.2±0.2°.

Alternatively, crystalline Form C is characterized by at least three, at least four, at least five, at least six, at least seven, at least eight, at least nine, or at least ten x-ray powder diffraction peaks at 2-theta angles selected from 5.8±0.2°, 8.7±0.2°, 11.0±0.2°, 11.6±0.2°, 12.0±0.2°, 13.6±0.2°, 14.5±0.2°, 17.1±0.2°, 18.2±0.2°, 19.5±0.2°, 20.2±0.2°, 20.6±0.2°, 21.3±0.2°, 22.2±0.2°, 22.6±0.2°, 23.2±0.2°, 24.2±0.2°, 24.5±0.2°, 26.0±0.2°, 26.8±0.2°, and 28.1±0.2°. In another alternative crystalline Form C is characterized by x-ray powder diffraction peaks at 2-theta angles 5.8±0.2°, 8.7±0.2°, 11.0±0.2°, 11.6±0.2°, 12.0±0.2°, 13.6±0.2°, 14.5±0.2°, 17.1±0.2°, 18.2±0.2°, 19.5±0.2°, 20.2±0.2°, 20.6±0.2°, 21.3±0.2°, 22.2±0.2°, 22.6±0.2°, 23.2±0.2°, 24.2±0.2°, 24.5±0.2°, 26.0±0.2°, 26.8±0.2°, and 28.1±0.2°. In some embodiments, the peaks described above for crystalline Form C have a relative intensity of at least 10%, of at least 15%, of at least 20%, or of at least 25%.

Figure 3A:
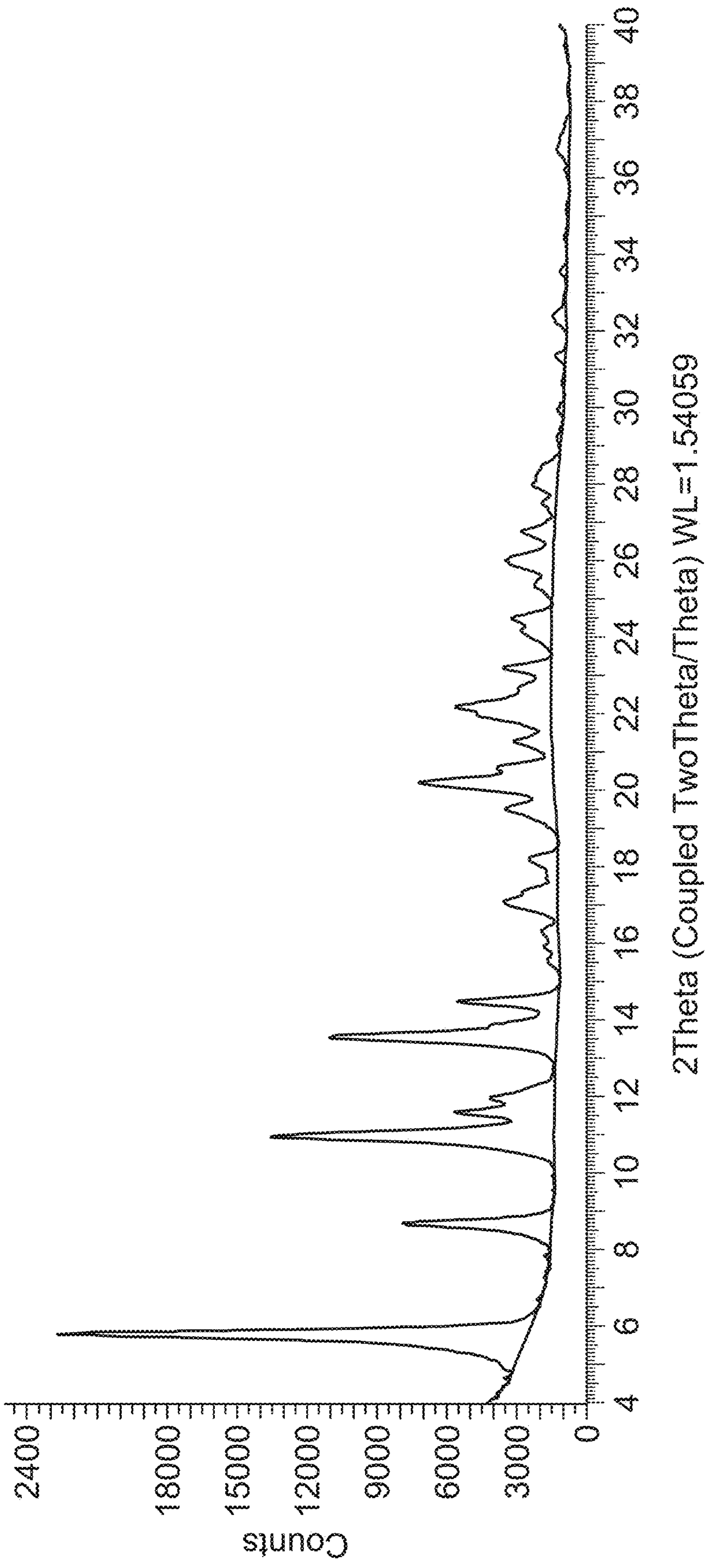
FIG. 3A is an X-ray powder diffraction pattern (XRPD) pattern of pralsetinib Form C.

In another aspect, crystalline Form C of pralsetinib has an XRPD pattern that is substantially the same XRPD pattern shown in FIG. 3A.

In another aspect, crystalline Form C of pralsetinib has an XRPD pattern that substantially includes the peaks in Table 3A.

Figure 3B:
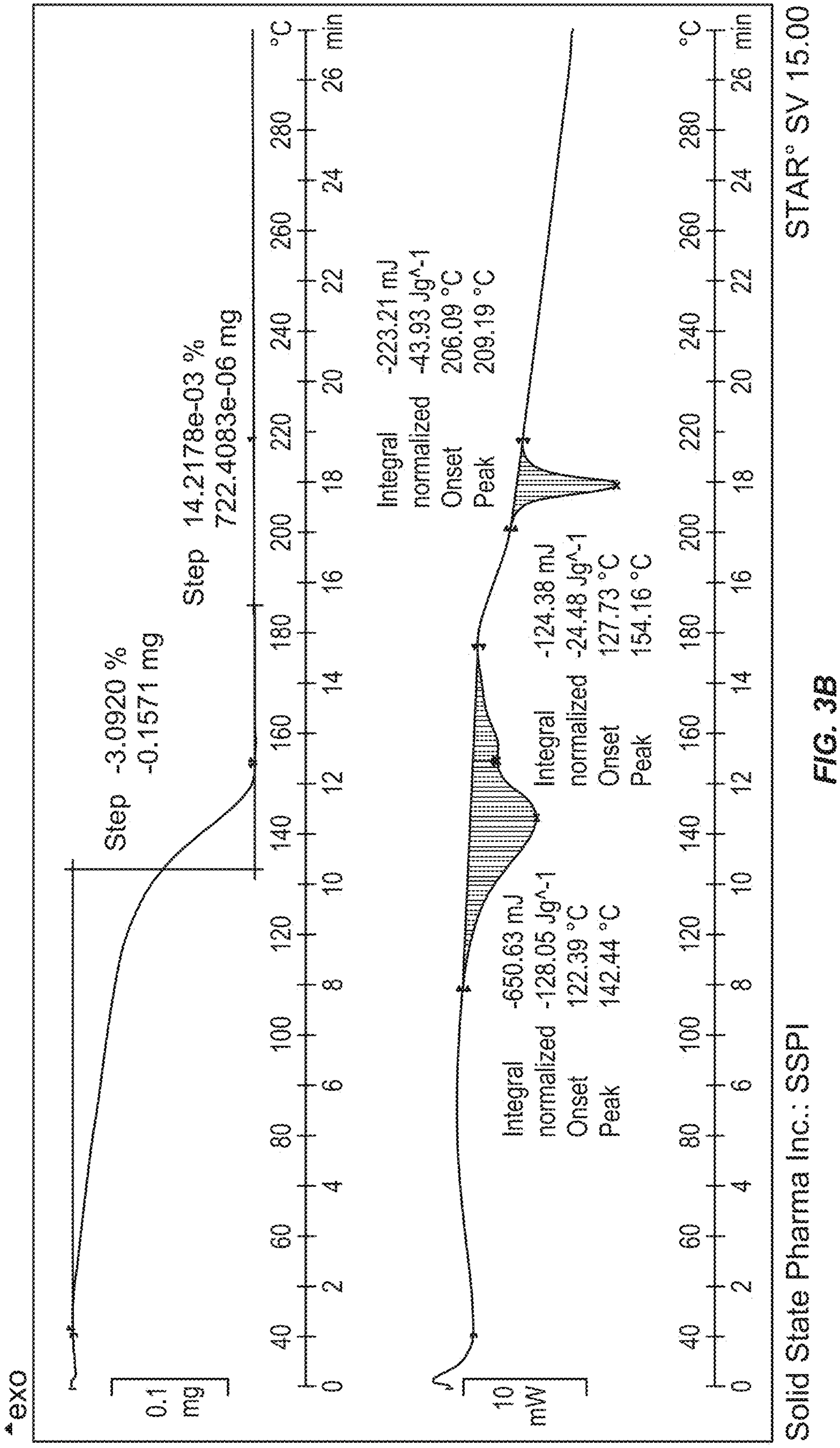
FIG. 3B shows DSC and TGA thermograms of pralsetinib Form C.

In one aspect, crystalline Form C of pralsetinib has a DSC pattern that is substantially the same DSC pattern shown in FIG. 3B. In particular, crystalline Form C has DSC onset occurring at 122°, 127°, and 206°.

In one aspect, crystalline Form C of pralsetinib has a TGA pattern that is substantially the same TGA pattern shown in FIG. 3B. In particular, a mass loss of about 3 wt. % in observed in the Form C TGA thermogram.

Figure 3C:
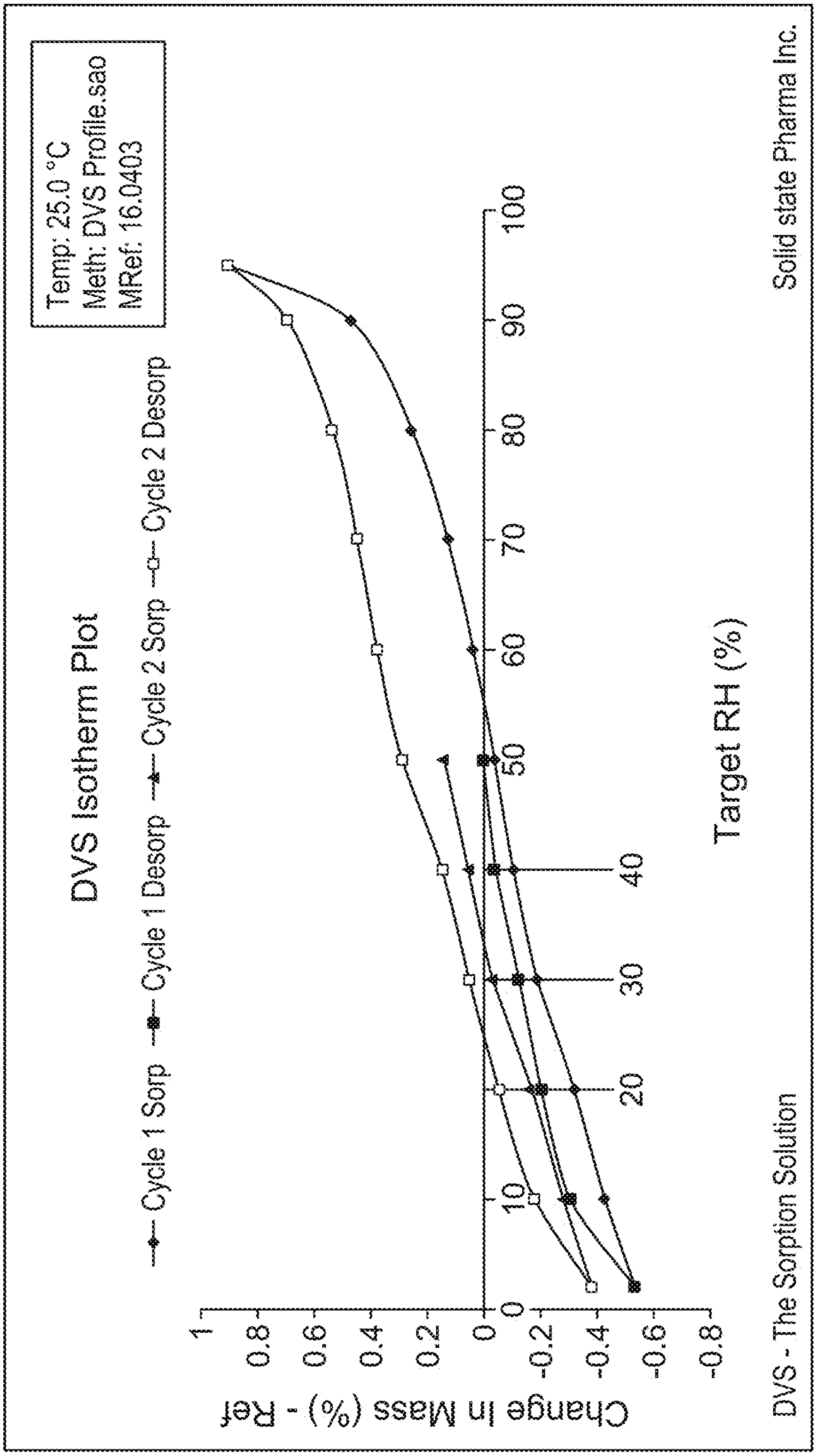
FIG. 3C shows the DVS thermogram of pralsetinib Form C.

In one aspect, crystalline Form C of pralsetinib has a DVS pattern that is substantially the same DVS pattern shown in FIG. 3C. In particular, crystalline Form C showed a total mass change of 1.4 wt. % between 2% and 95% relative humidity.

In one aspect, the crystalline Form C of pralsetinib is characterized by at least three, at least four, or by at least five, x-ray powder diffraction peaks at 2-theta angles selected from 5.8±0.2°, 8.7±0.2°, 11.0±0.2°, 13.6±0.2°, and 20.2±0.2°; optionally together with one, two, or three of the TGA, DSC, DVS parameters recited above for Form C. Alternatively, crystalline Form C is characterized by at least three, at least four, at least five, at least six, at least seven, at least eight, or at least nine x-ray powder diffraction peaks at 2-theta angles selected from 5.8±0.2°, 8.7±0.2°, 11.0±0.2°, 11.6±0.2°, 13.6±0.2°, 14.5±0.2°, 20.2±0.2°, 22.2±0.2°, and 23.2±0.2° optionally together with one, two, or three of the TGA, DSC, DVS parameters recited above for Form C. Alternatively, crystalline Form C is characterized by at least three, at least four, at least five, at least six, at least seven, at least eight, at least nine, or at least ten x-ray powder diffraction peaks at 2-theta angles selected from 5.8±0.2°, 8.7±0.2°, 11.0±0.2°, 11.6±0.2°, 12.0±0.2°, 13.6±0.2°, 14.5±0.2°, 17.1±0.2°, 18.2±0.2°, 19.5±0.2°, 20.2±0.2°, 20.6±0.2°, 21.3±0.2°, 22.2±0.2°, 22.6±0.2°, 23.2±0.2°, 24.2±0.2°, 24.5±0.2°, 26.0±0.2°, 26.8±0.2°, and 28.1±0.2° optionally together with one, two, or three of the TGA, DSC, DVS parameters recited above for Form C.

In one aspect, the crystalline Form C of pralsetinib is characterized by one or more of the following characteristics: (a) a X-ray powder diffraction (XRPD) pattern comprising characteristic diffraction peaks at 2-theta angles at approximately (±0.2 degrees) 5.8±0.2°, 8.7±0.2°, 11.0±0.2°, 13.6±0.2°, and 20.2±0.2°; (b) a differential scanning calorimetry (DSC) thermogram with a onset occurring at 122°, 127°, and 206°; (c) a mass loss of about 3 wt. % observed in TGA thermogram; and/or (d) a total mass change of 1.4 wt. % between 2% and 95% relative humidity by DVS.

Form C can be a solid form obtained by a process comprising a step selected from the group consisting of: a) recrystallization in various water containing solvent systems (acetone:water, methanol (MeOH):water, isopropyl alcohol (IPA):water, dimethylacetamide (DMAc):water, tetrahydrofuran (THF):water); b) conversion from Form A during competitive slurry experiments in methanol:water at high ratios of water to methanol and lower temperatures. The solid form C of the free base of pralsetinib can be obtained by slurrying and then recrystallizing a sample of pralsetinib free base in an anhydrous solid form (e.g., slurry pralsetinib free base Solid Form A in water and methanol, then recrystallize in acetone/IPA/methanol and water to obtain hydrated crystalline solid form C of the pralsetinib free base).

In one aspect, the present disclosure provides crystalline pralsetinib HCl salt Form I. In one aspect, crystalline pralsetinib HCl salt Form I is characterized by x-ray powder diffraction pattern. The x-ray powder diffraction pattern can be acquired using a Rigaku MiniFlex 600 described herein. In one embodiment, crystalline pralsetinib HCl salt Form I is characterized by at least three, at least four, or at least five x-ray powder diffraction peaks at 2-theta angles selected from 5.0±0.2°, 6.1±0.2°, 9.1±0.2°, 9.9±0.2°, and 14.7±0.2°.

Alternatively, crystalline pralsetinib HCl salt Form I is characterized by at least three, at least four, at least five, at least six, at least seven, at least eight, at least nine, or at least ten x-ray powder diffraction peaks at 2-theta angles selected from 5.0±0.2°, 6.1±0.2°, 9.1±0.2°, 9.9±0.2°, 13.8±0.2°, 14.7±0.2°, 15.3±0.2°, 17.2±0.2°, 18.1±0.2°, 19.6±0.2°, 20.3±0.2°, 20.7±0.2°, 21.8±0.2°, 24.2±0.2°, 25.6±0.2°, and 26.3±0.2°. Alternatively, crystalline pralsetinib HCl salt Form I is characterized by x-ray powder diffraction peaks at 2-theta angles 5.0±0.2°, 6.1±0.2°, 9.1±0.2°, 9.9±0.2°, 13.8±0.2°, 14.7±0.2°, 15.3±0.2°, 17.2±0.2°, 18.1±0.2°, 19.6±0.2°, 20.3±0.2°, 20.7±0.2°, 21.8±0.2°, 24.2±0.2°, 25.6±0.2°, and 26.3±0.2°. In some embodiments, the peaks described above for crystalline pralsetinib HCl salt Form I have a relative intensity of at least 10%, of at least 15%, of at least 20%, or of at least 25%.

Figure 4A:
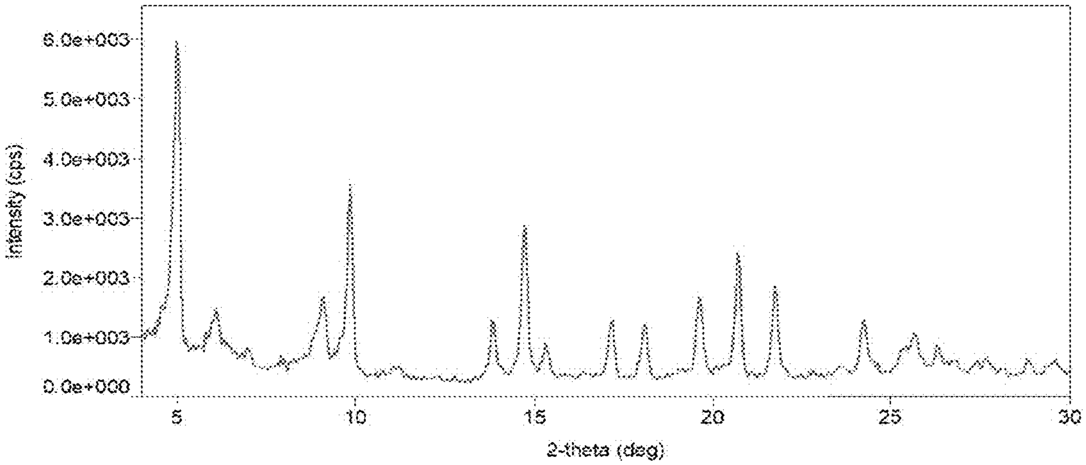
FIG. 4A is an X-ray powder diffraction pattern (XRPD) pattern of pralsetinib HCl salt Form I.

In another aspect, crystalline pralsetinib HCl salt Form I of pralsetinib has an XRPD pattern that is substantially the same XRPD pattern shown in FIG. 4A.

In another aspect, crystalline pralsetinib HCl salt Form I has an XRPD pattern that substantially includes the peaks in Table 4A.

Figure 4B:
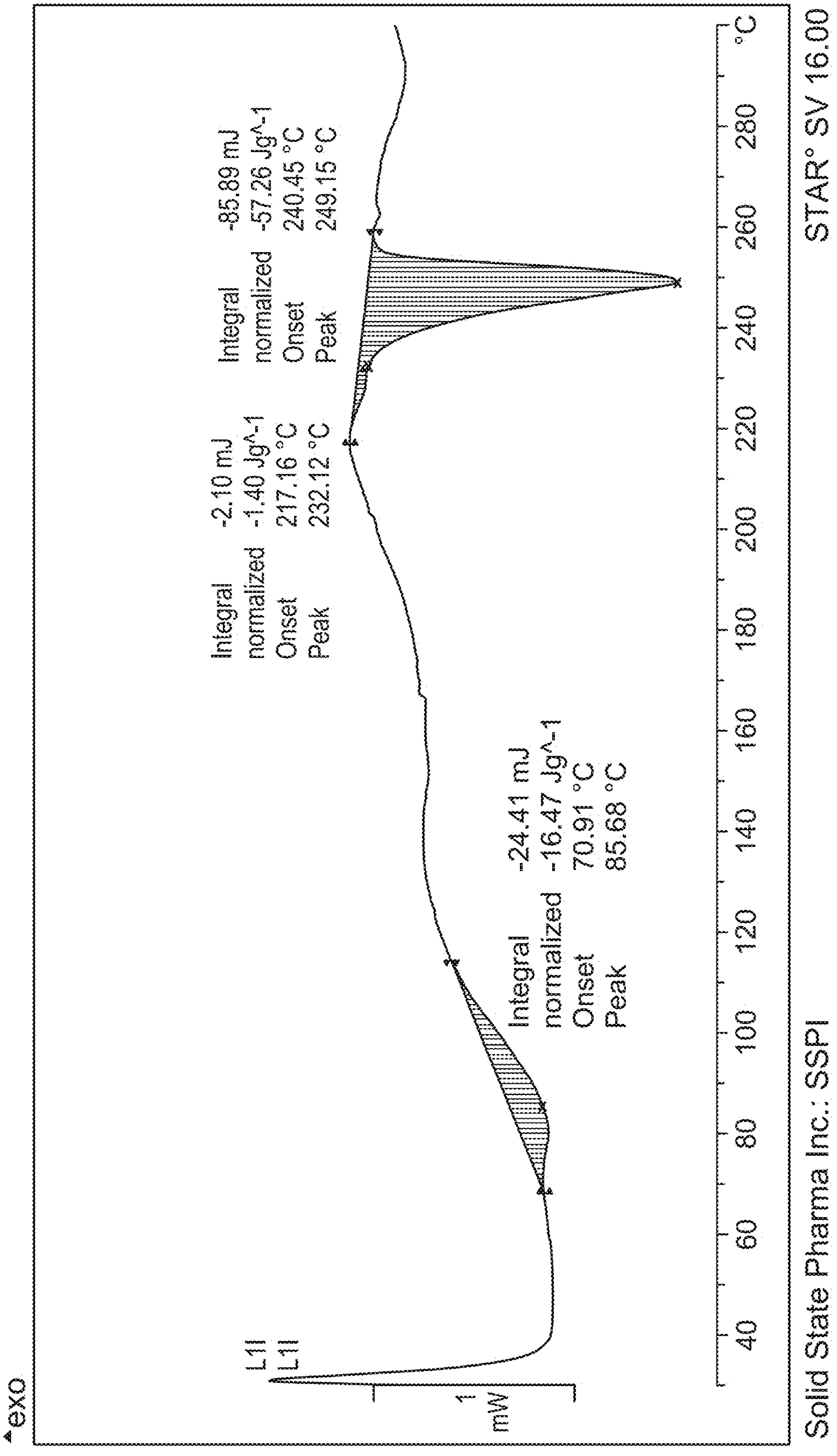
FIG. 4B shows DSC thermogram of pralsetinib HCl salt Form I.

In one aspect, crystalline pralsetinib HCl salt Form I has a DSC pattern that is substantially the same DSC pattern shown in FIG. 4B. In particular, pralsetinib HCl salt Form I was observed to have a very broad endotherm with an onset temperature of 70.9° C.±2° C. and a sharp endotherm at 240.5±2° C.

In one aspect, the crystalline pralsetinib HCl salt Form I is characterized by at least three, at least four, or by at least five, x-ray powder diffraction peaks at 2-theta angles selected from 5.0±0.2°, 6.1±0.2°, 9.1±0.2°, 9.9±0.2°, and 14.7±0.2°; optionally together with the TGA and DSC parameters recited above for pralsetinib HCl salt Form I. Alternatively, crystalline pralsetinib HCl salt Form I is characterized by at least three, at least four, at least five, at least six, at least seven, at least eight, at least nine, or at least ten x-ray powder diffraction peaks at 2-theta angles selected from 5.0±0.2°, 6.1±0.2°, 9.1±0.2°, 9.9±0.2°, 13.8±0.2°, 14.7±0.2°, 15.3±0.2°, 17.2±0.2°, 18.1±0.2°, 19.6±0.2°, 20.3±0.2°, 20.7±0.2°, 21.8±0.2°, 24.2±0.2°, 25.6±0.2°, and 26.3±0.2° optionally together with the DSC parameters recited above for pralsetinib HCl salt Form I.

In one aspect, the crystalline pralsetinib HCl salt Form I is characterized by one or more of the following characteristics: (a) a X-ray powder diffraction (XRPD) pattern comprising characteristic diffraction peaks at 2-theta angles at approximately (±0.2 degrees) 5.0°, 6.1°, 9.1°, 9.9°, and 14.7°; and/or (b) a differential scanning calorimetry (DSC) thermogram with a very broad endotherm with an onset temperature of 70.9° C.±2° C. and a sharp endotherm at 240.5° C.±2°.

Pralsetinib HCl salt Form I can obtained by a process comprising isolating the solid from the slurry of the HCl salt in EtOH or IPA:water (9:1 Vol).

In one aspect, the present disclosure provides crystalline pralsetinib HCl salt Form II. In one aspect, crystalline pralsetinib HCl salt Form II is characterized by x-ray powder diffraction pattern. The x-ray powder diffraction pattern can be acquired using a Bruker D8 described herein. In one embodiment, crystalline pralsetinib HCl salt Form II is characterized by at least three, at least four, or at least five x-ray powder diffraction peaks at 2-theta angles selected from 6.1±0.2°, 8.9±0.2°, 9.5±0.2°, 15.0±0.2°, and 16.6±0.2°.

Alternatively, crystalline pralsetinib HCl salt Form II is characterized by at least three, at least four, at least five, at least six, at least seven, at least eight, at least nine, or at least 10 x-ray powder diffraction peaks at 2-theta angles selected from 6.1±0.2°, 8.9±0.2°, 9.5±0.2°, 15.0±0.2°, 16.6±0.2°, 17.2±0.2°, 17.9±0.2°, 18.4±0.2°, 19.8±0.2°, 25.8±0.2°, and 26.8±0.2°. Alternatively, crystalline pralsetinib HCl salt Form II is characterized by x-ray powder diffraction peaks at 2-theta angles 6.1±0.2°, 8.9±0.2°, 9.5±0.2°, 15.0±0.2°, 16.6±0.2°, 17.2±0.2°, 17.9±0.2°, 18.4±0.2°, 19.8±0.2°, 25.8±0.2°, and 26.8±0.2°. In some embodiments, the peaks described above for crystalline pralsetinib HCl salt Form II have a relative intensity of at least 10%, of at least 15%, of at least 20%, or of at least 25%.

Figure 5A:
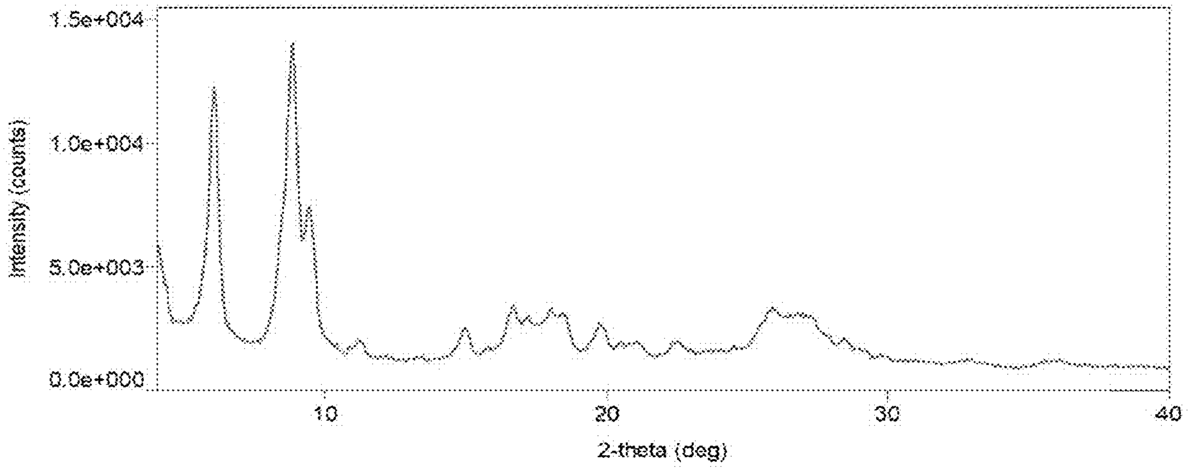
FIG. 5A is an X-ray powder diffraction pattern (XRPD) pattern of pralsetinib HCl salt Form II.

In another aspect, crystalline pralsetinib HCl salt Form II of pralsetinib has an XRPD pattern that is substantially the same XRPD pattern shown in FIG. 5A.

In another aspect, crystalline pralsetinib HCl salt Form II has an XRPD pattern that substantially includes the peaks in Table 5A.

Figure 5B:
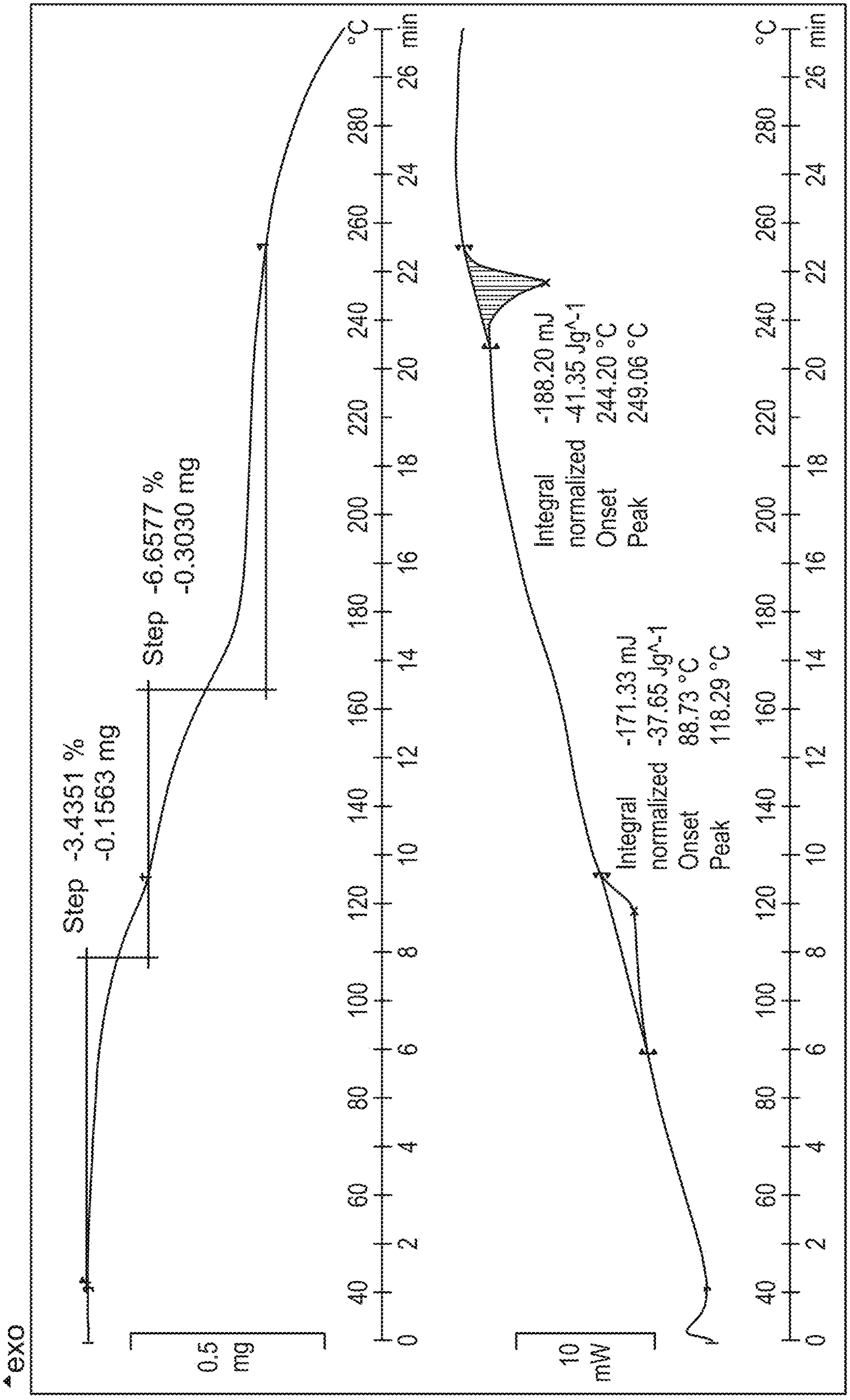
FIG. 5B shows DSC and TGA thermograms of pralsetinib HCl salt Form II.

In one aspect, crystalline pralsetinib HCl salt Form II has a DSC pattern that is substantially the same DSC pattern shown in FIG. 5B. In particular, pralsetinib HCl salt Form II was observed to have a broad endotherm with an onset of 88.7° C.±2° C. and a melt which had an onset of 244.2° C.±2° C.

In one aspect, crystalline pralsetinib HCl salt Form II has a TGA pattern that is substantially the same TGA pattern shown in FIG. 5B. In particular, an initial mass loss of 3.4 wt. % associated with a broad endotherm with an onset of 94.4° C.±2° C. and a second mass loss event of 6.7 wt. % was observed from the end of the first broad endotherm to the end of the melt which had an onset of 244.2° C.±2° C. was observed in the pralsetinib HCl salt Form II TGA thermogram.

In one aspect, the crystalline pralsetinib HCl salt Form II is characterized by at least three, at least four, or by at least five, x-ray powder diffraction peaks at 2-theta angles selected from 6.1±0.2°, 8.9±0.2°, 9.5±0.2°, 15.0±0.2°, and 16.6±0.2°; optionally together with one or two the TGA and DSC parameters recited above for pralsetinib HCl salt Form II. Alternatively, crystalline pralsetinib HCl salt Form II is characterized by at least three, at least four, at least five, at least six, at least seven, at least eight, or at least nine x-ray powder diffraction peaks at 2-theta angles selected from 6.1±0.2°, 8.9±0.2°, 9.5±0.2°, 15.0±0.2°, 16.6±0.2°, 17.2±0.2°, 17.9±0.2°, 18.4±0.2°, 19.8±0.2°, 25.8±0.2°, and 26.8±0.2° optionally together with one, two, or three of the TGA, DSC parameters recited above for pralsetinib HCl salt Form II.

In one aspect, the crystalline pralsetinib HCl salt Form II is characterized by one or more of the following characteristics: (a) a X-ray powder diffraction (XRPD) pattern comprising characteristic diffraction peaks at 2-theta angles at approximately (±0.2 degrees) 6.1°, 8.9°, 9.5°, 15.0°, 16.6°; (b) a DSC thermogram with a to have a broad endotherm with an onset of 88.7° C.±2° C. and a melt which had an onset of 244.2° C.±2° C.; and/or (c) an initial mass loss of 3.4 wt. % associated with a broad endotherm with an onset of 88.7° C. and a second mass loss event of 6.7 wt. % was observed from the end of the first broad endotherm to the end of the melt which had an onset of 244.2° C.±2° C.

Pralsetinib HCl salt Form II can obtained by a process comprising isolating the solid from EtOAc and IPA:water (9:1 vol).

In one aspect, the present disclosure provides crystalline pralsetinib HCl salt Form III. In one aspect, crystalline pralsetinib HCl salt Form III is characterized by x-ray powder diffraction pattern. The x-ray powder diffraction pattern can be acquired using a Bruker D8 Advance as described herein. In one embodiment, crystalline pralsetinib HCl salt Form III is characterized by at least three, at least four, or at least five x-ray powder diffraction peaks at 2-theta angles selected from 6.4±0.2°, 8.5±0.2°, 8.9±0.2°, 9.6±0.2°, and 17.3±0.2°.

Alternatively, crystalline pralsetinib HCl salt Form III is characterized by at least three, at least four, at least five, at least six, at least seven, at least eight, or at least nine x-ray powder diffraction peaks at 2-theta angles selected from 6.4±0.2°, 8.5±0.2°, 8.9±0.2°, 9.6±0.2°, 11.5±0.2°, 16.7±0.2°, 17.3±0.2°, and 19.2±0.2°. Alternatively, crystalline pralsetinib HCl salt Form III is characterized by x-ray powder diffraction peaks at 2-theta angles 6.4±0.2°, 8.5±0.2°, 8.9±0.2°, 9.6±0.2°, 11.5±0.2°, 16.7±0.2°, 17.3±0.2°, and 19.2±0.2°.

Alternatively, crystalline pralsetinib HCl salt Form III is characterized by at least three, at least four, at least five, at least six, at least seven, at least eight, at least nine, or at least ten x-ray powder diffraction peaks at 2-theta angles selected from 6.0±0.2°, 6.4±0.2°, 8.5±0.2°, 8.9±0.2°, 9.6±0.2°, 11.5±0.2°, 12.7±0.2°, 15.9±0.2°, 16.7±0.2°, 17.3±0.2°, 19.2±0.2°, 21.0±0.2°, and 26.9±0.2°. In another alternative crystalline pralsetinib HCl salt Form III is characterized by x-ray powder diffraction peaks at 2-theta angles selected from 6.0±0.2°, 6.4±0.2°, 8.5±0.2°, 8.9±0.2°, 9.6±0.2°, 11.5±0.2°, 12.7±0.2°, 15.9±0.2°, 16.7±0.2°, 17.3±0.2°, 19.2±0.2°, 21.0±0.2°, and 26.9±0.2°. In some embodiments, the peaks described above for crystalline pralsetinib HCl salt Form III have a relative intensity of at least 10%, of at least 15%, of at least 20%, or of at least 25%.

Figure 6A:
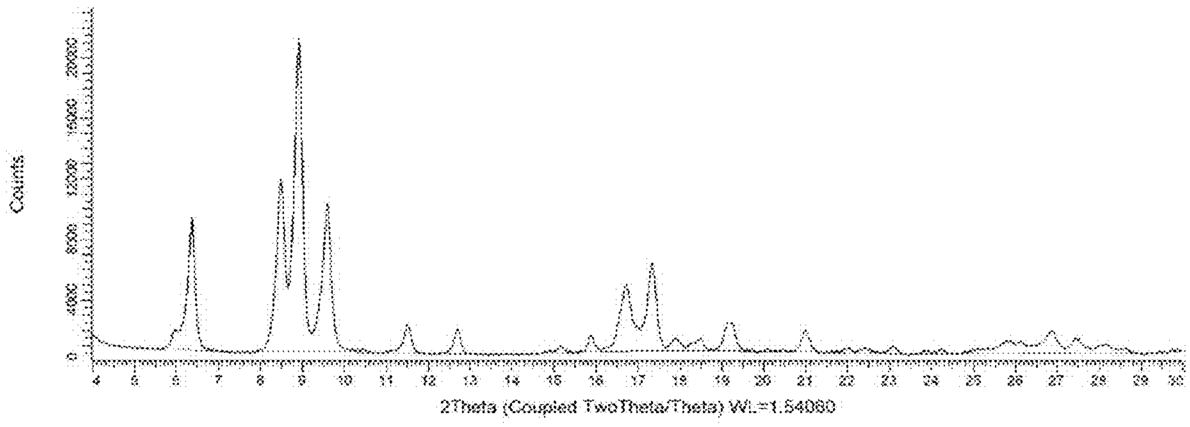
FIG. 6A is an X-ray powder diffraction pattern (XRPD) pattern of pralsetinib HCl salt Form III.

In another aspect, crystalline pralsetinib HCl salt Form III of pralsetinib has an XRPD pattern that is substantially the same XRPD pattern shown in FIG. 6A.

In another aspect, crystalline pralsetinib HCl salt Form II has an XRPD pattern that substantially includes the peaks in Table 6A.

In one aspect, crystalline pralsetinib HCl salt Form III has a DSC pattern that is substantially the same DSC pattern shown in FIG. 5C. In particular, pralsetinib HCl salt Form III had observed DSC onsets of 86.8° C.±2° C., 224.1° C.±2° C. and 241.7° C.±2° C.

In one aspect, crystalline pralsetinib HCl salt Form III has a TGA pattern that is substantially the same TGA pattern shown in FIG. 5C. In particular, an initial mass loss of 3.4 wt. % and a second mass loss event of 2 wt. % was observed in the pralsetinib HCl salt Form III TGA thermogram.

In one aspect, the crystalline pralsetinib HCl salt Form III is characterized by at least three, at least four, or by at least five, x-ray powder diffraction peaks at 2-theta angles selected 6.4±0.2°, 8.5±0.2°, 8.9±0.2°, 9.6±0.2°, and 17.3±0.2° optionally together with one or two the TGA and DSC parameters recited above for pralsetinib HCl salt Form III. Alternatively, crystalline pralsetinib HCl salt Form III is characterized by at least three, at least four, at least five, at least six, at least seven, at least eight, or at least nine x-ray powder diffraction peaks at 2-theta angles selected from 6.4±0.2°, 8.5±0.2°, 8.9±0.2°, 9.6±0.2°, 11.5±0.2°, 16.7±0.2°, 17.3±0.2°, and 19.2±0.2° optionally together with one, two, or three of the TGA, DSC, DVS parameters recited above for pralsetinib HCl salt Form III.

Alternatively, crystalline pralsetinib HCl salt Form III is characterized by at least three, at least four, at least five, at least six, at least seven, at least eight, at least nine, or at least ten x-ray powder diffraction peaks at 2-theta angles selected from 6.0±0.2°, 6.4±0.2°, 8.5±0.2°, 8.9±0.2°, 9.6±0.2°, 11.5±0.2°, 12.7±0.2°, 15.9±0.2°, 16.7±0.2°, 17.3±0.2°, 19.2±0.2°, 21.0±0.2°, and 26.9±0.2° optionally together with one or two of the TGA, DSC parameters recited above for pralsetinib HCl salt Form III.

In one aspect, the crystalline pralsetinib HCl salt Form III is characterized by one or more of the following characteristics: (a) a X-ray powder diffraction (XRPD) pattern comprising characteristic diffraction peaks at 2-theta angles at approximately (±0.2 degrees) 6.4±0.2°, 8.5±0.2°, 8.9±0.2°, 9.6±0.2°, and 17.3±0.2°; and (b) observed DSC onsets of 86.8° C.±2° C., 224.1° C.±2° C. and 241.7° C.±2° C., and/or (c) an initial mass loss of 3.4 wt. % and a second mass loss event of 2 wt. % was observed in the pralsetinib HCl salt Form III TGA thermogram.

Pralsetinib HCl salt Form III can obtained by a process comprising drying the isolated Pralsetinib HCl salt Form II.

It will be understood that the 2-theta values of the X-ray powder diffraction patterns for crystalline Form A, Form B, Form C, Form I, Form II, and Form III may vary slightly from one instrument to another and depending on variations in sample preparation and batch to batch variation. Therefore, the XRPD peak positions for crystalline Form A, Form B, Form C, Form I, Form II, and Form III in Tables 1A, 1B, 1C, 2A, 2B, 3A, 3B, 3C, 4A, 4B, 5A, 5B, 6A, 6B, and 6C are not to be construed as absolute and can vary ±0.2 degrees.

As intended herein, "substantially the same XRPD pattern as shown in FIG. 1A" and "substantially the same XRPD pattern as shown in FIG. 2A" and "substantially the same XRPD pattern as shown in FIG. 3A" and "substantially the same XRPD pattern as shown in FIG. 4A" and "substantially the same XRPD pattern as shown in FIG. 5A" and "substantially the same XRPD pattern as shown in FIG. 6A" means that for comparison purposes, at least 90% of the peaks shown in FIG. 1A, FIG. 2A, FIG. 3A, FIG. 4A, FIG. 5A, and FIG. 6A are present. It is to be further understood that for comparison purposes some variability in peak position from those shown in FIG. 1A, FIG. 2A, FIG. 3A, FIG. 4A, FIG. 5A, and FIG. 6A are allowed, such as +0.2 degrees.

In one aspect, the present disclosure provides a process for preparing crystalline Form A, Form B or Form C. In a particular aspect, Form A can be obtained by slurrying in alcohols, acetone, and acetonitrile or Form A was prepared by evaporative crystallization in multiple solvents and cooling crystallization in isopropanol and 1-propanol. Form A can also be produced by recrystallization in acetone:water. Form C can be obtained by recrystallizing Compound (I) in various water containing solvent systems (acetone:water, methanol:water, isopropanol:water, dimethylacetamide:water, tetrahydrofuran:water). Form C was stable drying at 50° C. under vacuum, and converted to Form B (anhydrous) upon heating to 150° C. Form B then converted to Form A before melting. Form C remained stable by X-ray powder diffraction during humidity testing (75% relative humidity and 40° C. for one week, and cycling down to 2% relative humidity by dynamic vapor sorption). Form C was not as hygroscopic as Form A during the dynamic vapor sorption measurements, gaining only 1.44% water. Form C exhibited lower solubility than Form A in simulated intestinal fluid and water, but high solubility in simulated gastric fluid (possibly due to conversion to HCl salt). Form C converted to Form A during competitive slurry experiments in acetone and isopropanol.

Treatment Methods

Another embodiment of the invention features a method of treating a RET-altered cancer comprising administering to a patient in need thereof a therapeutically effective amount of the compositions and oral dosage forms disclosed herein.

Another embodiment of the invention features a method of treating a patient with rearranged during transfection (RET)-positive locally advanced or metastatic non-small cell lung cancer (NSCLC) comprising administering to a patient in need thereof a therapeutically effective amount of the compositions and oral dosage forms disclosed herein. In a particular aspect, the (RET)-positive locally advanced or metastatic non-small cell lung cancer (NSCLC) is detected by an FDA approved test.

Another embodiment of the invention features a method of treating a patient with RET-mutation positive locally advanced or metastatic medullary thyroid cancer (MTC) comprising administering to the patient in need thereof a therapeutically effective amount of the compositions and oral dosage forms disclosed herein. In a particular aspect, the patients are 12 years of age and older.

Another embodiment of the invention features a method of treating a patient with RET-fusion positive locally advanced or metastatic thyroid cancer who require systemic therapy and have no satisfactory alternative treatment options comprising administering to the patient in need thereof a therapeutically effective amount of the compositions and oral dosage forms disclosed herin. In a particular aspect, the patients are 12 years of age and older.

As used herein, the term “subject” or “patient” refers to organisms to be treated by the methods of the present disclosure. Such organisms include, but are not limited to, mammals (e.g., murines, simians, equines, bovines, porcines, canines, felines, and the like), and in some embodiments, humans. In a particular aspect, the patient or subject is suffering from or suspected of suffering from a disease or disorder associated with aberrant RET expression (i.e., increased RET activity caused by signaling through RET) or biological activity. In particular, the disease or disorder is cancer. Many cancers have been linked to aberrant RET expression (Kato et al., Clin. Cancer Res. 23(8): 1988-97 (2017)). Non-limiting examples of “cancer” as used herein include lung cancer, head and neck cancer, gastrointestinal cancer, breast cancer, skin cancer, genitourinary tract cancer, gynecological cancer, hematological cancer, central nervous system (CNS) cancer, peripheral nervous system cancer, endometrial cancer, colorectal cancer, bone cancer, sarcoma, spitzoid neoplasm, adenosquamous carcinoma, pheochromocytoma (PCC), hepatocellular carcinoma, multiple endocrine neoplasia (MEN2A and MEN2B), and inflammatory myofibroblastic tumor. For other examples, see Nature Reviews Cancer 14: 173-86 (2014).

“Treat” and “treating” such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term “therapeutic effect” refers to a beneficial local or systemic effect in animals, particularly mammals, and more particularly humans, caused by administration of a compound or composition of the invention. The phrase “therapeutically-effective amount” means that amount of a compound or composition of the invention that is effective to treat a disease or condition caused by over expression of RET or aberrant RET biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

EXAMPLES

Example 1: Synthesis of Compound (I)

For each of the Forms of Compound (I) (i.e., pralsetinib) described herein in Example 2 and for each of the HCl salts of Compound (I) described herein Example 3, Compound (I) can be prepared as described with respect to compound 130 disclosed in publication WO2017/079140.

Example 2: Synthesis of Solid Forms of Compound (I)

Form A (anhydrous) was crystallized in the methanol/water system. Compound (I) (2-3g) was added to the vessel, to which 6.5 vol of MeOH was then added to the vessel. The mixture was stirred, maintaining stirring at 350 rpm (approximately 0.25 W/kg) with retreat curve impeller throughout. The mixture was heated to 60-65° C. over a period of 35 minutes, with dissolution observed at 63-64° C. The solution was then cooled solution to 44-45° C., and 1 volume of water was added over a period of 20 minutes. The solution was seeded with 0.5 wt. % Form A in saturated methanol:water (1:1 vol) as-is. Over 6 hr, 4.5 vol water was added, resulting in a final composition methanol:water (54:46 vol). The solution was held at 45° C. for 6-10 hours and then cooled to 25° C. over 2 hours (−10° C./h) and then held at 25° C. 1-2 hours. The mixtures was then filtered and washed 2×2 volumes methanol:water (1:1 vol) and dried at 50° C. under vacuum overnight to yielded 85-88% w/w anhydrous Form A.

Form A did not convert to Form C on prolonged humidity exposure. Form A converted to Form C during competitive slurry experiments in methanol:water at high ratios of water to methanol and lower temperatures. Form A exhibited low solubility in simulated intestinal fluid and water, but high solubility in simulated gastric fluid (possibly due to conversion to HCl salt).

a) Form C (hydrate) was crystallized in the acetone/water system. Compound (I) is added 10 volumes acetone/water 87:13 v/v and the mixture was heated to 50-55° C. for dissolution. The temperature was adjust temperature to 40° C. and 3 volumes water were added over a period of 30 minutes (rate of 15 mL/hour at 2.5 g scale), resulting in a solvent system that was acetone/water 67:33 v/v. The solution was seeded with 0.5 wt. % Form C, with the seed added as sonicated slurry in water. The slurry was held for 6 hours and then 7 volumes water was added over a period of 8 hours (rate of 2.2 mL/hour at 2.5 g scale), resulting in a solvent system of acetone/water 43:57 v/v. The mixture was cooled to 23° C. and filtered, with a yield of 85-90%.

b) Form C (hydrate) converted to a dehydrate, Form B, upon drying at 50° C.

Example 3: Synthesis of Solid Forms of the Compound (I) HCl Salt a) Pralsetinib HCl Salt Form I A solution of Compound (I) was prepared in MeOH (60 mg/mL). 2.2 equivalents of HCl was added to 0.6 mL of EtOH. 0.5 mL of the MeOH/Compound (I) solution was added to the EtOH/HCl solution. The mixture was stirred at 45° C. for 1.5 h, and then cooled to room temperature and stirred overnight. The mixture was then filtered and an XRPD was taken of the wet solid (FIG. 4A). This form was identified as Form I of the HCl salt. Form I was stable to drying but deliquesced at elevated humidity.

b) Pralsetinib HCl Salt Form II and Pralsetinib HCl Salt Form III

A solution of Compound (I) was prepared in MeOH (60 mg/mL). 2.2 equivalents of HCl was added to 0.6 mL (25 volumes) of IPA/water (9:1). 0.5 mL of the MeOH/Compound (I) solution was added to the IPA/HCl solution. The mixture was stirred at 45° C. for 1.5 h, and then cooled to room temperature and stirred overnight. The mixture was then filtered and an XRPD was taken of the wet solid. This wet form was identified as Form II of the HCl salt. This material was then dried at 50° C. under vacuum for 3 hours to remove any remaining solvent. Once dried, Form II converted to Form III that was stable to humidification and stability.

Example 4: Pralsetinib Amorphous Solid Dispersion Preparation

Methanol was added to a feed vessel. To this feed vessel was added pralsetinib free base (e.g., in any of the crystalline forms described herein (e.g., Forms A, B, and C) or as an amorphous form) and HPMC-E3 in a 1:1 w/w ratio and the mixture was stirred to provide a solution.

| Component | % w/w |
|---|---|
| Methanol | 92.0 |
| pralsetinib free base | 4.0 |
| HPMC-E3 | 4.0 |
| Total | 100.0 |

Example 5: Immediate Release Compositions

An effervescent disintegration mechanism using a water-soluble acid (e.g., citric acid) in combination with a water-soluble base (e.g., sodium bicarbonate or sodium carbonate) was used to overcome the rapid formation of a HPMC gel network in the pralsetinib/HPMC amorphous solid dispersion (ASD) preparation obtained from Example 4 upon exposure to an aqueous environment. For the experiments described in Example 5, an HPMC-E3 placebo ASD was utilized for capsule prototyping to conserve limited API. A static disintegration test was performed where the capsule was exposed to 0.1 M HCl. The time taken for the capsule to disintegrate was recorded.

5a. Sodium Bicarbonate/Anhydrous Citric Acid Effervescent Couple

An effervescent system of sodium bicarbonate and citric acid was performed using the following formulation:

| Component | Composition (% w/w) | Batch Composition (g) |
|---|---|---|
| ASD (HPMC-E3) | 50.0 | 5.0 |
| Sodium Bicarbonate | 33.3 | 3.3 |
| Citric Acid | 16.7 | 1.7 |
| Total | 100.0 | 10.0 |

The ingredients were blended and dry granulated using a "slugging" method achieving a bulk density of approximately 0.6 g/mL. No extragranular components were included. Granules were hand filled into gelatin capsules and subjected to the described static disintegration test. The capsule began to disintegrate at three minutes with a clear sign of effervescence.

5b. Addition of Diluent and Lubricant

To aid the manufacturing process, a diluent and lubricant were added:

| Component | Composition (% w/w) | Batch Composition (g) |
|---|---|---|
| Intragranular | | |
| ASD (HPMC-E3) | 50.0 | 5.00 |
| Sodium Bicarbonate | 25.0 | 2.50 |
| Citric Acid | 9.0 | 0.90 |
| Microcrystalline Cellulose (Avicel ® PH 102) | 15.0 | 1.50 |
| Magnesium Stearate | 0.5 | 0.05 |
| Extragranular | | |
| Magnesium Stearate | 0.5 | 0.05 |
| Total | 100.0 | 10.00 |

The same dry granulation process as described in 5a was used. Extragranular magnesium stearate was blended for two minutes. An equivalent final blend bulk density to example 5a was achieved. The composition was hand filled into gelatin capsules and subjected to the described static disintegration test. With the reduction in the quantities of sodium bicarbonate and anhydrous citric acid, the capsules took slightly longer to disintegrate than those manufactured during 5a, but still within a desirable time frame.

5c. Sodium Carbonate/Anhydrous Citric Acid Effervescent Couple

Sodium bicarbonate was replaced with sodium carbonate as it is known that sodium carbonate is slightly less hygroscopic than sodium bicarbonate, which could reduce potential for formulation instability. The composition is as follows:

| Component | Composition (% w/w) | Batch Composition (g) |
|---|---|---|
| Intragranular | | |
| ASD (HPMC-E3) | 50.0 | 5.00 |
| Sodium Carbonate | 25.0 | 2.50 |
| Citric Acid | 9.0 | 0.90 |
| Microcrystalline Cellulose (Avicel ® PH 102) | 15.0 | 1.50 |
| Magnesium Stearate | 0.5 | 0.05 |
| Extragranular | | |
| Magnesium Stearate | 0.5 | 0.05 |
| Total | 100.0 | 10.00 |

The same manufacturing process as described in 5b was used, achieving an equivalent final blend bulk density to example 5b. The composition was hand filled into gelatin capsules and subjected to the described static disintegration test. Equivalent disintegration behavior was observed for 5b and 5c.

5d. Effer-Soda®/Anhydrous Citric Acid Effervescent Couple

Effer-Soda® is predominantly sodium bicarbonate, with a modified surface to contain 8 or 12% sodium carbonate. This surface modification prevents incidental moisture from contacting the sodium bicarbonate, which could lead to formulation instability. The Effer-Soda® composition is as follows:

| Component | Composition (% w/w) | Batch Composition (g) |
|---|---|---|
| Intragranular | | |
| ASD (HPMC-E3) | 50.0 | 5.00 |
| Effer-Soda ® | 25.0 | 2.50 |
| Citric Acid | 9.0 | 0.90 |
| Microcrystalline Cellulose (Avicel ® PH 102) | 15.0 | 1.50 |
| Magnesium Stearate | 0.5 | 0.05 |
| Extragranular | | |
| Magnesium Stearate | 0.5 | 0.05 |
| Total | 100.0 | 10.00 |

The same manufacturing process as described in 5b was used, achieving an equivalent final blend bulk density to example 5b. The composition was hand filled into gelatin capsules and subjected to the described static disintegration test. Equivalent disintegration behavior was observed for 5b, c and d.

5e. and 5f. Reduction of Amount of Sodium Carbonate (5e) and Effer-Soda® (5f)

To minimize the level of hygroscopic excipients within the composition, lower levels of sodium carbonate and Effer-Soda® were investigated. Resulting compositions are shown for 5e and 5f, respectively:

| Component (5e) | Composition (% w/w) | Batch Composition (g) |
|---|---|---|
| Intragranular | | |
| ASD (HPMC-E3) | 50.0 | 5.00 |
| Sodium Carbonate | 10.0 | 1.00 |
| Citric Acid | 9.0 | 0.90 |
| Microcrystalline Cellulose (Avicel ® PH 102) | 30.0 | 3.00 |
| Magnesium Stearate | 0.5 | 0.05 |
| Extragranular | | |
| Magnesium Stearate | 0.5 | 0.05 |
| Total | 100.0 | 10.00 |

The same manufacturing process as described in 5b was used, achieving an equivalent final blend bulk density to example 5b. The final blend was passed through a 1 mm sieve and hand filled into gelatin capsules and subjected to the described static disintegration test. Upon disruption of the capsule shell, immediate effervescence was observed, and complete disintegration and dissolution was achieved by 45 minutes.

| Component (5f) | Composition (% w/w) | Batch Composition (g) |
|---|---|---|
| Intragranular | | |
| ASD (HPMC-E3) | 50.0 | 5.00 |
| Effer-Soda ® | 10.0 | 1.00 |
| Citric Acid | 9.0 | 0.90 |
| Microcrystalline Cellulose (Avicel ® PH 102) | 30.0 | 3.00 |
| Magnesium Stearate | 0.5 | 0.05 |

-continued

| Component (5f) | Composition (% w/w) | Batch Composition (g) |
|---|---|---|
| Extragranular | | |
| Magnesium Stearate | 0.5 | 0.05 |
| Total | 100.0 | 10.00 |

Composition 5f followed the same manufacturing process as detailed for 5e and again achieving a bulk density of approximately 0.6 g/mL. The final blend was passed through a 1 mm sieve and hand filled into gelatin capsules and subjected to the described static disintegration test. Upon disruption of the capsule shell, immediate effervescence was observed, and complete disintegration and dissolution was achieved by 45 minutes. Equivalent disintegration behavior was observed for 5e and f There was no apparent impact of reduced levels of effervescent couples on static disintegration of the composition in 0.1 M HCl.

5g. Addition of a Moisture Scavenger

Pregelatinized starch was introduced into the composition as a moisture scavenger to promote long term stability due to the hygroscopic nature of the effervescent couple. The following composition was prepared:

| Component | Composition (% w/w) | Batch Composition (g) |
|---|---|---|
| Intragranular | | |
| ASD (HPMC-E3) | 50.0 | 5.00 |
| Effer-Soda ® | 15.0 | 1.50 |
| Citric Acid | 9.0 | 0.90 |
| Starch 1500 ® | 25.0 | 2.50 |
| Magnesium Stearate | 0.5 | 0.05 |
| Extragranular | | |
| Magnesium Stearate | 0.5 | 0.05 |
| Total | 100.0 | 10.00 |

The same manufacturing process as described in 5b was used, achieving an equivalent final blend bulk density to example 5b. The final blend was passed through a 1 mm sieve and hand filled into gelatin capsules and subjected to the described static disintegration test. Capsule and contents disintegrated and dissolved within 40 minutes.

5h. Reduction in Amount of Moisture Scavenger

The following composition was prepared to establish the adequate level of pregelatinized starch required to produce a final blend with desirable material properties, for example, bulk density and flow:

| Component | Composition (% w/w) | Batch Composition (g) |
|---|---|---|
| Intragranular | | |
| ASD (HPMC-E3) | 50.0 | 5.00 |
| Effer-Soda ® | 20.0 | 2.00 |
| Citric Acid | 9.0 | 0.90 |
| Starch 1500 ® | 20.0 | 2.00 |
| Magnesium Stearate | 0.5 | 0.05 |

-continued

| Component | Composition (% w/w) | Batch Composition (g) |
|---|---|---|
| Extragranular | | |
| Magnesium Stearate | 0.5 | 0.05 |
| Total | 100.0 | 10.00 |

The same manufacturing process as described in 5b was used, achieving an equivalent final blend bulk density to example 5b. The final blend was passed through a 1 mm sieve. Blend was hand filled into size 1 HPMC capsule shells (for example, Vcaps® Plus) rather than the size 0 gelatin capsules used for 5a-5f. The HPMC capsule (Vcaps® Plus) were filled to the maximum capacity to investigate if a tightly packed capsule still adequately disintegrated. The resulting capsule was subjected to the described static disintegration test. Although a size 1 Vcaps® Plus capsule was filled to its maximum capacity, comparable disintegration to size 0 gelatin capsules containing Starch 1500®, Effer-Soda® and citric acid was observed.

5i. Compositions 1, 2 and 3: Additional Compositions

Compositions 1, 2, and 3, which include the pralsetinib amorphous solid dispersion described in Example 4, were also prepared.

Composition 1

| Component | Composition (% w/w) | Batch Composition (g) |
|---|---|---|
| Intragranular | | |
| ASD (Example 4) | 50.0 | 27.69 |
| Effer-Soda ® | 25.0 | 13.76 |
| Citric Acid | 9.0 | 4.95 |
| Microcrystalline Cellulose (Avicel Ph102) | 15.0 | 8.26 |
| Magnesium Stearate | 0.5 | 0.28 |
| Extragranular | | |
| Magnesium Stearate | 0.5 | 0.25* |
| Total | 100.0 | 52.20 |

*Adjusted based on intragranular yield

Composition 2

| Component | Composition (% w/w) | Batch Composition (g) |
|---|---|---|
| Intragranular | | |
| ASD (Example 4) | 50.0 | 27.60 |
| Effer-Soda ® | 25.0 | 13.76 |
| Citric Acid | 9.0 | 4.99 |
| Microcrystalline Cellulose (Avicel Ph102) | 10.0 | 5.530 |
| Magnesium Stearate | 0.5 | 0.28 |
| Extragranular | | |
| Magnesium Stearate | 0.5 | 0.25* |
| Starch 1500 ® | 5.0 | 2.41* |
| Total | 100.0 | 54.82 |

*Adjusted based on intragranular yield

Composition 3

| Component | Composition (% w/w) | Batch Composition (g) |
|---|---|---|
| Intragranular | | |
| ASD (Example 4) | 50.0 | 23.29 |
| Sodium Bicarbonate | 25.0 | 11.63 |
| Citric Acid | 9.0 | 4.19 |
| Microcrystalline Cellulose (Avicel Ph102) | 15.0 | 7.01 |
| Magnesium Stearate | 0.5 | 0.24 |
| Extragranular | | |
| Magnesium Stearate | 0.5 | 0.23* |
| Total | 100.0 | 46.59 |

*Adjusted based on intragranular yield

The manufacturing process for the Compositions 1-3 are as follows:

1) Intragranular components were blended in a suitably sized contained using the Turbula blender for 3 minutes at 23 rpm
2) Intragranular blend was dry granulated by densification using a Riva minipress fitted with 22×9 mm caplet tooling
3) Resultant material was milled using a Comil 193 fitted with 991 μm screen 4) Granule bulk density was determined and if not within 0.55-0.6 g/mL, densification and milling repeated until the desired bulk density was achieved
5) Extragranular components were blend with the granules in a Turbula blender for 2 minutes at 23 rpm
6) Final blend was hand filled in to Size 0 HPMC Capsules (Vcaps® Plus)
7) Capsules were packed into 60 mL HDPE bottles with 4 g desiccant cap at a count of 30 capsules per bottle
8) Packed product was placed on accelerated stability for 4 weeks at 40° C./75% RH All compositions demonstrated physical and chemical stability over the storage conditions and timeframe studied. X-ray powder diffraction (XRPD) shows that the pralsetinib remains as an amorphous solid dispersion over 4 weeks at 40° C./75% RH. Composition 3 demonstrated a faster drug release compared to compositions 1 and 2 achieving more than 85% released in 45 minutes (United States Pharmacopeia (USP) <711> utilizing a Type 2 Apparatus, media containing 900 mL 0.1 M HCl, and a paddle speed of 100 rpm).

5j. Composition 4

Composition 4, which includes the pralsetinib amorphous solid dispersion described in Example 4, was also prepared.

| Material | Formula (wt %) | Formula (mg/capsule) |
|---|---|---|
| ASD (Example 4) | 55.0 | 200.00 |
| MCC (Avicel PH102) | 9.0 | 32.73 |
| Sodium Bicarbonte | 22.0 | 80.00 |
| Citric Acid | 9.0 | 32.73 |
| Magnesium Stearate | 0.5 | 1.82 |
| Total intragranular | 95.5 | 347.28 |
| Starch 1500 | 4.0 | 14.55 |
| Magnesium Stearate | 0.5 | 1.82 |
| Total extragranular | 4.5 | 16.37 |
| Grand Total | 100 | 363.65 |

Intragranular blend was dry granulated using a roller compactor, ribbons were milled through approximately 1 mm screen. Granules were blended with extragranular materials and the final blend was filled into size 0 HPMC capsules using a Profill.

Disintegration time. The time to disintegrate the capsule described as composition 4 was determined using USP <701> Disintegration, in particular, the procedure for uncoated or plain-coated tablets was used. Specifically, a single capsule was placed in each of the 6 tubes of the basket (Basket type A) along with the disc. Analytical grade water was added, and the temperature was maintained at 37° C.±2° C. The disintegration time for the composition 4 capsule was determined to be 6 minutes 14 seconds.

Dissolution Time. The dissolution time for the capsule of composition 4 was determined using the following dissolution protocol:

| Parameter | Requirement |
|---|---|
| Apparatus | USP II (Paddle) |
| Dissolution Media Volume | 900 mL |
| Dissolution Media | pH 6.8 sodium phosphate buffer with 0.5% CetylTrimethyl Ammonium Bromide (CTAB). |
| Dissolution Media Temperature | 37° C. ± 0.5° C. |
| Paddle Speed | 75 rpm ± 2 rpm |
| Sinkers | Standard USP wire sinkers |
| Cannula Filter | 10 μm |
| Membrane Filter | 0.45 μm Nylon membrane filter |
| Volume to be sample at each time point | 10 mL |
| Sampling Time Points | 15, 30, 45, 60, 75, 90, 120 minutes (paddle speed increased to 200 rpm at 90 minutes) |
| Dissolution Time | 120 minutes |

Results:

| Time | Mean | Min | Max |
|---|---|---|---|
| 0 | 0 | 0 | 0 |
| 15 | 60.9 | 47.4 | 70.1 |
| 30 | 89.9 | 84.5 | 94.2 |
| 45 | 96.6 | 93.6 | 99.6 |
| 60 | 98.4 | 95.8 | 101.4 |
| 75 | 98.8 | 96.2 | 101.8 |
| 90 | 98.8 | 96.1 | 102.0 |
| 120 | 98.9 | 96.3 | 101.9 |

5k. Tablet Formulations

Tablet formulations (effervescent couple tablets) were prepared according to the compositions described in the following table at two dosage strengths [50 mg (tablet size: 8.5 mm round) and 200 mg (tablet size: 22×9 mm caplet)].

| Component | Composition (%) | 200 mg Tablet Composition (mg) |
|---|---|---|
| Intragranular | | |
| ASD (50:50) | 40.0 | 400 |
| Avicel PH102 | 34.0 | 340 |
| Ac-Di-Sol | 7.5 | 75 |
| Sodium Bicarbonate | 3.5 | 35 |
| Citric Acid | 1.5 | 15 |
| Magnesium Stearate | 0.5 | 5 |
| Extragranular | | |
| Ac-Di-Sol | 7.5 | 75 |
| Polyplasdone XL | 5.0 | 50 |
| Magnesium Stearate | 0.5 | 5 |
| Total | 100.0 | 1000 |

The ASD was blended with the excipients shown in the table above, all excipients were dispensed and passed through a 1 mm sieve and blended for 15 minutes at 30 RPM. The intragranular blend was subject to dry granulation and milled via a 1 mm screen.

The resulting granules were blended with the extragranular excipients. Tablets were produced from the final blend with a target hardness of 15±3 kp for the 200 mg dose strength and 12±3 kp for the 50 mg dose strength and film coated. Greater than 80% drug release occurred at 30 minutes in pH 6.8 buffer with 0.5% CTAB, USP paddle apparatus at 75 rpm.

Example 6: Comparator Formulations without an Effervescent Couple

Comparative formulations without an effervescent couple were prepared. Instead of an effervescent couple to break apart the polymer matrix, a disintegration agent was used. The disintegration agents tested included crospovidone, croscarmellose sodium and sodium starch glycolate.

Rapid gelation due to HPMC gel matrix formation was observed during disintegration testing in water of prototype capsule formulations including crospovidone and croscarmellose sodium. The formulations containing the disintegration agents crospovidone and croscarmellose sodium did not disintegrate during dissolution testing in 0.1 M HCl and rather showed "plug" formation over the 45-minute testing period. Disintegration over a 15-minute time period is typical for an immediate release formation.

Example 6a and 6b: Comparative Formulations with Disintegration Agents

In contrast to the compositions comprising an effervescent couple as described in Example 5, "plugs" formed from compositions where the disintegration agents croscarmellose sodium and crospovidone where used instead of the effervescent couple.

6a. The Croscarmellose Sodium (Ac-Di-Sol®) Composition:

| Component | Composition (% w/w) | Batch Composition (g) |
|---|---|---|
| Intragranular | | |
| Pralsetinib/HPMC 50:50 (Example 4) | 50.0 | 12.500 |
| Croscarmellose sodium (Ac-di-sol ®) | 5.0 | 1.250 |
| Fumed Silica (Aerosil ® 200) | 1.0 | 0.250 |
| Magnesium Stearate | 0.5 | 0.125 |
| Microcrystalline Cellulose (Avicel ® PH 102) | 28.5 | 7.125 |
| Pearlitol ® 50 | 9.5 | 2.375 |

-continued

| Component | Composition (% w/w) | Batch Composition (g) |
|---|---|---|
| Extragranular | | |
| Croscarmellose sodium (Ac-di-sol ®) | 5.0 | 1.250 |
| Magnesium Stearate | 0.5 | 0.125 |
| Total | 100.0 | 25.0 |

6b. The Crospovidone (Polyplasdone XL 10®) Composition:

| Component | Composition (% w/w) | Batch Composition (g) |
|---|---|---|
| Intergranular | | |
| Pralsetinib/HPMC 50:50 (Example 4) | 50.0 | 12.500 |
| Crospovidone (Polyplasdone ® XL 10) | 5.0 | 1.250 |
| Fumed Silica (Aerosil ® 200) | 1.0 | 0.250 |
| Magnesium Stearate | 0.5 | 0.125 |
| Microcrystalline Cellulose (Avicel ® PH 102) | 28.5 | 7.125 |
| Pearlitol ® 50 | 9.5 | 2.375 |
| Extragranular | | |
| Crospovidone (Polyplasdone ® XL 10) | 5.0 | 1.250 |
| Magnesium Stearate | 0.5 | 0.125 |
| Total | 100 | 25 |

The method of manufacture of the formulations involved blending the ASD initially with the Aerosil® 200 in attempt to coat the ASD particles to enhance the flow properties. Blending was conducted using a Turbula® blender set at 23 revolutions per minute (rpm) for 1 minute. This was followed by blending the remaining intragranular components for 3 minutes at 23 rpm in the Turbula® blender. Dry granulation was then simulated using a Riva Minipress via a process of "slugging" using 22×9 mm caplet shaped tooling with the application of the maximum compression setting. Final slugs were broken down ("milled") into granules using a pestle and mortar and then blended with the extragranular components for 3 minutes in a Turbula® blender. Prior to the manufacture of capsules, the bulk density of the final blend was determined to be approximately 0.6 g/mL. The resultant blend was then hand filled into size 0 gelatin capsules and three (3) capsules were subjected to the following dissolution study:

| Parameter | Setting |
|---|---|
| Dissolution Media | pH 1.2 Buffer |
| Bath Temperature | 37° C. |
| Media Volume | 900 mL |
| Sampling Point | 45 minutes |
| Volume of Sample | 10 mL |
| Dissolution Run Time | 45 minutes |
| Dissolution Apparatus | USP <711> Apparatus II with wire sinkers |
| Paddle Speed | 75 rpm |

The pH 1.2 medium was chosen based on the relatively high solubility of pralsetinib free base in acidic pH. Other method parameters were chosen as typical for USP dissolution testing of solid dosage forms.

Although a dissolution study was initiated, the sampling intended at 45 minutes was aborted because it was visually observed that the subjected capsules had not disintegrated and formed a plug. This observation led to a decision that the formulations outlined in Experiments 6a and 6b were not viable.

Example 7: X-Ray Powder Diffraction (XRPD)

X-ray powder diffraction for Forms A, B, and C and HCl salts Form II and III were performed using a Bruker D8 Advance equipped with a Lynxeye detector (i.e. Bragg-Brentano geometry). Samples were prepared on Si zero-return wafers. Parameters for XRPD are shown below in Table A-1:

TABLE A-1

| Parameter | Regular Scan |
|---|---|
| X-ray wavelength | Cu Kα1, 1.540598 Å |
| X-ray tube setting | 40 kV, 40 mA |
| Slit condition | 0.6 mm div., 2.5° Soller |
| Scan mode | Step |
| Scan range (°2θ) | 4-30 |
| Step size (°2θ) | 0.03 |
| Dwell time (s/step) | 0.23 |
| Spin | Yes (0.5 Hz) |

X-ray powder diffraction for HCl salt Form I was performed using a Rigaku MiniFlex 600 in reflection mode (i.e. Bragg-Brentano geometry). Samples were prepared on Si zero-return wafers. The parameters for XRPD methods used are listed below in Table A-2.

TABLE A-2

| Parameter | Regular Scan | High Resolution Scan |
|---|---|---|
| X-ray wavelength | Cu Kα1, 1.540598 Å | Cu Kα1, 1.540598 Å |
| X-ray tube setting | 40 kV, 15 mA | 40 kV, 15 mA |
| Slit condition | 1.25° div., Ni kβ filter, 0.3 mm rec. | 1.25° div., Ni kβ filter, 0.3 mm rec. |
| Scan mode | Continuous | Continuous |
| Scan range (°2θ) | 4-30 | 4-40 |
| Step size (°2θ) | 0.05 | 0.05 |
| Scan speed (°/min) | 5 | 1.25 |
| Spin | No | No |

The XRPD pattern of pralsetinib Form A is shown in FIG. 1A. The XRPD pattern of pralsetinib Form B is shown in FIG. 2A. The XRPD pattern of pralsetinib Form C is shown in FIG. 3A. The XRPD pattern of pralsetinib HCl salt Form I is shown in FIG. 4A. The XRPD pattern of pralsetinib HCl salt Form II is shown in FIG. 5A. The XRPD pattern of pralsetinib HCl salt Form III is shown in FIG. 6A.

TABLE 1A

XRPD peak list for Pralsetinib Form A

| 2-theta (deg) | d-Spacing (ang.) | Relative Intensity |
|---|---|---|
| 4.95 | 17.82 | 62 |
| 6.80 | 12.98 | 16 |
| 9.74 | 9.07 | 29 |
| 12.71 | 6.96 | 48 |
| 13.62 | 6.50 | 100 |
| 14.82 | 5.97 | 9 |
| 16.06 | 5.52 | 39 |
| 17.18 | 5.16 | 5 |

TABLE 1A-continued

| XRPD peak list for Pralsetinib Form A | | |
|---|---|---|
| 2-theta (deg) | d-Spacing (ang.) | Relative Intensity |
| 17.83 | 4.97 | 8 |
| 19.22 | 4.62 | 20 |
| 19.52 | 4.54 | 35 |
| 20.50 | 4.33 | 5 |
| 21.56 | 4.12 | 6 |
| 23.09 | 3.85 | 14 |
| 23.51 | 3.78 | 16 |
| 24.77 | 3.59 | 5 |
| 25.59 | 3.48 | 10 |
| 25.97 | 3.43 | 9 |
| 27.86 | 3.20 | 7 |
| 29.41 | 3.03 | 7 |

TABLE 1B

| Selected XRPD peak list for pralsetinib Form A | | |
|---|---|---|
| 2-theta (deg) | d-Spacing (ang.) | Relative Intensity |
| 4.95 | 17.82 | 62 |
| 6.80 | 12.98 | 16 |
| 9.74 | 9.07 | 29 |
| 12.71 | 6.96 | 48 |
| 13.62 | 6.50 | 100 |
| 16.06 | 5.52 | 39 |
| 19.22 | 4.62 | 20 |
| 19.52 | 4.54 | 35 |
| 23.51 | 3.78 | 16 |

TABLE 1C

| Further selected XRPD peak list for pralsetinib Form A | | |
|---|---|---|
| 2-theta (deg) | d-Spacing (ang.) | Relative Intensity |
| 4.95 | 17.82 | 62 |
| 9.74 | 9.07 | 29 |
| 12.71 | 6.96 | 48 |
| 13.62 | 6.50 | 100 |
| 16.06 | 5.52 | 39 |

TABLE 2A

| XRPD peak list for pralsetinib Form B | | |
|---|---|---|
| 2-theta (deg) | d-Spacing (ang.) | Relative Intensity |
| 5.89 | 14.99 | 100 |
| 8.81 | 10.03 | 28 |
| 11.58 | 7.64 | 33 |
| 14.73 | 6.01 | 23 |
| 17.01 | 5.21 | 11 |
| 17.63 | 5.03 | 8 |
| 19.45 | 4.56 | 13 |
| 22.21 | 4.00 | 5 |

TABLE 2B

| Selected XRPD peak list for pralsetinib Form B | | |
|---|---|---|
| 2-theta (deg) | d-Spacing (ang.) | Relative Intensity |
| 5.89 | 14.99 | 100 |
| 8.81 | 10.03 | 28 |
| 11.58 | 7.64 | 33 |
| 14.73 | 6.01 | 23 |
| 19.45 | 4.56 | 13 |

TABLE 3A

| XRPD peak list for pralsetinib Form C | | |
|---|---|---|
| 2-theta (deg) | d-Spacing (ang.) | Relative Intensity |
| 5.81 | 15.21 | 100 |
| 8.69 | 10.17 | 32 |
| 10.96 | 8.06 | 60 |
| 11.59 | 7.63 | 21 |
| 11.96 | 7.40 | 14 |
| 13.56 | 6.52 | 48 |
| 14.49 | 6.11 | 21 |
| 17.09 | 5.19 | 12 |
| 18.19 | 4.87 | 6 |
| 19.51 | 4.55 | 11 |
| 20.19 | 4.39 | 29 |
| 20.58 | 4.31 | 12 |
| 21.27 | 4.17 | 8 |
| 22.18 | 4.00 | 20 |
| 22.63 | 3.93 | 7 |
| 23.20 | 3.83 | 10 |
| 24.18 | 3.68 | 6 |
| 24.48 | 3.63 | 9 |
| 26.00 | 3.42 | 10 |
| 26.75 | 3.33 | 7 |
| 28.08 | 3.18 | 5 |

TABLE 3B

| Selected XRPD peak list for pralsetinib Form C | | |
|---|---|---|
| 2-theta (deg) | d-Spacing (ang.) | Relative Intensity |
| 5.81 | 15.21 | 100 |
| 8.69 | 10.17 | 32 |
| 10.96 | 8.06 | 60 |
| 11.59 | 7.63 | 21 |
| 13.56 | 6.52 | 48 |
| 14.49 | 6.11 | 21 |
| 20.19 | 4.39 | 29 |
| 22.18 | 4.00 | 20 |
| 23.20 | 3.83 | 10 |

TABLE 3C

| Further selected XRPD peak list for pralsetinib Form C | | |
|---|---|---|
| 2-theta (deg) | d-Spacing (ang.) | Relative Intensity |
| 5.81 | 15.21 | 100 |
| 8.69 | 10.17 | 32 |
| 10.96 | 8.06 | 60 |
| 13.56 | 6.52 | 48 |
| 20.19 | 4.39 | 29 |

TABLE 4A

| XRPD peak list for pralsetinib HCl salt Form II | | |
|---|---|---|
| 2-theta (θ) | d (Å) | Relative Intensity |
| 5.03 | 17.57 | 100 |
| 6.08 | 14.52 | 27 |
| 9.08 | 9.74 | 36 |
| 9.85 | 8.98 | 55 |
| 13.81 | 6.41 | 18 |
| 14.72 | 6.01 | 47 |
| 15.28 | 5.79 | 12 |
| 17.17 | 5.16 | 18 |
| 18.10 | 4.90 | 15 |
| 19.62 | 4.52 | 21 |
| 20.25 | 4.38 | 8 |
| 20.70 | 4.29 | 28 |
| 21.77 | 4.08 | 22 |
| 24.24 | 3.67 | 16 |
| 25.63 | 3.47 | 23 |
| 26.34 | 3.38 | 6 |

TABLE 5B

| Selected XRPD peak list for pralsetinib HCl salt Form I | | |
|---|---|---|
| 2-theta (θ) | d (Å) | Relative Intensity |
| 5.03 | 17.57 | 100 |
| 6.08 | 14.52 | 27 |
| 9.08 | 9.74 | 36 |
| 9.85 | 8.98 | 55 |
| 14.72 | 6.01 | 47 |

TABLE 5A

| XRPD peak list for pralsetinib HCl salt Form II | | |
|---|---|---|
| 2-theta (deg) | d-Spacing (ang.) | Relative Intensity |
| 6.10 | 14.47 | 56 |
| 8.90 | 9.93 | 100 |
| 9.54 | 9.26 | 22 |
| 15.02 | 5.89 | 6 |
| 16.64 | 5.32 | 15 |
| 17.19 | 5.15 | 7 |
| 17.89 | 4.95 | 13 |
| 18.41 | 4.82 | 8 |
| 19.80 | 4.48 | 6 |
| 25.82 | 3.45 | 21 |
| 26.83 | 3.32 | 36 |

TABLE 5B

| Selected XRPD peak list for pralsetinib HCl salt Form II | | |
|---|---|---|
| 2-theta (deg) | d-Spacing (ang.) | Relative Intensity |
| 6.10 | 14.47 | 56 |
| 8.90 | 9.93 | 100 |
| 9.54 | 9.26 | 22 |
| 15.02 | 5.89 | 6 |
| 16.64 | 5.32 | 15 |

TABLE 6A

| XRPD peak list for pralsetinib HCl salt Form III | | |
|---|---|---|
| 2-theta (deg) | d-Spacing (ang.) | Relative Intensity |
| 5.99 | 14.75 | 6 |
| 6.38 | 13.85 | 42 |
| 8.49 | 10.40 | 55 |
| 8.92 | 9.91 | 100 |
| 9.60 | 9.21 | 48 |
| 11.51 | 7.68 | 9 |
| 12.70 | 6.97 | 8 |
| 15.89 | 5.57 | 5 |
| 16.74 | 5.29 | 21 |
| 17.34 | 5.11 | 28 |
| 19.19 | 4.60 | 9 |
| 21.00 | 4.23 | 7 |
| 26.88 | 3.31 | 7 |

TABLE 6B

| Selected XRPD peak list for pralsetinib HCl salt Form III | | |
|---|---|---|
| 2-theta (deg) | d-Spacing (ang.) | Relative Intensity |
| 6.38 | 13.85 | 42 |
| 8.49 | 10.40 | 55 |
| 8.92 | 9.91 | 100 |
| 9.60 | 9.21 | 48 |
| 11.51 | 7.68 | 9 |
| 16.74 | 5.29 | 21 |
| 17.34 | 5.11 | 28 |
| 19.19 | 4.60 | 9 |

TABLE 6C

| Further selected XRPD peak list for pralsetinib HCl salt Form III | | |
|---|---|---|
| 2-theta (deg) | d-Spacing (ang.) | Relative Intensity |
| 6.38 | 13.85 | 42 |
| 8.49 | 10.40 | 55 |
| 8.92 | 9.91 | 100 |
| 9.60 | 9.21 | 48 |
| 17.34 | 5.11 | 28 |

Example 8: Differential Scanning Calorimetry (DSC)

Differential scanning calorimetry was done using a Mettler Toledo DSC3+. The desired amount of sample is weighed directly in a hermetic aluminum pan with pin-hole. A typical sample mass for is 3-5 mg. A typical temperature range is 30° C. to 300° C. at a heating rate of 10° C. per minute (total time of 27 minutes). Typical parameters for DSC are listed in Table B below.

TABLE B

| Parameters | |
|---|---|
| Method | Ramp |
| Sample size | 3-5 mg |
| Heating rate | 10.0° C./min |
| Temperature range | 30 to 300° C. |
| Method gas | $N_2$ at 60.00 mL/min |

Example 9: Thermogravimetric Analysis and Differential Scanning Calorimetry (TGA and DSC)

Thermogravimetric analysis and differential scanning calorimetry was done using a Mettler Toledo TGA/DSC3+. The desired amount of sample is weighed directly in a hermetic aluminum pan with pin-hole. A typical sample mass for the measurement is 5-10 mg. A typical temperature range is 30° C. to 300° C. (or 350° C.) at a heating rate of 10° C. per minute (total time of 27 minutes). Protective and purge gasses are nitrogen (20-30 mL/min and 50-100 mL/min). Typical parameters for DSC/TGA are listed below in Table C.

TABLE C

| Parameters | |
|---|---|
| Method | Ramp |
| Sample size | 5-10 mg |
| Heating rate | 10.0° C./min |
| Temperature range | 30 to 300° C. |

FIG. 1B shows the Form A DSC thermogram with an endothermic event observed at about 205° C.±2° C.

FIG. 2B shows the Form B DSC thermogram with three features: an endotherm with onset at 149° C.±2° C., an exotherm with onset at 162° C.±2° C., and melting with onset 205° C.±2° C.

FIG. 3B shows the Form C DSC thermogram with onsets occurring at 122°±2° C., 127°±2° C., and 206°±2° C.

FIG. 4B shows the Form I DSC thermogram with a very broad endotherm with an onset temperature of 70.9° C.±2° C. and a sharp endotherm at 240.5° C.±2° C.

FIG. 5B shows the Form II DSC thermogram with a broad endotherm with an onset of 88.7° C.±2° C. and a melt which had an onset of 244.2° C.±2° C.

Figure 6B:
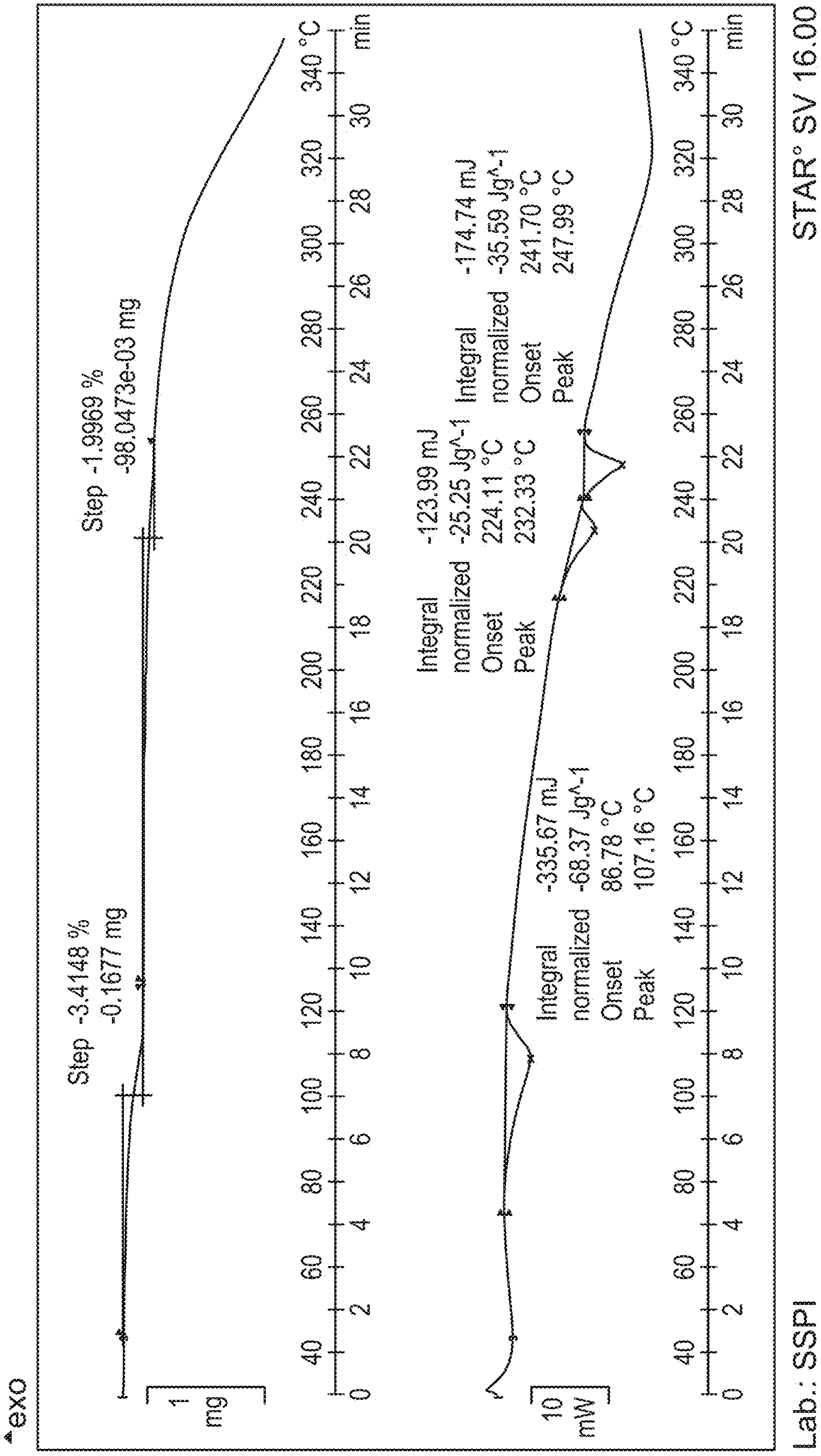
FIG. 6B shows DSC and TGA thermograms of pralsetinib HCl salt Form III.
Figure 7A:
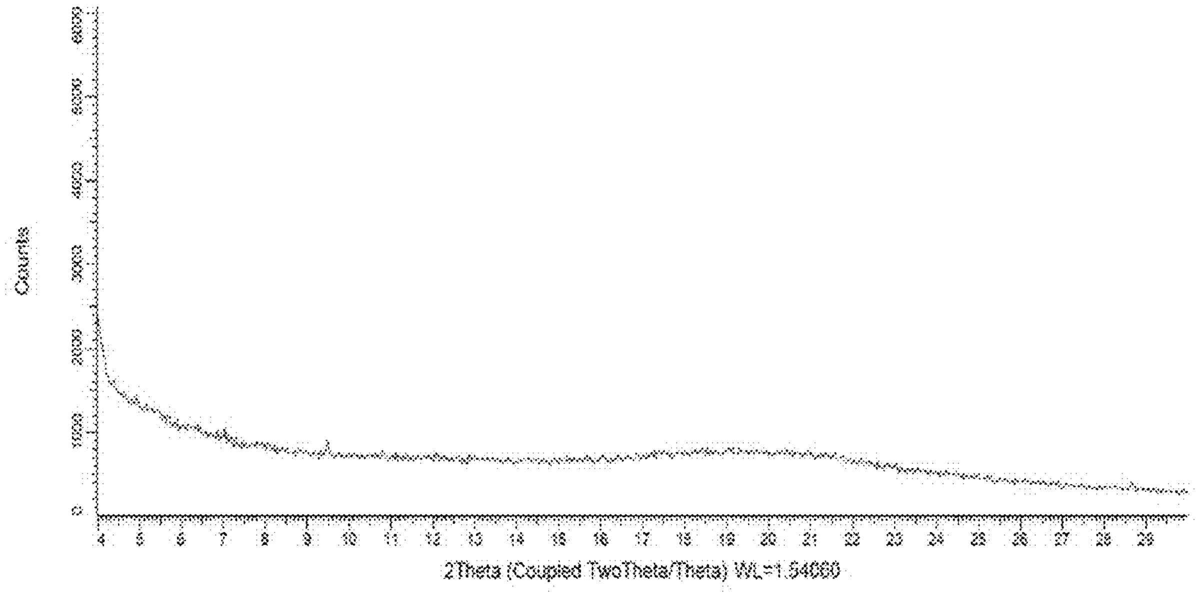
FIG. 7A is an X-ray powder diffraction pattern (XRPD) pattern of pralsetinib amorphous solid dispersion.
Figure 7B:
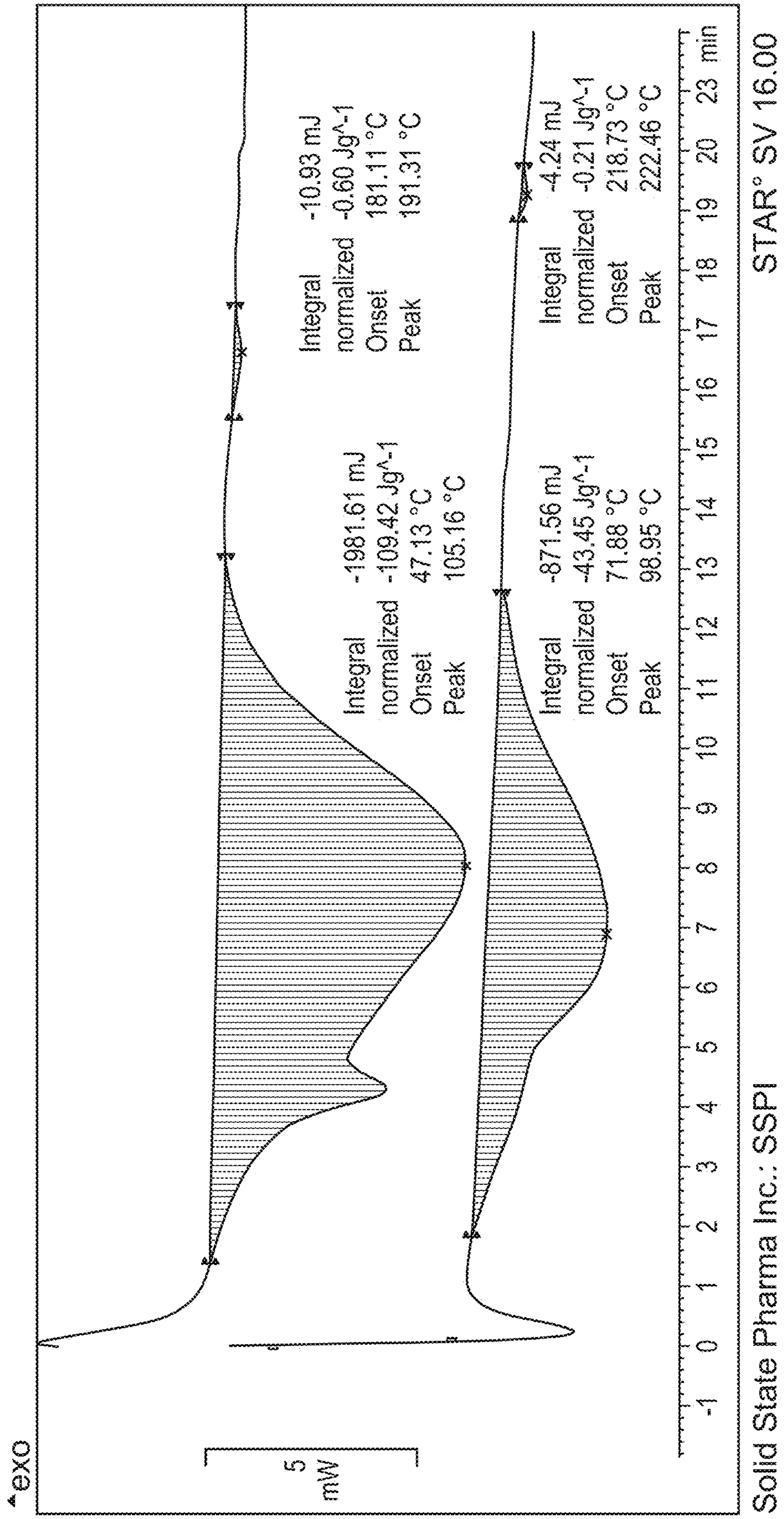
FIG. 7B shows DSC thermogram of pralsetinib amorphous solid dispersion.

FIG. 6B shows the Form III DSC onsets of 86.8° C.±2° C., 224.1° C.±2° C. and 241.7° C.±2° C.

FIG. 1B. shows the TGA pattern of Form A in which a mass loss of 0.8 was observed.

FIG. 2B shows the TGA pattern of Form B in which a mass loss was 0.5% was observed.

FIG. 3B shows the TGA pattern of Form C in which a mass loss of about 3 wt. % was observed.

FIG. 5B shows the TGA pattern of Form II in which a first mass loss of about 3.4 wt. % as well as a second mass loss event of 6.7 wt. % was observed.

FIG. 5C shows the TGA pattern of Form III in which an initial mass loss of 3.4 wt. % and a second mass loss event of 2 wt. % was observed.

Example 10: Dynamic Vapor Sorption (DVS)

Dynamic Vapor Sorption (DVS) was done using a DVS Intrinsic 1. The sample is loaded into a sample pan and suspended from a microbalance. A typical sample mass for DVS measurement is 25 mg. Nitrogen gas bubbled through distilled water provides the desired relative humidity. A typical measurement comprises the steps:

1—Equilibrate at 50% RH

2—50% to 2%. (50%, 40%, 30%, 20%, 10% and 2%)

a. Hold minimum of 5 mins and maximum of 60 minutes at each humidity. The pass criteria is less than 0.002% change 3 —2% to 95% (2%, 10%, 20%, 30%, 40%, 50%, 60%, 70%, 80%, 90%, 95%)

a. Hold minimum of 5 mins and maximum of 60 minutes at each humidity. The pass criteria is less than 0.002% change 4—95% to 2% (95%, 80%, 70%, 60%, 50%, 40%, 30%, 20%, 10%, 2%)

a. Hold minimum of 5 mins and maximum of 60 minutes at each humidity. The pass criteria is less than 0.002% change 5—2% to 50% (2%, 10%, 20%, 30%, 40%, 50%)

a. Hold minimum of 5 mins and maximum of 60 minutes at each humidity. The pass criteria is less than 0.002% change FIG. 1C shows the DVS thermogram of Form A in which a reversible mass change of about 10% by DVS between 2-95% relative humidity is seen.

FIG. 2C shows the DVS thermogram of Form B in which a total mass change of 1.4 wt. % between 2% and 95% relative humidity.

FIG. 3C shows the DVS thermogram of Form C in which a total mass change of 1.4 wt. % between 2% and 95% relative humidity is seen.

A number of embodiments of the invention have been described. Nevertheless, it will be understood that various modifications may be made without departing from the scope of the invention. Accordingly, other embodiments recognized by the person of ordinary skill in the art are within the scope of the following claims.

The invention claimed is:

1. An immediate release oral dosage form comprising:

a) an amorphous solid dispersion comprising: pralsetinib, or a pharmaceutically acceptable salt thereof, and hydroxypropyl methylcellulose E3, wherein the pralsetinib or an equivalent amount of pharmaceutically acceptable salt thereof and the hydroxypropyl methyl cellulose E3 are in about a 1:1 weight ratio;

b) an effervescent couple comprising about 3 to about 13 w/w % citric acid and about 7 to about 30 w/w % sodium bicarbonate; wherein w/w % is based on the total weight of the oral dosage form;

c) a diluent; and d) moisture scavenger and a lubricant, wherein the immediate release oral dosage form comprises the amorphous solid dispersion from about 25% to about 65% percent by weight of the immediate release oral dosage form, based on the total weight of the oral dosage form, and the immediate release oral dosage form is a tablet or a capsule.

2. The oral dosage form of claim 1, wherein the amorphous solid dispersion comprises about 30 mg, about 50 mg, about 60 mg or about 100 mg of pralsetinib or an equivalent amount of a pharmaceutically acceptable salt thereof.

3. The composition of claim 1, wherein the dosage form is a capsule, wherein the capsule disintegrates in about 7 to 15 minutes using USP <701>, with Basket Type A and a disc with a maintained temperature at 37° C.±2° C.

4. The composition of claim 1, wherein the dosage form is a capsule, wherein at least 80% of the pralsetinib is released in about 120 minutes using USP <711> with a Type 2 Apparatus with a media containing 900 mL pH 6.8 sodium phosphate buffer with 0.5% CTAB and a paddle speed of 75 rpm±2 rpm.

5. An immediate release oral dosage form comprising:

a) about 55 w/w % of an amorphous solid dispersion comprising: pralsetinib, or a pharmaceutically acceptable salt thereof, and hydroxypropyl methylcellulose E3, wherein the pralsetinib or an equivalent amount of pharmaceutically acceptable salt thereof and the hydroxypropyl methyl cellulose E3 are in about a 1:1 weight ratio;

b) an effervescent couple comprising about 9 w/w % citric acid and about 22 w/w % sodium bicarbonate;

c) about 9 w/w % microcrystalline cellulose;

d) about 4 w/w % pregelatinized starch; and e) about 1 w/w % magnesium stearate, wherein w/w % is based on the total weight of the oral dosage form, and the immediate release oral dosage form is a tablet or a capsule.

* * * * *